United States Patent
Laaksonen et al.

(10) Patent No.: US 12,270,816 B2
(45) Date of Patent: *Apr. 8, 2025

(54) LIPIDOMIC BIOMARKERS FOR IDENTIFICATION OF HIGH-RISK CORONARY ARTERY DISEASE PATIENTS

(71) Applicant: ZORA BIOSCIENCES OY, Espoo (FI)

(72) Inventors: Reijo Laaksonen, Lampaeaelae (FI); Kim Ekroos, Helsinki (FI); Reini Hurme, Espoo (FI); Riikka Katainen, Helsinki (FI)

(73) Assignee: ZORA BIOSCIENCES OY, Espoo (FI)

( * ) Notice: Subject to any disclaimer, the term of this patent is extended or adjusted under 35 U.S.C. 154(b) by 663 days.

This patent is subject to a terminal disclaimer.

(21) Appl. No.: 17/177,503

(22) Filed: Feb. 17, 2021

(65) Prior Publication Data

US 2021/0239719 A1  Aug. 5, 2021

Related U.S. Application Data

(63) Continuation of application No. 16/291,845, filed on Mar. 4, 2019, now Pat. No. 10,955,427, which is a continuation of application No. 15/803,252, filed on Nov. 3, 2017, now Pat. No. 10,261,101, which is a continuation of application No. 14/875,087, filed on Oct. 5, 2015, now Pat. No. 9,841,431, which is a continuation of application No. 13/805,319, filed as application No. PCT/EP2011/060253 on Jun. 20, 2011, now Pat. No. 9,201,080.

(60) Provisional application No. 61/356,675, filed on Jun. 21, 2010.

(30) Foreign Application Priority Data

Jun. 20, 2010 (EP) .................................... 10006399

(51) Int. Cl.
    *G01N 33/92* (2006.01)

(52) U.S. Cl.
    CPC ......... *G01N 33/92* (2013.01); *G01N 2405/04* (2013.01); *G01N 2405/06* (2013.01); *G01N 2570/00* (2013.01); *G01N 2800/324* (2013.01); *G01N 2800/50* (2013.01); *G01N 2800/52* (2013.01)

(58) Field of Classification Search
    CPC ............... G01N 33/92; G01N 2405/04; G01N 2405/06; G01N 2570/00; G01N 2800/324; G01N 2800/50; G01N 2800/52
    See application file for complete search history.

(56) References Cited

U.S. PATENT DOCUMENTS

| | | |
|---|---|---|
| 7,335,681 B2 | 2/2008 | Shayman |
| 7,879,558 B2 | 2/2011 | Kleinfeld |
| 9,046,538 B2 | 6/2015 | Laaksonen et al. |
| 2002/0164662 A1 | 11/2002 | Hazen et al. |
| 2003/0134304 A1* | 7/2003 | van der Greef ....... G16B 40/00 435/7.1 |
| 2004/0143461 A1 | 7/2004 | Watkins |
| 2006/0154252 A1 | 7/2006 | Marguerie et al. |
| 2007/0099242 A1 | 5/2007 | Heinecke et al. |
| 2008/0003684 A1 | 1/2008 | Laaksonen et al. |
| 2008/0027088 A1 | 1/2008 | Homan et al. |
| 2009/0029473 A1 | 1/2009 | Han |
| 2009/0065687 A1* | 3/2009 | Gross ................. G01N 33/6848 250/281 |
| 2009/0197242 A1 | 8/2009 | Kaddurah-Daouk et al. |
| 2010/0278907 A1 | 11/2010 | Bieberich |
| 2013/0023054 A1 | 1/2013 | Meikle et al. |

FOREIGN PATENT DOCUMENTS

| | | |
|---|---|---|
| CN | 101132789 A | 2/2008 |
| CN | 101522910 | 9/2009 |
| CN | 102971633 A | 3/2013 |
| EP | 1726962 A1 | 11/2006 |
| JP | 2004-531478 A | 10/2004 |
| JP | 2005-504277 A | 2/2005 |
| JP | 2006-510379 A | 3/2006 |
| JP | 2007263979 A | 10/2007 |
| JP | 2007-530528 A | 11/2007 |
| JP | 2008516595 A | 5/2008 |

(Continued)

OTHER PUBLICATIONS

Atherosclerosis Supplement 2009 vol. 10, issue 2, Abstract 105 (Year: 2009).*

(Continued)

*Primary Examiner* — Changhwa J Cheu
(74) *Attorney, Agent, or Firm* — MH2 Technology Law Group, LLP

(57) ABSTRACT

The present invention inter alia provides a method, and use thereof, of predicting severe CVD complications such as AMI or CVD death by detecting the lipid concentrations or lipid ratios of a biological sample and comparing it to a control and has identified specific lipid markers that are more specific and sensitive in predicting these CVD complications than currently utilized clinical markers. Also provided is an antibodies towards said lipids, and the use thereof for predicting, diagnosing, preventing and/or treating CVD complications. The invention additionally relates to kits comprising lipids and/or an antibody thereto, for use in the prediction and/or diagnosis of CVD complications.

14 Claims, 1 Drawing Sheet

(56) References Cited

FOREIGN PATENT DOCUMENTS

| | | |
|---|---|---|
| JP | 2009540314 A | 11/2009 |
| JP | 2010-038858 A | 2/2010 |
| WO | 93/05788 A | 4/1993 |
| WO | 1998/057179 A1 | 12/1998 |
| WO | 01/65257 | 9/2001 |
| WO | 2004/038381 A2 | 5/2004 |
| WO | 2004/085610 | 10/2004 |
| WO | 2005/063275 | 7/2005 |
| WO | 2006/092025 A1 | 4/2006 |
| WO | 2006040409 A1 | 4/2006 |
| WO | 2007/050318 A2 | 5/2007 |
| WO | 2007/127192 | 11/2007 |
| WO | 2007/144467 A1 | 12/2007 |
| WO | 2008/011943 A1 | 1/2008 |
| WO | 2008/118413 A2 | 10/2008 |
| WO | 2008/148857 A1 | 12/2008 |
| WO | 2010/037860 A | 4/2010 |
| WO | 2011/063470 | 6/2011 |
| WO | 2011/138419 | 11/2011 |

OTHER PUBLICATIONS

Bodenheimer (JACC 1994 vol. 24, p. 61-66) (Year: 1994).*
Japanese Office Action dated Jan. 21, 2015 for Japanese Patent Application No. 2013-508512, pp. 1-6.
Chinese Second Office Action dated Jan. 20, 2015 for Chinese Patent Application No. 201180032921.0, pp. 1-11.
Chinese Search Report dated Jan. 20, 2015, Chinese Patent Application No. 201180032921.0, pp. 1-5.
Zhan-qun Pan et al. "Treatment for High-Density Lipoprotein Deficiency", Department of Cardiology, The Second Affiliated Hospital of Nanchang University, Adv Cardiovasc D, vol. 30, No. 3, May 2009, pp. 521-525 (English Translation of Abstract).
Yongzong Yang, Book Titled: Basis and clinic for atherosclerotic cardio-cerebrovascular diseases, Apr. 30, 2004, pp. 277-281.
Lijun Chen, Book Titled: Metabolism (3), Lipid Biochemistry, Nov. 30, 1988, pp. 93-94.
Japanese Office Action dated Jan. 7, 2015, Japanese Patent Application No. 2013-515841, pp. 1-4.
Christin Stegemann et al., "Comparative Lipidomics Profiling of Human Atherosclerotic Plaques", Circulation Cardiovascular Genetics, vol. 4, 2011, pp. 232-242.
Menard M. Gertler et al., "The Interrelationships of Serum Cholesterol, Cholesterol Esters and Phospholipids in Health and in Coronary Artery Disease", Circulation, vol. 11, 1950, pp. 205-214.
Peter J. Meikle et al., "Plasma Lipidomic Analysis of Stable and Unstable Coronary Artery Disease", Arteriosclerosis, Thrombosis, and Vascular Biology, vol. 31, 2011, pp. 2723-2732.
Masahiro Sugano et al., "Effects of diltiazem on suppression and regression of experimental atherosclerosis", Br. J. exp. Path., vol. 69, 1988, pp. 515-523.
Peter John Meikle et al., "Diagnostic and Prognostic Assay", Certified U.S. Appl. No. 61/264,767, filed Nov. 27, 2009, pp. 1-121.
Wikipedia Entry, "Cholesterinester", http://de.wikipedia.org/w/index.php?title=Cholesterinester&oldid=124171453, Version of Oct. 28, 2009, pp. 1-4 (Includes English Language Translation).
Alessandro Floridi et al., "Role of nuclear lipid microdomains on cell function", Sphingolipid Club, http://www.sphingolipidclub.com/previous-meetings/15-non-categorizzato/abstracts/432-role-of-nuclear-lipid-microdomains-on-cell-function.html, Retrieved from the internet on Jan. 14, 2015, p. 1.
Christin Stegemann et al., "Lipidomics Profiling and Risks of Cardiovascular Disease in the Prospective Population-Based Bruneck Study", Circulation, vol. 129, 2014, pp. 1821-1831.
Ikuyo Ichi et al., "Association of Ceramides in Human Plasma with Risk Factors of Atherosclerosis", vol. 41, No. 9, 2006, pp. 859-863.
Dieter M. Kramsch et al., "The Protein and Lipid Composition of Arterial Elastin and Its Relationship to Lipid Accumulation in the Atherosclerotic Plaque", The Journal of Clinical Investigation, vol. 50, 1971, pp. 1666-1677.
G. A. Gribanov et al., "Blood Lipid Changes in Hypoxic Rats", Space Biology and Aerospace Medicine (Russian Journal), No. 6, 1978, pp. 67-71.
A. Beresewicz et al., "Accumulation of Specific Ceramides in Ischemic/Reperfused Rat Heart; Effect of Ischemic Preconditioning", Journal of Physiology and Pharmacology, vol. 53, No. 3, 2002, pp. 371-382.
Yu. N. Borinsky et al., "The Lipid Spectrum of Various Zones of Infarction-Damaged Myocardium as a Reflection of Its Metabolic and Functional Activity in the Period Preceding Fatal Outcome of the Disease", Voprosy Medicinskoj Himii (Russian), 1993, vol. 39, No. 6, pp. 20-22, including English translation.
T. A. Miettinen et al., "Fatty-acid composition of serum lipids predicts myocardial infarction", British Medical Journal, vol. 285, 1982, pp. 993-996.
Joseph H. Rapp et al., "Lipids of human atherosclerotic plaques and xanthomas: clues to the mechanism of plaque progression", Journal of Lipid Research, vol. 24, 1983, pp. 1329-1335.
J. McLaurin et al., "Reactivity of two anti-galactosyl ceramide antibodies towards myelin basic protein", Journal of Neurological Sciences, vol. 108, 1992, pp. 73-79.
Notice of Opposition dated Oct. 8, 2014 filed against European Patent No. EP 2385374 B1, pp. 1-21.
Non-Final Office Action dated Aug. 13, 2014, U.S. Appl. No. 13/695,766, filed Nov. 1, 2012, pp. 1-47.
Communication dated Aug. 25, 2011 from European Patent Application No. 10 162 066.4, pp. 1-4.
Communication dated Jun. 1, 2012 from European Patent Application No. 10 162 066.4, pp. 1-6.
Communication dated Dec. 5, 2012 from European Patent Application No. 10 162 066.4, pp. 1-6.
S. Holewijn et al., "Apolipoprotein B, non-HDL cholesterol and LDL cholesterol for identifying individuals at increased cardiovascular risk", Journal of Internal Medicine, vol. 268, 2010, pp. 567-577.
Vimal Ramjee et al., "Non-High-Density Lipoprotein Cholesterol Versus Apolipoprotein B in Cardiovascular Risk Stratification: Do the Math", Journal of the American College of Cardiology, vol. 58, No. 5, 2011, pp. 457-463.
Allan D. Sniderman et al., "A Meta-Analysis of Low-Density Lipoprotein Cholesterol, Non-High-Density Lipoprotein Cholesterol, and Apolipoprotein B as Markers of Cardiovascular Risk", Circ. Cardiovasc. Qual. Outcomes, May 2011, pp. 337-345.
European Search Report dated Aug. 5, 2010 from European Patent Application No. 10 162 066.4, pp. 1-12.
Stuart J. Pocock et al., "A score for predicting risk of death from cardiovascular disease in adults with raised blood pressure, based on individual patient data from randomised controlled trials", BMJ, vol. 323, Jul. 2001, pp. 75-81.
Ralph B. D'Agostino et al., "Primary and subsequent coronary risk appraisal: New results from The Framingham Study", American Heart Journal, vol. 139, No. 2, Part 1, Feb. 2000, pp. 272-281.
Alessandro Menotti et al., "Comparison of Multivariate Predictive Power of Major Risk Factors for Coronary Heart Diseases in Different Countries: Results from Eight Nations of the Seven Countries Study, 25-Year Follow-up", Journal of Cardiovascular Risk, vol. 3, No. 1, Feb. 1996, pp. 69-75.
Jin M. Cheng et al., "In vivo detection of high-risk coronary plaques by radiofrequency intravascular ultrasound and cardiovascular outcome: results of the ATHEROREMO-IVUS study", European Heart Journal, Nov. 2013, pp. 1-9.
W. G. T. Coppola et al., "Scoring system to identify men at high risk of stroke: a strategy for general practice", British Journal of General Practice, vol. 45, 1995, pp. 185-189.
Jaakko Allonen et al., "Mortality Rate Increases Steeply With Nonadherence to Statin Therapy in Patients With Acute Coronary Syndrome", Clin. Cardiol., vol. 35, No. 11, 2012, pp. E22-E27.
Canadian Office Action dated Jun. 16, 2014, Canadian Application No. 2,798,238, pp. 1-4.
Canadian Office Action dated Jun. 16, 2014, Canadian Application No. 2,801,459, pp. 1-4.

(56) References Cited

OTHER PUBLICATIONS

International Search Report and Written Opinion dated May 11, 2012, International Application No. PCT/EP2011/060253 filed Jun. 20, 2011, pp. 1-32.

Merrill et al., "Sphingolipidomics: High-throughput, structure-specific, and quantitative analysis of sphingolipids by liquid chromatography tandem mass spectrometry", Methods, May 13, 2005, vol. 36, pp. 207-224.

Valsecchi et al., "Ceramide and sphingomyelin species of fibroblasts and neurons in culture", J. Lipid Res., 2007, vol. 48, pp. 417-424.

Lankinen et al., "Fatty Fish Intake Decreases Lipids Related to Inflammation and Insulin Signaling—A Lipidomics Approach", PLoS One online Publication, Apr. 2009, vol. 4, Issue 4, e5258, pp. 1-9.

Samad, F. et al. Altered Adipose and Plasma Sphingolipid Metabolism in Obesity. Diabetes, vol. 55, No. 9, Sep. 2006, pp. 2579-2587.

Melvin, Richard G. et al. Torpor induction in mammals: recent discoveries fueling new ideas. Trends in Endocrinology and Metabolism, vol. 20, No. 10, Dec. 1, 2009, pp. 490-498.

Bhuiyan, M. I. H. et al. Involvement of Ceramide in Ischemic Tolerance Induced by Preconditioning with Sublethal Oxygen-Glucose Deprivation in Primary Cultured Cortical Neurons of Rats. Biological & Pharmaceutical Bulletin, vol. 33, No. 1, Jan. 1, 2010, pp. 11-17.

Yang, G. et al., Central role of ceramide biosynthesis in body weight regulation, energy metabolism, and the metabolic syndrome. Endocrinology and Metabolism, vol. 297, No. 1, Jul. 1, 2009, pp. E211-E224.

Yoo, H. H. et al. Liquid chromatography—tandem mass spectrometric determination of ceramides and related lipid species in cellular extracts. Journal of Chromatography B: Biomedical Sciences & Applications, vol. 843, No. 2, Nov. 7, 2006, pp. 327-333.

Merril, Jr., A. H. et al. Sphingolipidomics: High-throughput, structure-specific, and quantitative analysis of sphingolipids by liquid chromatography tandem mass spectrometry. Methods: A Companion to Methods in Enzymology, vol. 26, No. 2, Jun. 1, 2005, pp. 207-224.

Ichi, I. et al. Effect of dietary cholestrol and high fat on ceramide concentration in rat tissues. Nutrition, vol. 23, No. 7-8, Jul. 1, 2007, pp. 570-574.

Noureddine, L. et al. Modulation of total ceramide and constituent ceramide species in the acutely and chronically hypoxic mouse heart at different ages. Prostaglandis and Other Lipid Mediators, vol. 86, No. 1-4, Jun. 1, 2008, pp. 49-55.

Chatterjee, S. B. et al. Accumulation of glycosphingolipids in human atherosclerotic plague and unaffected aorta tissues. Glycobiology, vol. 7, No. 1, Jan. 1, 1997, pp. 57-65.

Chatterjee, S. B. et al. Increased urinary excretion of glycosphingolipids in familial hypercholesterolemia. The Journal of Lipid Research, vol. 23, No. 4, May 1, 1982, pp. 513-522.

Zheng, W. et al. Ceramides and other bioactive sphingolipid backbones in health and disease: Lipidomic analysis, metabolism and roles in membrane structure, dynamics, signaling and autophagy. Biochimica et Biophysica Acta, vol. 1758, No. 12, Dec. 9, 2006, pp. 1864-1884.

Bielawski, J. et al. Simultaneous quantitative analysis of bioactive sphingolipids by high-performance liquid chromatography-tandem mass spectrometry. Methods: A Companion to Methods in Enzymology, vol. 39, No. 2, Jun. 1, 2006, pp. 82-91.

Hu, Chunxiu et al., Analytical strategies in lipidomics and applications in disease biomarker discovery, Journal of Chromatography B, 877 (2009) 2836-2846, XP026422757.

Stahlman, Marcus et al., High-throughput shotgun lipidomics by quadrupole time-of-flight mass spectrometry, Jounral of Chromatography B, 877 (2009) 2664-2672, XP026422742.

Kaddurah-Daouk, Rima et al., Lipidomic analysis of variation in response to simvastatin in the Cholestrol and Pharamcogenetics Study, Metabolomics, (2010) 6:191-201, XP002592438.

Laaksonen, R., Lipidomics as a tool for atherosclerosis research, New Biotechnology, vol. 27, Apr. 1, 2010, S18-S19, XP026965681.

Ekroos, Kim et al., Lipidomics: A Tool for Studies of Atherosclerosis, Current Atherosclerosis Reports, Jul. 2010, vol. 12, No. 4, pp. 273-281, XP008124463.

Janis, Minna T. et al., Metabolomic strategies to identify tissue-specific effects of cardiovascular drugs, Expert Opinion on Drug Metabolism & Toxicology, Jun. 2008, vol. 4, No. 6, pp. 665-680, XP008124464.

Waterman, Claire L. et al., Metabolomic strategies to study lipotoxicity in cardiovascular disease, Biochimica and Biophysica Acta., vol. 1801, No. 3, Mar. 1, 2010, pp. 230-234, XP026904840.

International Search Report dated Jul. 15, 2011 issued from the European Patent Office for International Application No. PCT/EP2011/057254.

Chinese Fourth Office Action and Search Report dated May 5, 2016 for Chinese Patent Application No. 201180035877.9, pp. 1-12.

Mello et al., "Link between plasma ceramides, inflammation and insulin resistance: association with serum IL-6 concentration in patients with coronary heart disease", Diabetologia, 2009, vol. 52, pp. 2612-2615.

Kasumov et al., "Quantification of ceramide species in biological samples by liquid chromatography electrospray onization tandem mass spectrometry", Analytical Biochemistry, 2010, vol. 401, pp. 154-161.

M. Cameron Sullards, "Lipidomic analysis of sphingolipids (and precursor fatty acyl-CoA's)", LIPID MAPS Lipidomics Workshop EB2009, Apr. 19, 2009, Schools of Chemistry, Biochemistry and Biology & Petit Institute for Bioengineering and Bioscience, Georgia Institute of Technology, 28 pages.

Kadowaki et al., "Relationship of membrane phospholipid composition, lactosylceramide molecular species, and the specificity of CMP-N-acetylneuraminate:lactosylceramide $\alpha$2,3-sialytransferase to the molecular species composition of GM3 ganglioside", Journal of Lipid Research, 1995, vol. 36, pp. 1274-1282.

Japanese Office Action Mar. 12, 2018 for Japanese Patent Application No. 2017-042837, 10 pages with English translation.

Ejsing et al., "Global analysis of the yeast lipidome by quantitative shotgun mass spectrometry", Proc Natl Acad Sci, Feb. 17, 2009, vol. 106, No. 7, pp. 2136-2141.

Hiukka et al., "ApoCIII-Enriched LDL in Type 2 Diabetes Displays Altered Lipid Composition, Increased Susceptibility for Sphingomyelinase, and Increased Binding to Biglycan", Diabetes, Sep. 2009, vol. 58, pp. 2018-2026.

Linden et al., "Liver-directed overexpression of mitochondrial glycerol-3-phosphate acyltransferase results in hepatic steatosis, increased triacylglycerol secretion and reduced fatty acid oxidation", FASEB J., Mar. 2006, vol. 20, pp. 434-443.

Han et al., "Global analyses of cellular lipidomes directly from crude extracts of biological samples by ESI mass spectrometry: a bridge to lipidomics", Journal of Lipid Research, 2003, vol. 44, pp. 1071-1079.

Brugger et al., "Quantitative analysis of biological membrane lipids at the low picomole level by nano-electrospray ionization tandem mass spectrometry", Proc. Natl. Acad. Sci. USA, Mar. 1997, vol. 94, pp. 2339-2344.

Ekroos et al, "Charting molecular composition of phosphatidylcholines by fatty acid scanning and ion trap MS3 fragmentation", Journal of Lipid Research, 2003, vol. 44, pp. 2181-2192.

Folch et al., "A simple method for the isolation and purification of total lipids from animal tissues", J. Biol. Chem., 1957, vol. 226, No. 1, pp. 497-509.

Shinzawa-Itoh et al., "Structures and physiological roles of 13 integral lipids of bovine heart cytochrome c oxidase" EMBO Journal, 2007, vol. 26, pp. 1713-1725.

Office Action and Search Report dated Apr. 2, 2020 for Chinese Patent Application No. 201711362402.6, 29 pages with English translation.

\* cited by examiner

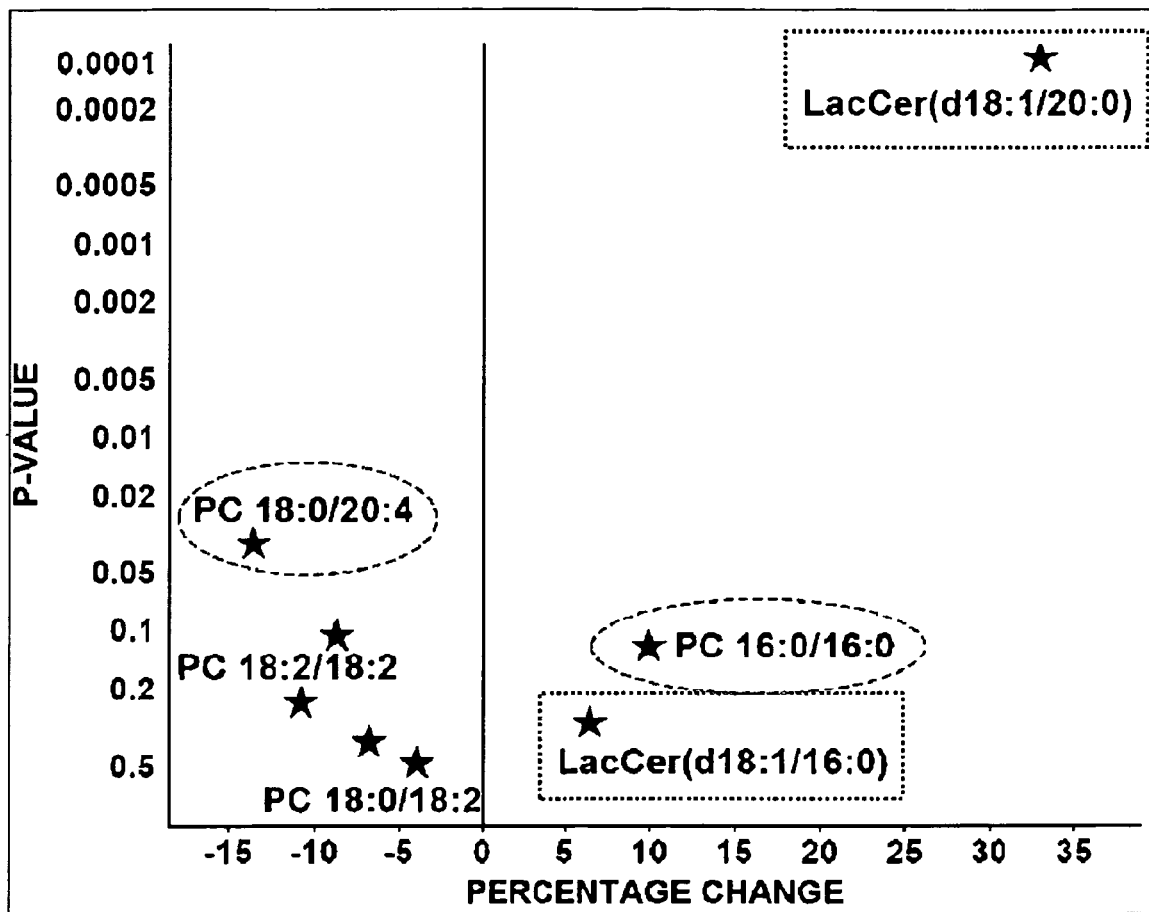

LIPIDOMIC BIOMARKERS FOR IDENTIFICATION OF HIGH-RISK CORONARY ARTERY DISEASE PATIENTS

CROSS REFERENCE TO RELATED APPLICATIONS

This application is a continuation of U.S. application Ser. No. 16/291,845 (Allowed) filed 4 Mar. 2019, which is a continuation of U.S. application Ser. No. 15/803,252 filed 3 Nov. 2017 (now U.S. Pat. No. 10,261,101), which is a continuation of U.S. application Ser. No. 14/875,087 filed 5 Oct. 2015 (now U.S. Pat. No. 9,841,431), which is a continuation of U.S. application Ser. No. 13/805,319, filed 18 Dec. 2012 with a 371 date of 13 Feb. 2013 (now U.S. Pat. No. 9,201,080), which is a U.S. National Stage application of PCT/EP2011/060253 filed 20 Jun. 2011, which claims the benefit of priority of European patent application 10006399.9 filed 20 Jun. 2010 and U.S. Provisional Patent Application 61/356,675 filed 21 Jun. 2010, the entire disclosures of which are herein incorporated by reference in their entireties.

FIELD OF THE INVENTION

This invention relates to methods and uses involving lipid levels to predict and prevent severe cardiovascular disease-associated fatal complications. The invention thus provides a means to identify and treat high-risk coronary artery disease patients. The methods include analyzing lipid levels of a biological sample, and comparing it to a control.

BACKGROUND OF THE INVENTION

Worldwide, cardiovascular diseases (CVD) are among the leading causes of mortality and morbidity with ever-increasing prevalence. CVD is used to classify numerous conditions that affect the heart, heart valves, blood, and vasculature of the body. One of these conditions is coronary artery disease (CAD). Early targeted initiation of preventive measures of CVD-related fatal complications, such as acute myocardial infarction (AMI) and death, would be of great benefit and can provide a major opportunity in reducing mortality and morbidity in patients suffering from CVD. To this end, accurate identification of individuals who are at risk of developing CVD complications is essential. However, traditional risk assessment fails to recognize a substantial proportion of patients at high risk while a large proportion of individuals are classified as having intermediate risk, leaving patient management uncertain. Additional strategies to further refine risk assessment of high-risk CVD are therefore highly needed. To this end, the inventors have evaluated the role of novel lipidomic biomarkers as a prognostic tool for fatal cardiovascular events in CVD patients.

Plasma or serum total cholesterol, LDL-cholesterol or HDL-cholesterol concentrations have been used as gold standard biomarkers for CVD/CAD risk prediction. However, a number of coronary artery disease (CAD) or acute myocardial infarction (AMI) patients have LDL-C levels within the recommended range suggesting the need for additional diagnostic measures of the residual risk. It is evident from earlier large scale population studies that these measurements associate with the CAD risk and CAD endpoints such as AMI or cardiovascular death. Therefore, preventive treatment strategies have so far been addressed to lower LDL-C concentrations (mainly by statin treatment) and more recently also attempts to raise HDL-C have been made (e.g., by CETP-inhibitors). On the other hand, it has also been observed that one half of the AMI patients actually do have normal LDL cholesterol levels and that there is a substantial residual risk in statin treated patients despite a LDL-C lowering. Furthermore, recent publications have demonstrated that plasma levels of apolipoprotein B (apoB), the main surface protein on LDL particles, and LDL-C, the amount of cholesterol in those particles, are correlated and, considered separately, as positive risk factors. Plasma levels of apolipoprotein $A_1$, the main surface protein on HDL particles, and HDL-C, the amount of cholesterol in those particles, are also correlated with each other and, considered separately, as negative risk factors. Importantly, for a given usual apoB, lower LDL-C has been observed to associate with a higher risk of AMI supporting the view that, on average, LDL particles with low cholesterol content per particle (small, dense LDL particles) are particularly hazardous. Thus, it seems possible that LDL-C associates directly with the more dangerous molecules carried by LDL-particle and that LDL-C is only an indirect measurement of the risk. Therefore, it is of importance to search for molecules e.g., certain lipid species that are directly related with hazardous (i.e., fatal) cardiovascular events.

Lipid metabolite imbalance is a probable cause of dyslipidemia and the ensuing atherosclerosis manifested in its gravest form as the vulnerable atherosclerotic plaque. Atherosclerotic plaques are complex molecular formations that contain numerous lipids. However, there are other factors than lipid rich plaques or LDL cholesterol that make lipids an attractive group of molecules for CVD studies. Lipids are tightly regulated which makes Lipidomic data robust and informative on the current state of the studied organism. Also, lipids are one of the culmination points of a biological system, more the true outcome than the predictor. Combining Lipidomic data with appropriate biobanked clinical material presents a good opportunity for biomarker discovery. Moreover, lipidomics can be used as a gauge of efficacy and safety in drug development and evolving theragnostics. Lipidomic biomarkers are prime candidates for true companion diagnostics in the CVD area and present many opportunities for improved translational medicine as well.

The plaque building blocks and lipoprotein components that are thought to traffic lipids to the site of lesion formation can now be resolved with Lipidomic studies correlating lipid structure and composition to function and thereby disease pathogenesis. While the number of lipid mediators in the human body is overwhelming, their identification and quantification is facilitated by the advances in mass spectrometry and lipid biochemistry, which today enable the simultaneous high throughput identification and quantification of hundreds of molecular lipid species in several lipid classes (Ejsing C S, et al: Global analysis of the yeast lipidome by quantitative shotgun mass spectrometry. *Proc Natl Acad Sci USA* 2009, 106:2136-2141; Stahlman M, et al: *High-throughput shotgun lipidomics by quadrupole time-of-flight mass spectrometry. J Chromatogr B Analyt Technol Biomed Life Sci* 2009 Hiukka A, et al: *ApoCIII-enriched LDL in type 2 diabetes displays altered lipid composition, increased susceptibility for sphingomyelinase, and increased binding to biglycan. Diabetes* 2009, 58:2018-2026; Linden D, et al: *Liver-directed overexpression of mitochondrial glycerol-3-phosphate acyltransferase results in hepatic steatosis, increased triacylglycerol secretion and reduced fatty acid oxidation. FASEB J* 2006, 20:434-443.) collectively referred to as the lipidome. Lipidomic studies identify lipid cellular distribution and describe their biochemical mechanisms, interactions and dynamics. Importantly, lipidomics quantifies the exact chemical composition of lipidomes (Han X, Gross R W: *Global analyses of cellular lipidomes directly from crude extracts of biological samples by ESI mass spectrometry: a bridge to lipidomics. J Lipid Res* 2003, 44:1071-1079).

Due to both high sensitivity and selectivity of lipidomics, even the smallest sample amounts can be analyzed today. The bulk of the lipid data in the art today presents lipids in a sum composition format, i.e. phosphatidylcholine (PC) 34:1 (Brugger B, et al: *Quantitative analysis of biological membrane lipids at the low picomole level by nano-electrospray ionization tandem mass spectrometry. Proc Natl Acad Sci USA* 1997, 94:2339-2344) where the molecular lipid and the attached fatty acid tails remain unidentified. The identification of molecular lipid species, e.g., PC 16:0/18:1 (Ekroos K, et al: *Charting molecular composition of phosphatidylcholines by fatty acid scanning and ion trap MS3fragmentation. J Lipid Res* 2003, 44:2181-2192) is the main feature of advanced lipidomics, which delivers highly resolved molecular lipid species rather than summed fatty acid information. For example, the information of the type of fatty acids and their positions of attachment to the glycerol backbone making up the particular PC molecule is revealed. There are conventional techniques such as thin-layer chromatography combined with gas chromatography but they not only require considerably larger sample amounts and laborious sample preparation, but they do not deliver the molecular lipid species. Despite multiple mass spectrometry techniques capable of characterizing lipid entities, most of them are still unable to deliver reliable high-quality quantitative data in terms of absolute or close-to absolute concentrations. In the context of the present invention, electrospray ionization mass spectrometry-based lipidomics is the preferred technology and can utilize both shotgun and targeted lipidomics for exhaustive deciphering and precise quantification of molecular lipidomes. The superior quality and specificity of shotgun and targeted lipidomics will meet stringent regulatory standards, such as good laboratory practice guidelines (GLP) when set-up in the proper environment. Using these technologies quantification of up to two thousand molecular lipids is possible even in a high throughput format.

Lipidomics is a tool for differentiating patients based on their molecular lipid profiles. Personalized medicine and diagnostics enabled by lipidomics will facilitate the mission of the right individual receiving the right drug at the right time and dose. Several works employing analytes consisting of lipids, proteins and hydrophilic molecules among many others have been conducted to meet the needs of personalized medicine. Recently, non-hypothesis-driven metabolomic screenings have been used to identify novel CVD biomarkers.

For example, WO2004/038381 discloses a method for metabolomically facilitating the diagnosis of a disease state of a subject, or for predicting whether a subject is predisposed to having a disease state wherein the small molecule profile from a subject is obtained and compared to a standard small molecule profile.

WO2008/148857 discloses a method to assess the risk of cardiovascular disease in a patient (including atherosclerosis) by isolating the HDL fraction and sub-fraction from a blood sample of the patient. The components of the HDL fraction or sub-fraction to be measured were Sphingosine-1-Phosphate (SiP), sphingomyelin (SM) and Apolipoprotein A-I (apoA-1).

WO2008/11943 further discloses markers for detecting coronary artery disease that can indicate a patient at risk of having or developing coronary artery disease. These include 15 "first-choice" molecules which were: C18:3 Cholesterol ester, C32:1 Phosphatidylcholine, Alanine, Lipid (mainly VLDL), Lysine, Hexadecanoic acid, C36:2 Phosphatidylcholine, Formate, C32:2 Phosphatidylcholine, C18:2 (Linoleic Acid), Cholesterol, C 18:2 Lyso-phosphatidylcholine, C36:3 Phosphatidylcholine, C34:4 Phosphatidylcholine and C34:3 Phosphatidylcholine.

Furthermore, US2007/0099242 describes a method to determine if a subject is at risk to develop, or is suffering from cardiovascular disease. The method involves determining a change in the amount of a biomarker in the biological sample or HDL sub-fraction thereof, compared to a control sample, wherein the biomarker is at least one of Apolipoprotein C-IV ("ApoC-IV"), Paraoxonase 1 ("PON-1"), Complement Factor 3 ("C3"), Apolipoprotein A-IV ("ApoA-IV"), Apolipoprotein E ("ApoE"), Apolipoprotein LI ("ApoL1"), Complement Factor C4 ("C4"), Complement Factor C4B1 ("C4B1"), Histone H2A, Apolipoprotein C-II ("ApoC-II"), Apolipoprotein M ("ApoM"), Vitronectin, Haptoglobin-related Protein and Clusterin. The document also discloses a method for detecting the presence of one or more atherosclerotic lesions wherein a change in the amount of a biomarker in the biological sample or HDL sub-fraction thereof is detected, compared to a control sample and wherein the biomarker is selected from PON-1, C3, C4, ApoE, ApoM and C4B1. All biomarkers mentioned in this document are protein or lipoprotein biomarkers.

From previous work it cannot be extrapolated that lipid analysis will yield by default a CVD biomarker predictive to the fatal outcomes associated with CVD/CAD. The present invention identifies biomarkers of high risk CVD by absolute, or close to absolute, quantification of defined molecular lipid species instead of profiling multiple analytes. Importantly, while many of the existing biomarker candidates are composite fingerprints of multiple factors, the lipidomics approach herein shows value already at a level of single species or ratios thereof.

In the present invention herein, lipid biomarker concentrations have been measured and quantified in patients with documented CAD who did not show fatal outcomes during the follow-up period (3 years) and in high-risk CAD patients who died due to cardiovascular events during the follow-up period. This invention thus enables accurate usage of the lipid-based biomarkers to identify high risk CVD/CAD patients. Another layer of accuracy was reached through a careful patient selection since it is important to control for factors which may affect the lipid concentration read-outs. Unlike the previous efforts described above, we used specific targeted platforms on a singular technology set-up to analyze lipid species in particular.

The technology and the way it was applied in the context of the inventive teaching presented herein is set apart from similar efforts in the field inter alia due to the following criteria. In sample preparation, samples are strictly controlled and treated identically to avoid potential artifacts that could arise from improper handling. In connection with the present invention, samples were carefully thawed slowly on ice and directly thereafter subjected to a custom-made automated lipid extraction which possesses currently the highest precision in liquid handling, therefore minimizing potential errors. Furthermore, sample freeze-thaw cycles were strictly controlled since this can dramatically affect the lipid stabilities. The automated lipid extraction is based on the method by Folch and colleagues (Folch J, et al: *A simple* method for the isolation and purification of total lipids from animal tissues. J Biol Chem 1957, 226(1):497-509) which uses chloroform and methanol. This method is preferred when a wide range, from polar to non-polar, of lipid classes are to be extracted with optimal recoveries thus preventing the loss of lipid species. Lipid class specific non-endogenous lipids, when applicable, were used as internal standards to gain highest precision in identification (minimizing false positives) and quantification of monitored molecular lipid species. In this way absolute or semi-absolute amounts of endogenous molecular lipids were determined with the highest precision that can be achieved with today's technologies. The endogenous lipids and respective standards were monitored at the molecular lipid level. In this way, not only false positive identifications were minimized, but molecular lipids could be precisely determined and quantified. Analysis quality was strictly controlled using a novel quality control system. This was mainly controlled by multiple internal standards (IS), external standards (ES), IS/ES ratios, and instrument control samples. By stringently controlling these components, technical and biological outliers were readily identified and rejected from further analysis. To obtain best precision in sensitivity, selectivity and quantification for each molecular lipid different targeted platforms were used. Some lipids are best analyzed using high performance liquid chromatography (HPLC) or ultra high performance liquid chromatography (UHPLC) combined with mass spectrometry based multiple reaction monitoring (MRM) whereas others are best analyzed by direct infusion in combination with mass spectrometry-based precursor ion scanning and neutral loss scanning techniques.

SUMMARY OF THE INVENTION

The present invention provides novel lipidomic markers for predicting and preventing severe CVD/CAD-associated complications, including AMI and death. These markers thus provide a means to identify and treat high-risk coronary artery disease patients. Specifically, it has been found that the lipid molecules, lipid-lipid ratios and lipid-clinical concentration ratios provided herein, when displaying an increased or decreased level—as the case may be—in samples from CAD patients, are useful lipidomic markers for the methods and uses in accordance with the present invention. These sensitive and specific markers were specifically tested to display superior diagnostic and prognostic value compared to the current clinically-used markers predictive for CVD/CAD outcomes. In fact, the currently available biomarkers such as LDL-C or HDL-C have only very limited or no value in predicting the CVD death risk in CAD patients. The present invention therefore represents a significant advantage to other markers which are currently used to diagnose and/or predict CVD and CVD complications, which include LDL-C, total plasma/serum cholesterol and Apolipoprotein B and A1. Thus, the lipidomic markers provided herein allow better diagnosis of or assessment of the risk to develop major CVD complications such as AMI or CVD death.

In accordance with the present invention, methods are inter alia disclosed herein for determining the risk of a patient to develop CVD complications, determining warning signs of CVD risks, (including death, myocardial infarction (MI), angina pectoris, transischemic attack (TIA) and stroke) in said patient.

Methods according to the invention typically comprise the steps of: a) providing a biological sample from a CAD subject; b) determining a lipid concentration, lipid-lipid ratio, or lipid-clinical concentration ratio or (a) corresponding profile(s) from said sample (i.e., determining information on a lipidomic marker in accordance with the invention); and c) comparing said determined lipid concentration, lipid-lipid ratio, or lipid-clinical concentration ratio or said corresponding profile(s) to the corresponding lipid concentration, lipid-lipid ratio, or lipid-clinical concentration ratio or the corresponding profile(s) in a control.

The control may be a sample from (a) CAD patient(s) with no history of major CVD events. It may also be a sample that represents a combination of samples from a CAD patient population with no history of major CVD events. Alternatively, the control may be a set of data concerning a lipidomic marker in accordance with the present invention, e.g., information on the concentration of (a) lipid(s), lipid-lipid ratio(s), or lipid-clinical concentration ratio(s) in accordance with the present invention in a sample when taken from (a) CAD patient(s) with no history of major CVD events, or in a combination of samples taken from a CAD patient population with no history of major CVD events. Said information, and thus the corresponding set of data, may have been previously determined, calculated or extrapolated, or may have yet to be determined, calculated or extrapolated, or may also be taken from the literature.

As mentioned above, the lipidomic marker to be compared between the subject sample and the control (or control sample) may be one or more of the lipid concentration(s), lipid-lipid ratio(s), or lipid-clinical concentration ratio(s) or combinations thereof, i.e., the corresponding profile(s), as described and claimed herein. In this regard, the control or control sample allows establishment of the lipidomic marker baseline or starting point.

In connection with all aspects and embodiments of the invention described and claimed herein, the determination of the lipid concentration(s), the lipid-lipid ratio(s) or the lipid-clinical concentration ratio(s) is typically performed using an assay. Collecting information on a lipidomic marker (i.e., the concentration(s) of (a) lipid(s), lipid-lipid ratio(s), or lipid-clinical concentration ratio(s) or combinations thereof, i.e., corresponding profile(s)) from the sample of a patient and, where appropriate, a corresponding control sample, can be performed with various chemical and high-resolution analytical techniques. Suitable analytical techniques include, but are not limited to, mass spectrometry and nuclear resonance spectroscopy. Any high-resolution technique capable of resolving individual lipids or lipid classes and providing structural information of the same can be used to collect the information on the lipidomic marker in question, e.g., lipid profile from the biological sample. Collecting the information on the lipidomic marker with mass spectrometry (MS) is one of the preferred embodiments of the current invention. The MS instrument can be coupled to a direct sample infusion method, such as a robotic nanoflow ion source device, or to a high performance separation method such as high performance liquid chromatography (HPLC) or ultra performance liquid chromatography (UPLC).

Again in accordance with all aspects and embodiments described and claimed herein, both the sample from the subject and the control sample is preferably a blood sample, more preferably a blood plasma sample, or also preferably a blood serum sample. It may also be a fraction of blood, blood plasma or blood serum, e.g., a lipoprotein fraction. A blood sample can be prepared and plasma or serum, or fractions thereof, can be separated therefrom with techniques well known to the person skilled in the art. Alternatively, both the sample from the subject and the control sample may also be a tissue sample, e.g., artery tissue, such as carotid artery tissue, or artery plaque material, such as carotid artery plaque material.

The lipidomic markers of the present invention allow for prediction and prevention of fatal CVD complications. This will facilitate earlier intervention, less symptom development and suffering and decreased morbidity/mortality associated with CVD. Thus, the lipidomic markers described and claimed herein allow for individual tailoring of drug intervention for patients being at risk to develop major CVD complications.

In other words, the present invention discloses diagnostic and/or predictive lipid markers and lipid-lipid or lipid-clinical concentration ratios for use in predicting CVD complications such as AMI or CVD death. The invention uses the measurement of lipid concentrations, lipid-lipid and/or lipid-clinical concentration ratios to determine the risk of said subject to develop CVD complications such as AMI and/or CVD death. The subject may have previously suffered from a cardiovascular disease event such as angina pectoris, myocardial infarction or stroke. The CVD may or may not be a result of atherosclerosis.

Claim 1 (note claims only have preferred embodiments) Accordingly, in one aspect of the invention, a method is provided for determining whether a subject is at risk to develop one or more CVD complications, such as AMI or CVD death, said method comprising determining in a sample from said subject the concentration(s) of one or more lipid(s), wherein (an) increased or decreased concentration(s) in said sample, when compared to a control sample, is (are) indicative of said subject having an increased risk of developing one or more CVD complications, such as AMI or CVD death, wherein the one or more lipid(s) whose increase(s) in concentration is (are) compared to the control is (are) selected from (Tables 4a and 7a):

Cer(d18:1/18:0), Cer(d18:1/20:0), Cer(d18:1/24:1), GlcCer(d18:1/18:0), LacCer(d18:1/18:0), LacCer(d18:1/20:0), LacCer(d18:1/22:0), LacCer(d18:1/24:0), PC O-32:0 (KDdiA-PC), PS O-16:0/18:2-alkenyl, PS O-16:1/18:2-alkyl, PS O-18:0/18:2-alkenyl (PS O-18:1/18:2-alkyl), PS O-18:2/16:0-alkenyl and Total LacCer; and wherein the one or more lipid(s) whose decrease(s) in concentration is (are) compared to the control is (are) selected from (Tables 4a and 7a):

CE 14:0, CE 16:0, CE 17:1, CE 20:3, Cer(d18:0/22:0), Cer(d18:0/24:0), LPC 18:1, PC 16:0/18:2, PC 16:0/20:3, PC 16:0/20:4, PC 16:0/22:6, PC 18:0/18:1, PC 18:0/20:3, PC 18:0/20:4, PC 18:1/18:2, SM (d18:1/14:0) (d18:1/13:1-OH), SM (d18:1/23:0) (d18:1/22:1-OH), SM (d18:1/24:0) (d18:1/23:1-OH), Total CE, Total LPC and Total PC.

In a particular embodiment, a method is provided for determining whether a subject is at risk to develop one or more CVD complications, such as AMI or CVD death, wherein the subject is not undergoing statin treatment and wherein said method comprises determining in a sample from said subject the concentration(s) of one or more lipid(s), wherein (an) increased or decreased concentration(s) in said sample, when compared to a control sample, is (are) indicative of said subject having an increased risk of developing one or more CVD complications, such as AMI or CVD death, and wherein the one or more lipid(s) whose increase in concentration is (are) compared to the control is (are) selected from (Tables 4b and 7b):

Cer(d18:1/16:0), Cer(d18:1/18:0), Cer(d18:1/20:0), Cer (d18:1/22:0), Cer(d18:1/24:1), Cer(d18:1/26:1), GlcCer(d18:1/18:0), GlcCer(d18:1/20:0), GlcCer(d18:1/24:1), GlcCer(d18:1/26:1), LacCer(d18:1/18:0), LacCer(d18:1/20:0), LacCer(d18:1/22:0), LacCer(d18:1/24:0), LacCer(d18:1/24:1), PC O-32:0 (KDdiA-PC), PS O-16:0/18:2-alkenyl, PS O-16:1/18:2-alkyl, PS O-18:2/16:0-alkenyl, Total Cer, Total DAG and Total LacCer;

and wherein the one or more lipid(s) whose decrease(s) in concentration is (are) compared to the control is (are) selected from (Tables 4b and 7b):

CE 14:0, CE 17:1, CE 20:3, Cer(d18:0/24:0), LPC 18:1, PC 16:0/20:3, PC 16:0/20:4, PC 18:0/20:4, PC O-40:3, SM (d18:1/14:0) (d18:1/13:1-OH), Total LPC and Total PC.

In a preferred embodiment (for subjects that are either undergoing or not undergoing statin treatment), the one or more lipid(s) whose increase(s) in concentration is (are) compared to the control is (are) selected from (Table 10):

Cer(d18:1/20:0), LacCer(d18:1/20:0), Cer(d18:1/24:1), LacCer(d18:1/24:1), PS O-18:2/16:0-alkenyl, PS O-16:1/18:2-alkyl, Total Cer, Total LacCer, GlcCer(d18:1/24:1), LacCer(d18:1/22:0) and Cer(d18:1/18:0).

In another preferred embodiment, the one or more lipid(s) whose decrease(s) in concentration is (are) compared to the control is (are) selected from (Table 10):

Total PC, PC 16:0/20:4, Cer(d18:0/24:0), Total LPC, CE 14:0, CE 20:3, CE 17:1, PC 16:0/20:3, LPC 18:1, PC 18:0/20:3, PC 18:0/18:1 and Cer(d18:0/22:0).

In a particularly preferred embodiment, the one or more lipid(s) whose increase(s) in concentration is (are) compared to the control is (are) selected from (Table 13):

Cer(d18:1/20:0), LacCer(d18:1/20:0), Cer(d18:1/24:1), LacCer(d18:1/24:1), LacCer(d18:1/22:0) and Cer(d18:1/18:0).

In another particularly preferred embodiment, the one or more lipid(s) whose decrease(s) in concentration is (are) compared to the control is (are) selected from (Table 13):

PC 16:0/20:4 and Cer(d18:0/24:0).

In an alternative embodiment, the present invention relates to a method for determining whether a subject is at risk to develop one or more complications such as AMI or CVD death, comprising determining in a sample from said subject one or more lipid-lipid ratio(s), wherein (an) increased or decreased lipid-lipid ratio(s) in said sample, when compared to a control sample, is (are) indicative of said subject having an increased risk of developing one or more CVD complications, such as AMI or CVD death, wherein the one or more lipid-lipid ratio(s) whose increase(s) is (are) compared to the control is (are) selected from (Tables 5a and 8a):

CE 16:0/CE 18:3, CE 18:2/CE 18:3, CE 19:1/Cer(d18:0/22:0), Cer(d18:1/16:0)/LPC 18:1, Cer(d18:1/16:0)/Total PC, Cer(d18:1/18:0)/LPC 16:0, Cer(d18:1/18:0)/LPC 18:1, Cer(d18:1/18:0)/PC 16:0/18:1, Cer(d18:1/18:0)/PC 16:0/20:3, Cer(d18:1/18:0)/PC 16:0/20:4, Cer (d18:1/18:0)/PC 18:0/20:4, Cer(d18:1/18:0)/Total LPC, Cer(d18:1/18:0)/Total PC, Cer(d18:1/20:0)/PC 16:0/18:1, Cer(d18:1/20:0)/PC 16:0/20:3, Cer(d18:1/20:0)/PC 16:0/20:4, Cer(d18:1/20:0)/PC 18:0/20:4, Cer (d18:1/20:0)/PC 18:1/18:1, Cer(d18:1/20:0)/Total PC, Cer(d18:1/22:0)/LPC 18:2, Cer(d18:1/22:0)/PC 16:0/20:3, Cer(d18:1/22:0)/PC 16:0/20:4, Cer(d18:1/22:0)/Total PC, Cer(d18:1/24:1)/LPC 18:1, Cer(d18:1/24:1)/LPC 18:2, Cer(d18:1/24:1)/PC 16:0/18:1, Cer(d18:1/24:1)/PC 16:0/20:3, Cer(d18:1/24:1)/PC 16:0/20:4, Cer (d18:1/24:1)/PC 18:0/18:1, Cer(d18:1/24:1)/PC 18:0/20:3, Cer(d18:1/24:1)/PC 18:0/20:4, Cer(d18:1/24:1)/SM (d18:1/24:0) (d18:1/23:1-OH), Cer(d18:1/24:1)/

Total CE, Cer(d18:1/24:1)/Total LPC, Cer(d18:1/24:1)/ Total PC, Cer(d18:1/26:0)/PC O-40:0, GlcCer(d18:1/ 20:0)/PC 16:0/20:4, GlcCer(d18:1/20:0)/Total PC, Glc- Cer(d18:1/26:0)/Total CE, LacCer(d18:1/16:0)/Total LPC, LacCer(d18:1/18:0)/PC 16:0/18:1, LacCer(d18: 1/18:0)/PC 16:0/20:3, LacCer(d18:1/18:0)/PC 18:0/18: 1, LacCer(d18:1/18:0)/PC 18:0/20:3, LacCer(d18:1/18: 0)/PC 18:1/18:1, LacCer(d18:1/18:0)/PC 18:1/18:2, LacCer(d18:118:0)/Total LPC, LacCer(d18:1/18:0)/ Total PC, LacCer(d18:1/20:0)/PC 16:0/18:1, LacCer (d18:1/20:0)/PC 16:0/20:3, LacCer(d18:1/20:0)/PC 18:0/18:1, LacCer(d18:1/20:0)/PC 18:0/20:3 LacCer (d18:1/20:0)/PC 18:1/18:1, LacCer(d18:1/20:0)/PC 18:1/18:2, LacCer(d18:1/20:0)/PC 18:2/18:2, LacCer (d18:1/20:0)/SM (d18:1/17:1-OH), LacCer(d18:1/20: 0)/SM (d18:1/18:0), LacCer(d18:1/20:0)/Total LPC, LacCer(d18:1/20:0)/Total PC, LacCer(d18:1/20:0)/Total SM, LacCer(d18:1/22:0)/PC 16:0/20:3, LacCer (d18:1/22:0)/PC 16:0/20:4, LacCer(d18:1/22:0)/PC 18:0/20:3, LacCer(d18:1/22:0)/SM (d18:1/14:0) (d18: 1/13:1-OH), LacCer(d18:1/22:0)/Total LPC, LacCer (d18:1/22:0)/Total PC, LacCer(d18:1/24:0)/PC 16:0/ 20:3, LacCer(d18:1/24:0)/Total LPC, LacCer(d18:1/ 24:1)/Total LPC, LacCer(d18:1/24:1)/Total PC, LacCer (d18:1/24:1)/Total PC O, PC 16:0/16:0/PC 16:0/20:4, PC 16:0/16:0/Total PC, PC 16:0/18:2/Total PC, PC O-18:0/18:2-alkyl/PC O-36:5, PC O-32:0 (KDdiA-PC)/PC O-38:5, PS O-16:0/18:2-alkenyl/Total PS O, PS O-16:1/18:2-alkyl/Total PS O, PS O-18:0/18:2-alkenyl (PS O-18:1/18:2-alkyl)/Total PS O, PS O-18: 2/16:0-alkenyl/Total PS O, Total Cer/Total PC, Total LacCer/Total PC and Total LacCer/Total PC O;

and wherein the one or more lipid-lipid ratio(s) whose decrease(s) is (are) compared to the control is (are) selected from (Tables 5a and 8a):

CE 14:0/Cer(d18:1/24:1), CE 16:0/Cer(d18:1/24:1), CE 16:1/CE 19:1, CE 16:1/Cer(d18:1/18:0), CE 16:1/Cer (d18:1/20:0), CE 16:1/Cer(d18:1/24:1), CE 16:1/Glc-Cer(d18:1/18:0), CE 16:1/GlcCer(d18:1/20:0), CE 16:1/LacCer(d18:1/16:0), CE 16:1/LacCer(d18:1/18: 0), CE 16:1/LacCer(d18:1/20:0), CE 16:1/LacCer(d18: 1/22:0), CE 16:1/LacCer(d18:1/24:0), CE 16:1/PC 16:0/16:0, CE 16:1/Total LacCer, CE 17:1/Cer(d18:1/ 24:1), CE 17:1/GlcCer(d18:1/24:1), CE 17:1/LacCer (d18:1/18:0), CE 18:1/Total LacCer, CE 18:3/Cer(d18: 1/16:0), CE 18:3/Cer(d18:1/18:0), CE 18:3/Cer(d18:1/ 20:0), CE 18:3/Cer(d18:1/22:0), CE 18:3/Cer(d18:1/ 24:0), CE 18:3/Cer(d18:1/24:1), CE 18:3/GlcCer(d18: 1/18:0), CE 18:3/GlcCer(d18:1/20:0), CE 18:3/LacCer (d18:1/18:0), CE 18:3/LacCer(d18:1/20:0), CE 18:3/ LacCer(d18:1/22:0), CE 18:3/LacCer(d18:1/24:0), CE 18:3/PC 16:0/16:0, CE 18:3/PC O-34:1, CE 18:3/PS O-16:0/18:1-alkenyl (PS O-16:1/18:1-alkyl), CE 18:3/ PS O-16:0/18:2-alkenyl, CE 18:3/PS O-16:1/18:2-alkyl, CE 18:3/Total CE, CE 18:3/Total Cer, CE 18:3/ Total LacCer, CE 20:3/Cer(d18:1/24:1), CE 20:3/ LacCer(d18:1/20:0), Cer(d18:0/22:0)/Cer(d18:1/18:0), Cer(d18:0/22:0)/Cer(d18:1/20:0), Cer(d18:0/22:0)/Cer (d18:1/22:0), Cer(d18:0/22:0)/Cer(d18:1/24:1), Cer (d18:0/22:0)/LacCer(d18:1/24:0), Cer(d18:0/22:0)/PS O-16:0/18:2-alkenyl, Cer(d18:0/22:0)/PS O-16:1/18:2-alkyl, Cer(d18:0/22:0)/Total CE, Cer(d18:0/24:0)/Cer (d18:1/16:0), Cer(d18:0/24:0)/Cer(d18:1/18:0), Cer (d18:0/24:0)/Cer(d18:1/20:0), Cer(d18:0/24:0)/Cer (d18:1/22:0), Cer(d18:0/24:0)/Cer(d18:1/24:1), Cer (d18:0/24:0)/GlcCer(d18:1/20:0), Cer(d18:0/24:0)/ LacCer(d18:1/24:0), Cer(d18:0/24:0)/PS O-16:0/18:2-alkenyl, Cer(d18:0/24:0)/PS O-16:1/18:2-alkyl, Cer (d18:0/24:0)/SM (d18:1/17:0) (d18:1/16:1-OH), Cer (d18:0/24:0)/Total CE, Cer(d18:0/24:0)/Total Cer, Cer (d18:0/24:1)/Total CE, GlcCer(d18:1/26:0)/LacCer (d18:1/20:0), GlcCer(d18:1/26:0)/LacCer(d18:1/22:0), LPC 16:0/LacCer(d18:1/20:0), LPC 16:0/LacCer(d18: 1/22:0), LPC 16:0/LacCer(d18:1/24:1), LPC 16:0/Total LacCer, LPC 18:1/LacCer(d18:1/20:0), LPC 18:2/LacCer(d18:1/20:0), LPC 18:2/PS O-16:0/18:2-alkenyl, LPC 18:2/PS O-16:1/18:2-alkyl, PC 16:0/20:3/PS O-16:0/18:2-alkenyl, PC 16:0/20:3/PS O-16:1/18:2-alkyl, PC 18:1/18:2/PS O-16:0/18:2-alkenyl, PC 18:1/18: 2/PS O-16:1/18:2-alkyl, SM (d18:1/24:0) (d18:1/23:1-OH)/Total Cer and Total LPC/Total LacCer.

In an alternative embodiment, the present invention relates to a method for determining whether a subject is at risk to develop one or more complications such as AMI or CVD death, wherein the subject is not undergoing statin treatment and wherein said method comprises determining in a sample from said subject one or more lipid-lipid ratio(s), wherein (an) increased or decreased lipid-lipid ratio(s) in said sample, when compared to a control sample, is (are) indicative of said subject having an increased risk of developing one or more CVD complications, such as AMI or CVD death, wherein the one or more lipid-lipid ratio(s) whose increase(s) is (are) compared to the control is (are) selected from (Tables 5b and 8b):

CE 16:0/CE 18:3, CE 18:0/CE 18:3, CE 18:2/CE 18:3, Cer(d18:1/16:0)/LPC 18:1, Cer(d18:1/16:0)/Total PC, Cer(d18:1/18:0)/LPC 18:1, Cer(d18:1/18:0)/PC 16:0/ 18:1, Cer(d18:1/18:0)/PC 16:0/20:3, Cer(d18:1/18:0)/ PC 16:0/20:4, Cer(d18:1/18:0)/PC 18:0/18:1, Cer(d18: 1/18:0)/PC 18:0/20:4, Cer(d18:1/18:0)/PC 18:1/18:1, Cer(d18:1/18:0)/SM (d18:1/14:0) (d18:1/13:1-OH), Cer(d18:1/18:0)/SM (d18:1/17:2-OH), Cer(d18:1/18: 0)/SM (d18:1/18:1), Cer(d18:1/18:0)/Total CE, Cer (d18:1/18:0)/Total LPC, Cer(d18:1/18:0)/Total PC, Cer (d18:1/20:0)/PC 16:0/18:1, Cer(d18:1/20:0)/PC 16:0/ 20:3, Cer(d18:1/20:0)/PC 16:0/20:4, Cer(d18:1/20:0)/ PC 18:0/18:1, Cer(d18:1/20:0)/PC 18:0/20:4, Cer(d18: 1/20:0)/PC 18:1/18:1, Cer(d18:1/20:0)/SM (d18:1/14: 0) (d18:1/13:1-OH), Cer(d18:1/20:0)/Total LPC, Cer (d18:1/20:0)/Total PC, Cer(d18:1/20:0)/Total PC O, Cer(d18:1/22:0)/LPC 18:2, Cer(d18:1/22:0)/PC 16:0/ 20:3, Cer(d18:1/22:0)/PC 16:0/20:4, Cer(d18:1/22:0)/ PC 18:0/20:4, Cer(d18:1/22:0)/Total PC, Cer(d18:1/24: 1)/LPC 18:1, Cer(d18:1/24:1)/LPC 18:2, Cer(d18:1/24: 1)/PC 16:0/18:1, Cer(d18:1/24:1)/PC 16:0/18:2, Cer (d18:1/24:1)/PC 16:0/20:3, Cer(d18:1/24:1)/PC 16:0/ 20:4, Cer(d18:1/24:1)/PC 18:0/18:1, Cer(d18:1/24:1)/ PC 18:0/18:2, Cer(d18:1/24:1)/PC 18:0/20:3, Cer(d18: 1/24:1)/PC 18:0/20:4, Cer(d18:1/24:1)/PC 18:1/18:1, Cer(d18:1/24:1)/PC 18:1/18:2, Cer(d18:1/24:1)/PC O-40:3, Cer(d18:1/24:1)/SM (d18:1/17:1-OH), Cer (d18:1/24:1)/SM (d18:1/18:0), Cer(d18:1/24:1)/SM (d18:1/23:0) (d18:1/22:1-OH), Cer(d18:1/24:1)/SM (d18:1/24:0) (d18:1/23:1-OH), Cer(d18:1/24:1)/Total CE, Cer(d18:1/24:1)/Total LPC, Cer(d18:1/24:1)/Total PC, GlcCer(d18:1/26:0)/Total CE, GlcCer(d18:1/26:1)/ Total CE, LacCer(d18:1/18:0)/Total PC, LacCer(d18: 1/20:0)/PC 16:0/20:3, LacCer(d18:1/20:0)/PC 16:0/20: 4, LacCer(d18:1/20:0)/PC 18:0/18:1, LacCer(d18:1/20: 0)/PC 18:0/20:3, LacCer(d18:1/20:0)/PC 18:0/20:4, LacCer(d18:1/20:0)/PC 18:1/18:2, LacCer(d18:1/20: 0)/SM (d18:1/17:1-OH), LacCer(d18:1/20:0)/SM (d18: 1/18:0), LacCer(d18:1/20:0)/Total CE, LacCer(d18:1/ 20:0)/Total LPC, LacCer(d18:1/20:0)/Total PC, LacCer (d18:1/20:0)/Total SM, LacCer(d18:1/24:0)/Total LPC, PC 16:0/16:0/PC 16:0/20:4, PC 16:0/16:0/Total PC, PC O-32:0 (KDdiA-PC)/Total PC O, PS O-16:0/18:2-alkenyl/Total PC, PS O-16:0/18:2-alkenyl/Total PC O, PS O-16:0/18:2-alkenyl/Total PS O, PS O-16:1/18:2-alkyl/ Total PC, PS O-16:1/18:2-alkyl/Total PC O, PS O-16:1/18:2-alkyl/Total PS O, PS O-18:2/16:0-alkenyl/Total PC O, PS O-18:2/16:0-alkenyl/Total PS O, SM (d18:1/17:0) (d18:1/16:1-OH)/Total PC O, Total Cer/Total PC, Total DAG/Total LPC, Total DAG/Total PC, Total DAG/Total PC O and Total LacCer/Total PC;

and wherein the one or more lipid-lipid ratio(s) whose decrease(s) is (are) compared to the control is (are) selected from (Tables 5b and 8b):

CE 14:0/Cer(d18:1/18:0), CE 14:0/Cer(d18:1/24:1), CE 14:0/Total DAG, CE 15:0/Cer(d18:1/20:0), CE 16:0/Cer(d18:1/18:0), CE 16:0/Cer(d18:1/24:1), CE 16:1/CE 19:1, CE 16:1/Cer(d18:1/18:0), CE 16:1/Cer(d18:1/20:0), CE 16:1/Cer(d18:1/24:1), CE 16:1/GlcCer(d18:1/24:1), CE 16:1/LacCer(d18:1/18:0), CE 16:1/LacCer(d18:1/24:0), CE 16:1/Total LacCer, CE 17:1/Cer(d18:1/18:0), CE 17:1/Cer(d18:1/24:1), CE 18:2/Cer(d18:1/20:0), CE 18:2/Cer(d18:1/24:1), CE 18:3/Cer(d18:1/16:0), CE 18:3/Cer(d18:1/18:0), CE 18:3/Cer(d18:1/20:0), CE 18:3/Cer(d18:1/22:0), CE 18:3/Cer(d18:1/24:0), CE 18:3/Cer(d18:1/24:1), CE 18:3/GlcCer(d18:1/20:0), CE 18:3/LacCer(d18:1/20:0), CE 18:3/LacCer(d18:1/22:0), CE 18:3/LacCer(d18:1/24:0), CE 18:3/PC 16:0/16:0, CE 18:3/PC O-34:1, CE 18:3/PS O-16:0/18:2-alkenyl, CE 18:3/PS O-16:1/18:2-alkyl, CE 18:3/Total CE, CE 18:3/Total Cer, CE 18:3/Total DAG, CE 18:3/Total LacCer, CE 20:3/Cer(d18:1/24:1), CE 20:3/LacCer(d18:1/20:0), CE 20:4/Cer(d18:1/18:0), CE 20:4/Cer(d18:1/24:1), CE 20:4/GlcCer(d18:1/20:0), CE 20:4/GlcCer(d18:1/24:1), CE 20:4/LacCer(d18:1/20:0), CE 20:5/LacCer(d18:1/20:0), Cer(d18:0/22:0)/Cer(d18:1/18:0), Cer(d18:0/22:0)/Cer(d18:1/20:0), Cer(d18:0/22:0)/Cer(d18:1/24:1), Cer(d18:0/22:0)/PS O-16:0/18:2-alkenyl, Cer(d18:0/22:0)/PS O-16:1/18:2-alkyl, Cer(d18:0/22:0)/Total CE, Cer(d18:0/22:0)/Total DAG, Cer(d18:0/22:0)/Total GlcCer, Cer(d18:0/24:0)/Cer(d18:1/18:0), Cer(d18:0/24:0)/Cer(d18:1/20:0), Cer(d18:0/24:0)/Cer(d18:1/24:1), Cer(d18:0/24:0)/PS O-16:0/18:2-alkenyl, Cer(d18:0/24:0)/PS O-16:1/18:2-alkyl, Cer(d18:0/24:0)/Total CE, Cer(d18:0/24:0)/Total Cer, DAG 16:0/18:1/Total DAG, GlcCer(d18:1/26:0)/LacCer(d18:1/20:0), LPC 16:0/LacCer(d18:1/24:0), LPC 18:1/LacCer(d18:1/20:0), LPC 18:2/LacCer(d18:1/20:0), PC 16:0/20:3/PS O-16:0/18:2-alkenyl, PC 16:0/20:3/PS O-16:1/18:2-alkyl, PC 16:0/20:4/PS O-16:0/18:2-alkenyl, PC 16:0/20:4/PS O-16:1/18:2-alkyl, PC 16:0/20:4/Total DAG, PC 18:0/20:3/PS O-16:0/18:2-alkenyl, PC 18:0/20:3/PS O-16:1/18:2-alkyl, PC 18:0/20:3/PS O-18:2/16:0-alkenyl, PC 18:0/20:4/PS O-16:0/18:2-alkenyl, PC 18:0/20:4/PS O-16:1/18:2-alkyl, PC 18:1/18:2/PS O-16:0/18:2-alkenyl, PC 18:1/18:2/PS O-16:1/18:2-alkyl, PC 18:1/18:2/Total Cer, PC O-40:3/PS O-18:2/16:0-alkenyl, SM (d18:1/23:0) (d18:1/22:1-OH)/Total DAG, SM (d18:1/24:0) (d18:1/23:1-OH)/Total Cer, Total CE/Total DAG and Total LPC/Total LacCer.

In a preferred embodiment (for subjects that are either undergoing or not undergoing statin treatment), the one or more lipid-lipid ratio(s) whose increase is (are) compared to the control is (are) selected from (Table 11):

GlcCer(d18:1/26:1)/Total CE, Cer(d18:1/24:1)/Total PC, Cer(d18:1/24:1)/PC 16:0/20:4, Cer(d18:1/20:0)/PC 16:0/20:4, LacCer(d18:1/20:0)/PC 16:0/20:3, Total Cer/Total PC, Total LacCer/Total PC, LacCer(d18:1/20:0)/PC 18:1/18:2, PS O-16:0/18:2-alkenyl/Total PS O, Cer(d18:1/18:0)/PC 16:0/20:4, LacCer(d18:1/20:0)/Total LPC and LacCer(d18:1/20:0)/PC 16:0/20:4;

In another preferred embodiment, the one or more lipid-lipid ratio(s) whose decrease is (are) compared to the control is (are) selected from (Table 11):

Cer(d18:0/24:0)/Cer(d18:1/24:1), Cer(d18:0/22:0)/Cer(d18:1/24:1), DAG 16:0/18:1/Total DAG, Cer(d18:0/24:0)/Cer(d18:1/22:0), Cer(d18:0/24:0)/Total CE, Cer(d18:0/24:0)/Cer(d18:1/24:1), Cer(d18:0/24:0)/Total Cer, Cer(d18:0/24:0)/Cer(d18:1/18:0), Cer(d18:0/24:0)/PS O-16:0/18:2-alkenyl, Cer(d18:0/24:0)/LacCer(d18:1/24:0), Cer(d18:0/22:0)/Cer(d18:1/18:0), Cer(d18:0/24:0)/Cer(d18:1/22:0), Cer(d18:0/22:0)/Cer(d18:1/20:0), Cer(d18:0/22:0)/PS O-16:0/18:2-alkenyl, Cer(d18:0/22:0)/PS O-16:1/18:2-alkyl, GlcCer(d18:1/26:0)/LacCer(d18:1/20:0), Total LPC/Total LacCer and GlcCer(d18:1/26:0)/LacCer(d18:1/22:0).

In a particularly preferred embodiment, the one or more lipid-lipid ratio(s) whose increase is (are) compared to the control is (are) selected from (Table 13):

Cer(d18:1/24:1)/PC 16:0/20:4, LacCer(d18:1/20:0)/PC 16:0/20:3, PS O-16:0/18:2-alkenyl/Total PS O and Cer(d18:1/18:0)/PC 16:0/20:4;

and the one or more lipid-lipid ratio(s) whose decrease is (are) compared to the control is (are) selected from (Table 13):

GlcCer(d18:1/26:0)/LacCer(d18:1/20:0), DAG 16:0/18:1/Total DAG, Cer(d18:0/24:0)/Total Cer, Total LPC/Total LacCer, GlcCer(d18:1/26:0)/LacCer(d18:1/22:0), Cer(d18:0/24:0)/Cer(d18:1/24:1), Cer(d18:0/24:0)/Cer(d18:1/18:0), Cer(d18:0/24:0)/PS O-16:0/18:2-alkenyl, Cer(d18:0/24:0)/Cer(d18:1/22:0), Cer(d18:0/22:0)/PS O-16:0/18:2-alkenyl, Cer(d18:0/22:0)/PS O-16:1/18:2-alkyl and Cer(d18:0/24:0)/LacCer(d18:1/24:0);

In yet another alternative embodiment the present invention relates to a method for determining whether a subject is at risk to develop one or more CVD complications, such as AMI or CVD death, comprising determining in a sample from said subject one or more lipid-clinical concentration ratio(s), wherein (an) increased or decreased lipid-clinical concentration ratio(s) in said sample, when compared to a control sample, is (are) indicative of said subject having an increased risk of developing one or more CVD complications, such as AMI or CVD death, wherein the one or more lipid-clinical concentration ratio(s) whose increase is (are) compared to the control is (are) selected from (Tables 6a and 9a):

Cer(d18:1/16:0)/triglycerides (EDTA) (mg/dL), Cer(d18:1/18:0)/apolipoprotein A-I (mg/dL), Cer(d18:1/18:0)/apolipoprotein B (mg/dL), Cer(d18:1/18:0)/HDL cholesterol (EDTA) (mg/dL), Cer(d18:1/18:0)/total cholesterol (EDTA) (mg/dL), Cer(d18:1/18:0)/total-c/HDL-c, Cer(d18:1/18:0)/triglycerides (EDTA) (mg/dL), Cer(d18:1/20:0)/apolipoprotein A-I (mg/dL), Cer(d18:1/20:0)/apolipoprotein B (mg/dL), Cer(d18:1/20:0)/HDL cholesterol (EDTA) (mg/dL), Cer(d18:1/20:0)/total cholesterol (EDTA) (mg/dL), Cer(d18:1/20:0)/triglycerides (EDTA) (mg/dL), Cer(d18:1/22:0)/apolipoprotein B (mg/dL), Cer(d18:1/22:0)/LDL cholesterol (EDTA) (mg/dL), Cer(d18:1/22:0)/triglycerides (EDTA) (mg/dL), Cer(d18:1/24:1)/apolipoprotein A-I (mg/dL), Cer(d18:1/24:1)/apolipoprotein B (mg/dL), Cer(d18:1/24:1)/LDL cholesterol (EDTA) (mg/dL), Cer(d18:1/24:1)/total cholesterol (EDTA)

(mg/dL), Cer(d18:1/24:1)/total-c/HDL-c, Cer(d18:1/24:1)/triglycerides (EDTA) (mg/dL), GlcCer(d18:1/24:0)/total cholesterol (EDTA) (mg/dL), LacCer(d18:1/16:0)/triglycerides (EDTA) (mg/dL), LacCer(d18:1/18:0)/apolipoprotein A-I (mg/dL), LacCer(d18:1/18:0)/apolipoprotein B (mg/dL), LacCer(d18:1/18:0)/HDL cholesterol (EDTA) (mg/dL), LacCer(d18:1/18:0)/LDL cholesterol (EDTA) (mg/dL), LacCer(d18:1/18:0)/total cholesterol (EDTA) (mg/dL), LacCer(d18:1/18:0)/total-c/HDL-c, LacCer(d18:1/18:0)/triglycerides (EDTA) (mg/dL), LacCer(d18:1/20:0)/apoA1/apoB, LacCer(d18:1/20:0)/apolipoprotein A-I (mg/dL), LacCer(d18:1/20:0)/apolipoprotein B (mg/dL), LacCer(d18:1/20:0)/HDL cholesterol (EDTA) (mg/dL), LacCer(d18:1/20:0)/LDL cholesterol (EDTA) (mg/dL), LacCer(d18:1/20:0)/LDL-c/HDL-c, LacCer(d18:1/20:0)/total cholesterol (EDTA) (mg/dL), LacCer(d18:1/20:0)/total-c/HDL-c, LacCer(d18:1/20:0)/triglycerides (EDTA) (mg/dL), LacCer(d18:1/22:0)/apoA1/apoB, LacCer(d18:1/22:0)/apolipoprotein A-I (mg/dL), LacCer(d18:1/22:0)/apolipoprotein B (mg/dL), LacCer(d18:1/22:0)/HDL cholesterol (EDTA) (mg/dL), LacCer(d18:1/22:0)/LDL cholesterol (EDTA) (mg/dL), LacCer(d18:1/22:0)/total cholesterol (EDTA) (mg/dL), LacCer(d18:1/22:0)/total-c/HDL-c, LacCer(d18:1/22:0)/triglycerides (EDTA) (mg/dL), LacCer(d18:1/24:0)/apoA1/apoB, LacCer(d18:1/24:1)/apolipoprotein A-I (mg/dL), LacCer(d18:1/24:1)/apolipoprotein B (mg/dL), LacCer(d18:1/24:1)/total cholesterol (EDTA) (mg/dL), LacCer(d18:1/24:1)/triglycerides (EDTA) (mg/dL), PC O-32:0 (KDdiA-PC)/apolipoprotein A-I (mg/dL), P C O-32:0 (KDdiA-PC)/triglycerides (EDTA) (mg/dL), PC O-34:1/triglycerides (EDTA) (mg/dL), PS O-16:0/18:1-alkenyl (PS O-16:1/18:1-alkyl)/triglycerides (EDTA) (mg/dL), PS O-16:0/18:2-alkenyl/triglycerides (EDTA) (mg/dL), PS O-16:1/18:2-alkyl/triglycerides (EDTA) (mg/dL), PS O-18:2/16:0-alkenyl/HDL cholesterol (EDTA) (mg/dL), PS O-18:2/16:0-alkenyl/triglycerides (EDTA) (mg/dL), Total Cer/apolipoprotein A-I (mg/dL), Total Cer/total cholesterol (EDTA) (mg/dL), Total Cer/triglycerides (EDTA) (mg/dL), Total GlcCer/apolipoprotein B (mg/dL), Total GlcCer/total cholesterol (EDTA) (mg/dL), Total LacCer/apolipoprotein A-I (mg/dL), Total LacCer/apolipoprotein B (mg/dL), Total LacCer/total cholesterol (EDTA) (mg/dL) and Total LacCer/triglycerides (EDTA) (mg/dL);

and wherein the one or more lipid-clinical concentration ratio(s) whose decrease is (are) compared to the control is (are) selected from (Tables 6a and 9a):

CE 14:0/apolipoprotein B (mg/dL), CE 14:0/LDL cholesterol (EDTA) (mg/dL), CE 14:0/LDL-c/HDL-c, CE 14:0/total cholesterol (EDTA) (mg/dL), CE 14:0/total-c/HDL-c, CE 16:1/apolipoprotein B (mg/dL), CE 16:1/HDL cholesterol (EDTA) (mg/dL), CE 16:1/LDL cholesterol (EDTA) (mg/dL), CE 16:1/total cholesterol (EDTA) (mg/dL), CE 17:1/LDL-c/HDL-c, CE 18:3/apoA1/apoB, CE 18:3/apolipoprotein A-I (mg/dL), CE 18:3/apolipoprotein B (mg/dL), CE 18:3/HDL cholesterol (EDTA) (mg/dL), CE 18:3/LDL cholesterol (EDTA) (mg/dL), CE 18:3/LDL-c/HDL-c, CE 18:3/total cholesterol (EDTA) (mg/dL), CE 18:3/total-c/HDL-c, CE 20:3/apolipoprotein B (mg/dL), CE 20:3/LDL-c/HDL-c, CE 20:3/total-c/HDL-c, CE 20:5/apolipoprotein B (mg/dL), CE 20:5/HDL cholesterol (EDTA) (mg/dL), CE 20:5/LDL cholesterol (EDTA) (mg/dL), Cer(d18:0/22:0)/apolipoprotein B (mg/dL), Cer(d18:0/22:0)/LDL-c/HDL-c, Cer(d18:0/22:0)/total-c/HDL-c, Cer(d18:0/24:0)/apolipoprotein A-I (mg/dL), Cer(d18:0/24:0)/apolipoprotein B (mg/dL), Cer(d18:0/24:0)/HDL cholesterol (EDTA) (mg/dL), Cer(d18:0/24:0)/LDL cholesterol (EDTA) (mg/dL), Cer(d18:0/24:0)/LDL-c/HDL-c, Cer(d18:0/24:0)/total cholesterol (EDTA) (mg/dL), Cer(d18:0/24:0)/total-c/HDL-c, LPC 18:2/apoA1/apoB, LPC 18:2/apolipoprotein B (mg/dL), LPC 18:2/HDL cholesterol (EDTA) (mg/dL), LPC 18:2/LDL cholesterol (EDTA) (mg/dL), LPC 18:2/LDL-c/HDL-c, LPC 18:2/total cholesterol (EDTA) (mg/dL), PC 16:0/20:3/apolipoprotein B (mg/dL), PC 16:0/20:3/HDL cholesterol (EDTA) (mg/dL), PC 16:0/20:3/LDL-c/HDL-c, PC 16:0/20:3/total-c/HDL-c, PC 16:0/20:4/apolipoprotein A-I (mg/dL), PC 16:0/20:4/apolipoprotein B (mg/dL), PC 16:0/20:4/LDL cholesterol (EDTA) (mg/dL), PC 16:0/20:4/LDL-c/HDL-c, PC 16:0/20:4/total cholesterol (EDTA) (mg/dL), PC 16:0/20:4/total-c/HDL-c, PC 18:0/18:1/LDL-c/HDL-c, PC 18:0/20:3/LDL-c/HDL-c, PC 18:0/20:3/total-c/HDL-c, PC 18:0/20:4/apoA1/apoB, Total LPC/LDL-c/HDL-c, Total LPC/total-c/HDL-c, Total PC/apolipoprotein B (mg/dL), Total PC/LDL-c/HDL-c, Total PC/total cholesterol (EDTA) (mg/dL) and Total PC/total-c/HDL-c.

In yet another alternative embodiment the present invention relates to a method for determining whether a subject is at risk to develop one or more CVD complications, such as AMI or CVD death, wherein the subject is not undergoing statin treatment and wherein said method comprises determining in a sample from said subject one or more lipid-clinical concentration ratio(s), wherein (an) increased or decreased lipid-clinical concentration ratio(s) in said sample, when compared to a control sample, is (are) indicative of said subject having an increased risk of developing one or more of CVD complications, such as AMI or CVD death, wherein the one or more lipid-clinical concentration ratio(s) whose increase is (are) compared to the control is (are) selected from (Tables 6b and 9b):

Cer(d18:1/16:0)/apolipoprotein A-1 (mg/dL), Cer(d18:1/16:0)/LDL cholesterol (EDTA) (mg/dL), Cer(d18:1/16:0)/triglycerides (EDTA) (mg/dL), Cer(d18:1/18:0)/apolipoprotein A-I (mg/dL), Cer(d18:1/18:0)/apolipoprotein B (mg/dL), Cer(d18:1/18:0)/HDL cholesterol (EDTA) (mg/dL), Cer(d18:1/18:0)/total cholesterol (EDTA) (mg/dL), Cer(d18:1/18:0)/total-c/HDL-c, Cer(d18:1/18:0)/triglycerides (EDTA) (mg/dL), Cer(d18:1/20:0)/apolipoprotein A-I (mg/dL), Cer(d18:1/20:0)/apolipoprotein B (mg/dL), Cer(d18:1/20:0)/HDL cholesterol (EDTA) (mg/dL), Cer(d18:1/20:0)/LDL cholesterol (EDTA) (mg/dL), Cer(d18:1/20:0)/total cholesterol (EDTA) (mg/dL), Cer(d18:1/20:0)/total-c/HDL-c, Cer(d18:1/20:0)/triglycerides (EDTA) (mg/dL), Cer(d18:1/22:0)/apolipoprotein A-I (mg/dL), Cer(d18:1/22:0)/apolipoprotein B (mg/dL), Cer(d18:1/22:0)/LDL cholesterol (EDTA) (mg/dL), Cer(d18:1/22:0)/total cholesterol (EDTA) (mg/dL), Cer(d18:1/22:0)/triglycerides (EDTA) (mg/dL), Cer(d18:1/24:0)/apolipoprotein A-I (mg/dL), Cer(d18:1/24:0)/apolipoprotein B (mg/dL), Cer(d18:1/24:0)/LDL cholesterol (EDTA) (mg/dL), Cer(d18:1/24:0)/total cholesterol (EDTA) (mg/dL), Cer(d18:1/24:1)/apolipoprotein A-I (mg/dL), Cer(d18:1/24:1)/apolipoprotein B (mg/dL), Cer(d18:1/24:1)/HDL cholesterol (EDTA) (mg/dL), Cer(d18:1/24:1)/LDL cholesterol (EDTA) (mg/dL), Cer(d18:1/24:1)/LDL-c/HDL-c, Cer(d18:1/24:1)/total cholesterol (EDTA) (mg/dL), Cer(d18:1/24:

1)/total-c/HDL-c, Cer(d18:1/24:1)/triglycerides (EDTA) (mg/dL), GlcCer(d18:1/20:0)/apolipoprotein B (mg/dL), GlcCer(d18:1/20:0)/total cholesterol (EDTA) (mg/dL), GlcCer(d18:1/24:1)/apolipoprotein B (mg/dL), GlcCer(d18:1/26:1)/apolipoprotein A-I (mg/dL), LacCer(d18:1/116:0)/triglycerides (EDTA) (mg/dL), LacCer(d18:1/18:0)/apolipoprotein A-I (mg/dL), LacCer(d18:1/18:0)/apolipoprotein B (mg/dL), LacCer(d18:1/18:0)/total cholesterol (EDTA) (mg/dL), LacCer(d18:1/20:0)/apoA1/apoB, LacCer(d18:1/20:0)/apolipoprotein A-I (mg/dL), LacCer(d18:1/20:0)/apolipoprotein B (mg/dL), LacCer(d18:1/20:0)/HDL cholesterol (EDTA) (mg/dL), LacCer(d18:1/20:0)/LDL cholesterol (EDTA) (mg/dL), LacCer(d18:1/20:0)/LDL-c/HDL-c, LacCer(d18:1/20:0)/total cholesterol (EDTA) (mg/dL), LacCer(d18:1/20:0)/total-c/HDL-c, LacCer(d18:1/20:0)/triglycerides (EDTA) (mg/dL), LacCer(d18:1/22:0)/apoA1/apoB, LacCer(d18:1/22:0)/apolipoprotein A-1 (mg/dL), LacCer(d18:1/22:0)/apolipoprotein B (mg/dL), LacCer(d18:1/22:0)/HDL cholesterol (EDTA) (mg/dL), LacCer(d18:1/22:0)/LDL cholesterol (EDTA) (mg/dL), LacCer(d18:1/22:0)/total cholesterol (EDTA) (mg/dL), LacCer(d18:1/24:1)/apolipoprotein A-I (mg/dL), LacCer(d18:1/24:1)/apolipoprotein B (mg/dL), LacCer(d18:1/24:1)/total cholesterol (EDTA) (mg/dL), LacCer(d18:1/24:1)/triglycerides (EDTA) (mg/dL), PC O-34:1/apolipoprotein B (mg/dL), PS O-16:0/18:2-alkenyl/triglycerides (EDTA) (mg/dL), PS O-16:1/18:2-alkyl/triglycerides (EDTA) (mg/dL), Total Cer/apolipoprotein A-I (mg/dL), Total Cer/apolipoprotein B (mg/dL), Total Cer/LDL cholesterol (EDTA) (mg/dL), Total Cer/total cholesterol (EDTA) (mg/dL), Total DAG/apolipoprotein A-I (mg/dL), Total DAG/triglycerides (EDTA) (mg/dL), Total GlcCer/apolipoprotein B (mg/dL), Total LacCer/apolipoprotein A-I (mg/dL), Total LacCer/apolipoprotein B (mg/dL) and Total LacCer/total cholesterol (EDTA) (mg/dL).

and wherein the one or more lipid-clinical concentration ratio(s) whose decrease is (are) compared to the control is (are) selected from (Tables 6b and 9b):
CE 14:0/apoA1/apoB, CE 14:0/apolipoprotein B (mg/dL), CE 14:0/LDL-c/HDL-c, CE 14:0/total-c/HDL-c, CE 16:1/apoA1/apoB, CE 18:3/apoA1/apoB, CE 18:3/apolipoprotein A-I (mg/dL), CE 18:3/apolipoprotein B (mg/dL), CE 18:3/HDL cholesterol (EDTA) (mg/dL), CE 18:3/LDL cholesterol (EDTA) (mg/dL), CE 18:3/LDL-c/HDL-c, CE 18:3/total cholesterol (EDTA) (mg/dL), CE 18:3/total-c/HDL-c, CE 20:5/triglycerides (EDTA) (mg/dL), Cer(d18:0/24:0)/apolipoprotein B (mg/dL), Cer(d18:0/24:0)/total cholesterol (EDTA) (mg/dL), Cer(d18:0/24:0)/total-c/HDL-c, PC 18:0/20:4/apoA1/apoB, PC O-38:6/apolipoprotein A-I (mg/dL), Total LPC/apoA1/apoB and Total PC/apolipoprotein A-I (mg/dL).

In a preferred embodiment (for subjects that are either undergoing or not undergoing statin treatment), the one or more lipid-clinical concentration ratio(s) whose increase is (are) compared to the control is (are) selected from (Table 12):
Cer(d18:1/20:0)/apolipoprotein A-I (mg/dL), Cer(d18:1/24:1)/apolipoprotein A-I (mg/dL), LacCer(d18:1/20:0)/apolipoprotein A-I (mg/dL), Total Cer/apolipoprotein A-I (mg/dL), Total LacCer/apolipoprotein A-I (mg/dL), Cer(d18:1/18:0)/apolipoprotein A-I (mg/dL), LacCer(d18:1/22:0)/apolipoprotein A-I (mg/dL), LacCer(d18:1/20:0)/HDL cholesterol (EDTA) (mg/dL) and Cer(d18:1/24:1)/apolipoprotein B (mg/dL).

In another preferred embodiment, the one or more lipid-clinical concentration ratio(s) whose decrease is (are) compared to the control is (are) selected from (Table 12):
Cer(d18:0/24:0)/apolipoprotein B (mg/dL), Cer(d18:0/24:0)/total cholesterol (EDTA) (mg/dL), Cer(d18:0/24:0)/apolipoprotein B (mg/dL), PC 16:0/20:4/apolipoprotein B (mg/dL) and Cer(d18:0/24:0)/apolipoprotein A-I (mg/dL).

In a particularly preferred embodiment, the lipid-clinical concentration ratio whose increase is compared to the control is (are) selected from (Table 13):
Cer(d18:1/20:0)/apolipoprotein A-I (mg/dL), Cer(d18:1/24:1)/apolipoprotein A-I (mg/dL), LacCer(d18:1/20:0)/apolipoprotein A-I (mg/dL), Total LacCer/apolipoprotein A-I (mg/dL), LacCer(d18:1/20:0)/HDL cholesterol (EDTA) (mg/dL) and Cer(d18:1/18:0)/apolipoprotein A-I (mg/dL).

For the purposes of the invention, and particularly for lipid-clinical concentration ratios, an Apolipoprotein A-I measurement may alternatively be an Apolipoprotein A-II measurement.

claim 2 (note claims only have preferred embodiments) In another aspect the present invention relates to a method for evaluating the effectiveness of a treatment of CVD and/or one or more of its complications, such as AMI or CVD death, in a subject, comprising determining in a sample from said subject the concentration(s) of one or more lipid(s), wherein (an) increased or decreased concentration(s) in said sample, when compared to a control sample, is (are) indicative of effectiveness of said treatment, wherein the one or more lipid(s) whose increase(s) in concentration is (are) compared to the control is (are) selected from (Table 4a and 7a):
Cer(d18:1/18:0), Cer(d18:1/20:0), Cer(d18:1/24:1), GlcCer(d18:1/18:0), LacCer(d18:1/18:0), LacCer(d18:1/20:0), LacCer(d18:1/22:0), LacCer(d18:1/24:0), PC O-32:0 (KDdiA-PC), PS O-16:0/18:2-alkenyl, PS O-16:1/18:2-alkyl, PS O-18:0/18:2-alkenyl (PS O-18:1/18:2-alkyl), PS O-18:2/16:0-alkenyl and Total LacCer;

and wherein the one or more lipid(s) whose decrease(s) in concentration is (are) compared to the control is (are) selected from (Table 4a and 7a):
CE 14:0, CE 16:0, CE 17:1, CE 20:3, Cer(d18:0/22:0), Cer(d18:0/24:0), LPC 18:1, PC 16:0/18:2, PC 16:0/20:3, PC 16:0/20:4, PC 16:0/22:6, PC 18:0/18:1, PC 18:0/20:3, PC 18:0/20:4, PC 18:1/18:2, SM (d18:1/14:0) (d18:1/13:1-OH), SM (d18:1/23:0) (d18:1/22:1-OH), SM (d18:1/24:0) (d18:1/23:1-OH), Total CE, Total LPC and Total PC.

In a particular embodiment, the present invention relates to a method for evaluating the effectiveness of a treatment of CVD and/or one or more of its complications, such as AMI or CVD death, in a subject, wherein the subject is not undergoing statin treatment and wherein said method comprises, determining in a sample from said subject the concentration(s) of one or more lipid(s), wherein (an) increased or decreased concentration(s) in said sample, when compared to a control sample, is (are) indicative of effectiveness of said treatment, wherein the one or more lipid(s) whose increase(s) in concentration is (are) compared to the control is (are) selected from (Table 4b and 7b):
Cer(d18:1/16:0), Cer(d18:1/18:0), Cer(d18:1/20:0), Cer(d18:1/22:0), Cer(d18:1/24:1), Cer(d18:1/26:1), GlcCer(d18:1/18:0), GlcCer(d18:1/20:0), GlcCer(d18:1/

24:1), GlcCer(d18:1/26:1), LacCer(d18:1/18:0), LacCer(d18:1/20:0), LacCer(d18:1/22:0), LacCer(d18:1/24:0), LacCer(d18:1/24:1), PC O-32:0 (KDdiA-PC), PS O-16:0/18:2-alkenyl, PS O-16:1/18:2-alkyl, PS O-18:2/16:0-alkenyl, Total Cer, Total DAG and Total LacCer;

and wherein the one or more lipid(s) whose decrease(s) in concentration is (are) compared to the control is (are) selected from (Table 4b and 7b):

CE 14:0, CE 17:1, CE 20:3, Cer(d18:0/24:0), LPC 18:1, PC 16:0/20:3, PC 16:0/20:4, PC 18:0/20:4, PC O-40:3, SM (d18:1/14:0) (d18:1/13:1-OH), Total LPC and Total PC.

In a preferred embodiment (for subjects that are either undergoing or not undergoing statin treatment), the one or more lipid(s) whose increase in concentration is (are) compared to the control is (are) selected from (Table 10):

Cer(d18:1/20:0), LacCer(d18:1/20:0), Cer(d18:1/24:1), LacCer(d18:1/24:1), PS O-18:2/16:0-alkenyl, PS O-16:1/18:2-alkyl, Total Cer, Total LacCer, GlcCer(d18:1/24:1), LacCer(d18:1/22:0) and Cer(d18:1/18:0).

In another preferred embodiment, the one or more lipid(s) whose decrease in concentration is (are) compared to the control is (are) selected from (Table 10):

Total PC, PC 16:0/20:4, Cer(d18:0/24:0), Total LPC, CE 14:0, CE 20:3, CE 17:1, PC 16:0/20:3, LPC 18:1, PC 18:0/20:3, PC 18:0/18:1 and Cer(d18:0/22:0).

In a particularly preferred embodiment, the one or more lipid(s) whose increase in concentration is (are) compared to the control is (are) selected from (Table 13):

Cer(d18:1/20:0), LacCer(d18:1/20:0), Cer(d18:1/24:1), LacCer(d18:1/24:1), LacCer(d18:1/22:0) and Cer(d18:1/18:0);

and the one or more lipid(s) whose decrease in concentration is (are) compared to the control is (are) selected from (Table 13): PC 16:0/20:4 and Cer(d18:0/24:0).

In another alternative embodiment the invention relates to a method for evaluating the effectiveness of a treatment of CVD and/or one or more of its complications, such as AMI or CVD death, in a subject, comprising determining in a sample from said subject one or more lipid-lipid ratio(s), wherein (an) increased or decreased lipid-lipid ratio(s) in said sample, when compared to a control sample, is (are) indicative of effectiveness of said treatment, wherein the one or more lipid-lipid ratio(s) whose increase(s) is (are) compared to the control is (are) selected from (Tables 5a and 8a):

CE 16:0/CE 18:3, CE 18:2/CE 18:3, CE 19:1/Cer(d18:0/22:0), Cer(d18:1/16:0)/LPC 18:1, Cer(d18:1/16:0)/Total PC, Cer(d18:1/18:0)/LPC 16:0, Cer(d18:1/18:0)/LPC 18:1, Cer(d18:1/18:0)/PC 16:0/18:1, Cer(d18:1/18:0)/PC 16:0/20:3, Cer(d18:1/18:0)/PC 16:0/20:4, Cer(d18:1/18:0)/PC 18:0/20:4, Cer(d18:1/18:0)/Total LPC, Cer(d18:1/18:0)/Total PC, Cer(d18:1/20:0)/PC 16:0/18:1, Cer(d18:1/20:0)/PC 16:0/20:3, Cer(d18:1/20:0)/PC 16:0/20:4, Cer(d18:1/20:0)/PC 18:0/20:4, Cer(d18:1/20:0)/PC 18:1/18:1, Cer(d18:1/20:0)/Total PC, Cer(d18:1/22:0)/LPC 18:2, Cer(d18:1/22:0)/PC 16:0/20:3, Cer(d18:1/22:0)/PC 16:0/20:4, Cer(d18:1/22:0)/Total PC, Cer(d18:1/24:1)/LPC 18:1, Cer(d18:1/24:1)/LPC 18:2, Cer(d18:1/24:1)/PC 16:0/18:1, Cer(d18:1/24:1)/PC 16:0/20:3, Cer(d18:1/24:1)/PC 16:0/20:4, Cer(d18:1/24:1)/PC 18:0/18:1, Cer(d18:1/24:1)/PC 18:0/20:3, Cer(d18:1/24:1)/PC 18:0/20:4, Cer(d18:1/24:1)/SM (d18:1/24:0) (d18:1/23:1-OH), Cer(d18:1/24:1)/Total CE, Cer(d18:1/24:1)/Total LPC, Cer(d18:1/24:1)/Total PC, Cer(d18:1/26:0)/PC O-40:0, GlcCer(d18:1/20:0)/PC 16:0/20:4, GlcCer(d18:1/20:0)/Total PC, GlcCer(d18:1/26:0)/Total CE, LacCer(d18:1/16:0)/Total LPC, LacCer(d18:1/18:0)/PC 16:0/18:1, LacCer(d18:1/18:0)/PC 16:0/20:3, LacCer(d18:1/18:0)/PC 18:0/18:1, LacCer(d18:1/18:0)/PC 18:0/20:3, LacCer(d18:1/18:0)/PC 18:1/18:1, LacCer(d18:1/18:0)/PC 18:1/18:2, LacCer(d18:1/18:0)/Total LPC, LacCer(d18:1/18:0)/Total PC, LacCer(d18:1/20:0)/PC 16:0/18:1, LacCer(d18:1/20:0)/PC 16:0/20:3, LacCer(d18:1/20:0)/PC 18:0/18:1, LacCer(d18:1/20:0)/PC 18:0/20:3 LacCer(d18:1/20:0)/PC 18:1/18:1, LacCer(d18:1/20:0)/PC 18:1/18:2, LacCer(d18:1/20:0)/PC 18:2/18:2, LacCer(d18:1/20:0)/SM (d18:1/17:1-OH), LacCer(d18:1/20:0)/SM (d18:1/18:0), LacCer(d18:1/20:0)/Total LPC, LacCer(d18:1/20:0)/Total PC, LacCer(d18:1/20:0)/Total SM, LacCer(d18:1/22:0)/PC 16:0/20:3, LacCer(d18:1/22:0)/PC 16:0/20:4, LacCer(d18:1/22:0)/PC 18:0/20:3, LacCer(d18:1/22:0)/SM (d18:1/14:0) (d18:1/13:1-OH), LacCer(d18:1/22:0)/Total LPC, LacCer(d18:1/22:0)/Total PC, LacCer(d18:1/24:0)/PC 16:0/20:3, LacCer(d18:1/24:0)/Total LPC, LacCer(d18:1/24:1)/Total LPC, LacCer(d18:1/24:1)/Total PC, LacCer(d18:1/24:1)/Total PC O, PC 16:0/16:0/PC 16:0/20:4, PC 16:0/16:0/Total PC, PC 16:0/18:2/Total PC, PC O-18:0/18:2-alkyl/PC O-36:5, PC O-32:0 (KDdiA-PC)/PC O-38:5, PS O-16:0/18:2-alkenyl/Total PS O, PS O-16:1/18:2-alkyl/Total PS O, PS O-18:0/18:2-alkenyl (PS O-18:1/18:2-alkyl)/Total PS O, PS O-18:2/16:0-alkenyl/Total PS O, Total Cer/Total PC, Total LacCer/Total PC and Total LacCer/Total PC O;

and wherein one or more lipid-lipid ratio(s) whose decrease is (are) compared to the control is (are) selected from (Tables 5a and 8a):

CE 14:0/Cer(d18:1/24:1), CE 16:0/Cer(d18:1/24:1), CE 16:1/CE 19:1, CE 16:1/Cer(d18:1/18:0), CE 16:1/Cer(d18:1/20:0), CE 16:1/Cer(d18:1/24:1), CE 16:1/GlcCer(d18:1/18:0), CE 16:1/GlcCer(d18:1/20:0), CE 16:1/LacCer(d18:1/16:0), CE 16:1/LacCer(d18:1/18:0), CE 16:1/LacCer(d18:1/20:0), CE 16:1/LacCer(d18:1/22:0), CE 16:1/LacCer(d18:1/24:0), CE 16:1/PC 16:0/16:0, CE 16:1/Total LacCer, CE 17:1/Cer(d18:1/24:1), CE 17:1/GlcCer(d18:1/24:1), CE 17:1/LacCer(d18:1/18:0), CE 18:1/Total LacCer, CE 18:3/Cer(d18:1/16:0), CE 18:3/Cer(d18:1/18:0), CE 18:3/Cer(d18:1/20:0), CE 18:3/Cer(d18:1/22:0), CE 18:3/Cer(d18:1/24:0), CE 18:3/Cer(d18:1/24:1), CE 18:3/GlcCer(d18:1/18:0), CE 18:3/GlcCer(d18:1/20:0), CE 18:3/LacCer(d18:1/18:0), CE 18:3/LacCer(d18:1/20:0), CE 18:3/LacCer(d18:1/22:0), CE 18:3/LacCer(d18:1/24:0), CE 18:3/PC 16:0/16:0, CE 18:3/PC O-34:1, CE 18:3/PS O-16:0/18:1-alkenyl (PS O-16:1/18:1-alkyl), CE 18:3/PS O-16:0/18:2-alkenyl, CE 18:3/PS O-16:1/18:2-alkyl, CE 18:3/Total CE, CE 18:3/Total Cer, CE 18:3/Total LacCer, CE 20:3/Cer(d18:1/24:1), CE 20:3/LacCer(d18:1/20:0), Cer(d18:0/22:0)/Cer(d18:1/18:0), Cer(d18:0/22:0)/Cer(d18:1/20:0), Cer(d18:0/22:0)/Cer(d18:1/22:0), Cer(d18:0/22:0)/Cer(d18:1/24:1), Cer(d18:0/22:0)/LacCer(d18:1/24:0), Cer(d18:0/22:0)/PS O-16:0/18:2-alkenyl, Cer(d18:0/22:0)/PS O-16:1/18:2-alkyl, Cer(d18:0/22:0)/Total CE, Cer(d18:0/24:0)/Cer(d18:1/16:0), Cer(d18:0/24:0)/Cer(d18:1/18:0), Cer(d18:0/24:0)/Cer(d18:1/20:0), Cer(d18:0/24:0)/Cer(d18:1/22:0), Cer(d18:0/24:0)/Cer(d18:1/24:1), Cer(d18:0/24:0)/GlcCer(d18:1/20:0), Cer(d18:0/24:0)/LacCer(d18:1/24:0), Cer(d18:0/24:0)/PS O-16:0/18:2-alkenyl, Cer(d18:0/24:0)/PS O-16:1/18:2-alkyl, Cer(d18:0/24:0)/SM (d18:1/17:0) (d18:1/16:1-OH), Cer(d18:0/24:0)/Total CE, Cer(d18:0/24:0)/Total Cer, Cer (d18:0/24:1)/Total CE, GlcCer(d18:1/26:0)/LacCer (d18:1/20:0), GlcCer(d18:1/26:0)/LacCer(d18:1/22:0), LPC 16:0/LacCer(d18:1/20:0), LPC 16:0/LacCer(d18:1/22:0), LPC 16:0/LacCer(d18:1/24:1), LPC 16:0/Total LacCer, LPC 18:1/LacCer(d18:1/20:0), LPC 18:2/LacCer(d18:1/20:0), LPC 18:2/PS O-16:0/18:2-alkenyl, LPC 18:2/PS O-16:1/18:2-alkyl, PC 16:0/20:3/PS O-16:0/18:2-alkenyl, PC 16:0/20:3/PS O-16:1/18:2-alkyl, PC 18:1/18:2/PS O-16:0/18:2-alkenyl, PC 18:1/18:2/PS O-16:1/18:2-alkyl, SM (d18:1/24:0) (d18:1/23:1-OH)/Total Cer and Total LPC/Total LacCer.

In another alternative embodiment the invention relates to a method for evaluating the effectiveness of a treatment of CVD and/or one or more of its complications, such as AMI or CVD death, in a subject, wherein the subject is not undergoing statin treatment and wherein said method comprises comprising determining in a sample from said subject one or more lipid-lipid ratio(s), wherein (an) increased or decreased lipid-lipid ratio(s) in said sample, when compared to a control sample, is (are) indicative of effectiveness of said treatment, wherein the one or more lipid-lipid ratio(s) whose increase(s) is (are) compared to the control is (are) selected from (Tables 5b and 8b):

CE 16:0/CE 18:3, CE 18:0/CE 18:3, CE 18:2/CE 18:3, Cer(d18:1/16:0)/LPC 18:1, Cer(d18:1/16:0)/Total PC, Cer(d18:1/18:0)/LPC 18:1, Cer(d18:1/18:0)/PC 16:0/18:1, Cer(d18:1/18:0)/PC 16:0/20:3, Cer(d18:1/18:0)/PC 16:0/20:4, Cer(d18:1/18:0)/PC 18:0/18:1, Cer(d18:1/18:0)/PC 18:0/20:4, Cer(d18:1/18:0)/PC 18:1/18:1, Cer(d18:1/18:0)/SM (d18:1/14:0) (d18:1/13:1-OH), Cer(d18:1/18:0)/SM (d18:1/17:2-OH), Cer(d18:1/18:0)/SM (d18:1/18:1), Cer(d18:1/18:0)/Total CE, Cer (d18:1/18:0)/Total LPC, Cer(d18:1/18:0)/Total PC, Cer (d18:1/20:0)/PC 16:0/18:1, Cer(d18:1/20:0)/PC 16:0/20:3, Cer(d18:1/20:0)/PC 16:0/20:4, Cer(d18:1/20:0)/PC 18:0/18:1, Cer(d18:1/20:0)/PC 18:0/20:4, Cer(d18:1/20:0)/PC 18:1/18:1, Cer(d18:1/20:0)/SM (d18:1/14:0) (d18:1/13:1-OH), Cer(d18:1/20:0)/Total LPC, Cer (d18:1/20:0)/Total PC, Cer(d18:1/20:0)/Total PC O, Cer(d18:1/22:0)/LPC 18:2, Cer(d18:1/22:0)/PC 16:0/20:3, Cer(d18:1/22:0)/PC 16:0/20:4, Cer(d18:1/22:0)/PC 18:0/20:4, Cer(d18:1/22:0)/Total PC, Cer(d18:1/24:1)/LPC 18:1, Cer(d18:1/24:1)/LPC 18:2, Cer(d18:1/24:1)/PC 16:0/18:1, Cer(d18:1/24:1)/PC 16:0/18:2, Cer (d18:1/24:1)/PC 16:0/20:3, Cer(d18:1/24:1)/PC 16:0/20:4, Cer(d18:1/24:1)/PC 18:0/18:1, Cer(d18:1/24:1)/PC 18:0/18:2, Cer(d18:1/24:1)/PC 18:0/20:3, Cer(d18:1/24:1)/PC 18:0/20:4, Cer(d18:1/24:1)/PC 18:1/18:1, Cer(d18:1/24:1)/PC 18:1/18:2, Cer(d18:1/24:1)/PC O-40:3, Cer(d18:1/24:1)/SM (d18:1/17:1-OH), Cer (d18:1/24:1)/SM (d18:1/18:0), Cer(d18:1/24:1)/SM (d18:1/23:0) (d18:1/22:1-OH), Cer(d18:1/24:1)/SM (d18:1/24:0) (d18:1/23:1-OH), Cer(d18:1/24:1)/Total CE, Cer(d18:1/24:1)/Total LPC, Cer(d18:1/24:1)/Total PC, GlcCer(d18:1/26:0)/Total CE, GlcCer(d18:1/26:1)/Total CE, LacCer(d18:1/18:0)/Total PC, LacCer(d18:1/20:0)/PC 16:0/20:3, LacCer(d18:1/20:0)/PC 16:0/20:4, LacCer(d18:1/20:0)/PC 18:0/18:1, LacCer(d18:1/20:0)/PC 18:0/20:3, LacCer(d18:1/20:0)/PC 18:0/20:4, LacCer(d18:1/20:0)/PC 18:1/18:2, LacCer(d18:1/20:0)/SM (d18:1/17:1-OH), LacCer(d18:1/20:0)/SM (d18:1/18:0), LacCer(d18:1/20:0)/Total CE, LacCer(d18:1/20:0)/Total LPC, LacCer(d18:1/20:0)/Total PC, LacCer (d18:1/20:0)/Total SM, LacCer(d18:1/24:0)/Total LPC, PC 16:0/16:0/PC 16:0/20:4, PC 16:0/16:0/Total PC, PC O-32:0 (KDdiA-PC)/Total PC O, PS O-16:0/18:2-alkenyl/Total PC, PS O-16:0/18:2-alkenyl/Total PC O, PS O-16:0/18:2-alkenyl/Total PS O, PS O-16:1/18:2-alkyl/Total PC, PS O-16:1/18:2-alkyl/Total PC O, PS O-16:1/18:2-alkyl/Total PS O, PS O-18:2/16:0-alkenyl/Total PC O, PS O-18:2/16:0-alkenyl/Total PS O, SM (d18:1/17:0) (d18:1/16:1-OH)/Total PC O, Total Cer/Total PC, Total DAG/Total LPC, Total DAG/Total PC, Total DAG/Total PC O and Total LacCer/Total PC;

and wherein the one or more lipid-lipid ratio(s) whose decrease(s) is (are) compared to the control is (are) selected from (Tables 5b and 8b):

CE 14:0/Cer(d18:1/18:0), CE 14:0/Cer(d18:1/24:1), CE 14:0/Total DAG, CE 15:0/Cer(d18:1/20:0), CE 16:0/Cer(d18:1/18:0), CE 16:0/Cer(d18:1/24:1), CE 16:1/CE 19:1, CE 16:1/Cer(d18:1/18:0), CE 16:1/Cer(d18:1/20:0), CE 16:1/Cer(d18:1/24:1), CE 16:1/GlcCer (d18:1/24:1), CE 16:1/LacCer(d18:1/18:0), CE 16:1/LacCer(d18:1/24:0), CE 16:1/Total LacCer, CE 17:1/Cer(d18:1/18:0), CE 17:1/Cer(d18:1/24:1), CE 18:2/Cer(d18:1/20:0), CE 18:2/Cer(d18:1/24:1), CE 18:3/Cer(d18:1/16:0), CE 18:3/Cer(d18:1/18:0), CE 18:3/Cer(d18:1/20:0), CE 18:3/Cer(d18:1/22:0), CE 18:3/Cer(d18:1/24:0), CE 18:3/Cer(d18:1/24:1), CE 18:3/GlcCer(d18:1/20:0), CE 18:3/LacCer(d18:1/20:0), CE 18:3/LacCer(d18:1/22:0), CE 18:3/LacCer(d18:1/24:0), CE 18:3/PC 16:0/16:0, CE 18:3/PC O-34:1, CE 18:3/PS O-16:0/18:2-alkenyl, CE 18:3/PS O-16:1/18:2-alkyl, CE 18:3/Total CE, CE 18:3/Total Cer, CE 18:3/Total DAG, CE 18:3/Total LacCer, CE 20:3/Cer (d18:1/24:1), CE 20:3/LacCer(d18:1/20:0), CE 20:4/Cer(d18:1/18:0), CE 20:4/Cer(d18:1/24:1), CE 20:4/GlcCer(d18:1/20:0), CE 20:4/GlcCer(d18:1/24:1), CE 20:4/LacCer(d18:1/20:0), CE 20:5/LacCer(d18:1/20:0), Cer(d18:0/22:0)/Cer(d18:1/18:0), Cer(d18:0/22:0)/Cer(d18:1/20:0), Cer(d18:0/22:0)/Cer(d18:1/24:1), Cer(d18:0/22:0)/PS O-16:0/18:2-alkenyl, Cer(d18:0/22:0)/PS O-16:1/18:2-alkyl, Cer(d18:0/22:0)/Total CE, Cer (d18:0/22:0)/Total DAG, Cer(d18:0/22:0)/Total GlcCer, Cer(d18:0/24:0)/Cer(d18:1/18:0), Cer(d18:0/24:0)/Cer(d18:1/20:0), Cer(d18:0/24:0)/Cer(d18:1/24:1), Cer(d18:0/24:0)/PS O-16:0/18:2-alkenyl, Cer(d18:0/24:0)/PS O-16:1/18:2-alkyl, Cer(d18:0/24:0)/Total CE, Cer(d18:0/24:0)/Total Cer, DAG 16:0/18:1/Total DAG, GlcCer(d18:1/26:0)/LacCer(d18:1/20:0), LPC 16:0/LacCer(d18:1/24:0), LPC 18:1/LacCer(d18:1/20:0), LPC 18:2/LacCer(d18:1/20:0), PC 16:0/20:3/PS O-16:0/18:2-alkenyl, PC 16:0/20:3/PS O-16:1/18:2-alkyl, PC 16:0/20:4/PS O-16:0/18:2-alkenyl, PC 16:0/20:4/PS O-16:1/18:2-alkyl, PC 16:0/20:4/Total DAG, PC 18:0/20:3/PS O-16:0/18:2-alkenyl, PC 18:0/20:3/PS O-16:1/18:2-alkyl, PC 18:0/20:3/PS O-18:2/16:0-alkenyl, PC 18:0/20:4/PS O-16:0/18:2-alkenyl, PC 18:0/20:4/PS O-16:1/18:2-alkyl, PC 18:1/18:2/PS O-16:0/18:2-alkenyl, PC 18:1/18:2/PS O-16:1/18:2-alkyl, PC 18:1/18:2/Total Cer, PC O-40:3/PS O-18:2/16:0-alkenyl, SM (d18:1/23:0) (d18:1/22:1-OH)/Total DAG, SM (d18:1/24:0) (d18:1/23:1-OH)/Total Cer, Total CE/Total DAG and Total LPC/Total LacCer.

In a preferred embodiment (for subjects that are either undergoing or not undergoing statin treatment), the one or more lipid-lipid ratio(s) whose increase is (are) compared to the control is (are) selected from (Table 11):

GlcCer(d18:1/26:1)/Total CE, Cer(d18:1/24:1)/Total PC, Cer(d18:1/24:1)/PC 16:0/20:4, Cer(d18:1/20:0)/PC 16:0/20:4, LacCer(d18:1/20:0)/PC 16:0/20:3, Total Cer/Total PC, Total LacCer/Total PC, LacCer(d18:1/20:0)/PC 18:1/18:2, PS O-16:0/18:2-alkenyl/Total PS O, Cer(d18:1/18:0)/PC 16:0/20:4, LacCer(d18:1/20:0)/ Total LPC and LacCer(d18:1/20:0)/PC 16:0/20:4.

In another preferred embodiment, the one or more lipid-lipid ratio(s) whose decrease is (are) compared to the control is (are) selected from (Table 11):

Cer(d18:0/24:0)/Cer(d18:1/24:1), Cer(d18:0/22:0)/Cer(d18:1/24:1), DAG 16:0/18:1/Total DAG, Cer(d18:0/24:0)/Cer(d18:1/22:0), Cer(d18:0/24:0)/Total CE, Cer(d18:0/24:0)/Cer(d18:1/24:1), Cer(d18:0/24:0)/Total Cer, Cer(d18:0/24:0)/Cer(d18:1/18:0), Cer(d18:0/24:0)/PS O-16:0/18:2-alkenyl, Cer(d18:0/24:0)/LacCer(d18:1/24:0), Cer(d18:0/22:0)/Cer(d18:1/18:0), Cer(d18:0/24:0)/Cer(d18:1/22:0), Cer(d18:0/22:0)/Cer(d18:1/20:0), Cer(d18:0/22:0)/PS O-16:0/18:2-alkenyl, Cer(d18:0/22:0)/PS O-16:1/18:2-alkyl, GlcCer(d18:1/26:0)/LacCer(d18:1/20:0), Total LPC/Total LacCer and GlcCer(d18:1/26:0)/LacCer(d18:1/22:0).

In a particularly preferred embodiment, the one or more lipid-lipid ratio(s) whose increase is (are) compared to the control is (are) selected from (Table 13):

Cer(d18:1/24:1)/PC 16:0/20:4, LacCer(d18:1/20:0)/PC 16:0/20:3, PS O-16:0/18:2-alkenyl/Total PS 0 and Cer(d18:1/18:0)/PC 16:0/20:4;

and the one or more lipid-lipid ratio(s) whose decrease is (are) compared to the control is (are) selected from (Table 13):

GlcCer(d18:1/26:0)/LacCer(d18:1/20:0), DAG 16:0/18:1/Total DAG, Cer(d18:0/24:0)/Total Cer, Total LPC/Total LacCer, GlcCer(d18:1/26:0)/LacCer(d18:1/22:0), Cer(d18:0/24:0)/Cer(d18:1/24:1), Cer(d18:0/24:0)/Cer(d18:1/18:0), Cer(d18:0/24:0)/PS O-16:0/18:2-alkenyl, Cer(d18:0/24:0)/Cer(d18:1/22:0), Cer(d18:0/22:0)/PS O-16:0/18:2-alkenyl, Cer(d18:0/22:0)/PS O-16:1/18:2-alkyl and Cer(d18:0/24:0)/LacCer(d18:1/24:0).

In yet another alternative embodiment the invention relates to a method for evaluating the effectiveness of a treatment of CVD and/or one or more of its complications, such as AMI or CVD death, in a subject, comprising determining in a sample from said subject one or more lipid-clinical concentration ratio(s), wherein (an) increased or decreased lipid-clinical concentration ratio(s) in said sample, when compared to a control sample, is (are) indicative of effectiveness of said treatment, wherein the one or more lipid-clinical concentration ratio(s) whose increase(s) is (are) compared to the control is (are) selected from (Tables 6a and 9a):

Cer(d18:1/16:0)/triglycerides (EDTA) (mg/dL), Cer(d18:1/18:0)/apolipoprotein A-I (mg/dL), Cer(d18:1/18:0)/apolipoprotein B (mg/dL), Cer(d18:1/18:0)/HDL cholesterol (EDTA) (mg/dL), Cer(d18:1/18:0)/total cholesterol (EDTA) (mg/dL), Cer(d18:1/18:0)/total-c/HDL-c, Cer(d18:1/18:0)/triglycerides (EDTA) (mg/dL), Cer(d18:1/20:0)/apolipoprotein A-I (mg/dL), Cer(d18:1/20:0)/apolipoprotein B (mg/dL), Cer(d18:1/20:0)/HDL cholesterol (EDTA) (mg/dL), Cer(d18:1/20:0)/total cholesterol (EDTA) (mg/dL), Cer(d18:1/20:0)/triglycerides (EDTA) (mg/dL), Cer(d18:1/22:0)/apolipoprotein B (mg/dL), Cer(d18:1/22:0)/LDL cholesterol (EDTA) (mg/dL), Cer(d18:1/22:0)/triglycerides (EDTA) (mg/dL), Cer(d18:1/24:1)/apolipoprotein A-I (mg/dL), Cer(d18:1/24:1)/apolipoprotein B (mg/dL), Cer(d18:1/24:1)/LDL cholesterol (EDTA) (mg/dL), Cer(d18:1/24:1)/total cholesterol (EDTA) (mg/dL), Cer(d18:1/24:1)/total-c/HDL-c, Cer(d18:1/24:1)/triglycerides (EDTA) (mg/dL), GlcCer(d18:1/24:0)/total cholesterol (EDTA) (mg/dL), LacCer(d18:1/16:0)/triglycerides (EDTA) (mg/dL), LacCer(d18:1/18:0)/apolipoprotein A-I (mg/dL), LacCer(d18:1/18:0)/apolipoprotein B (mg/dL), LacCer(d18:1/18:0)/HDL cholesterol (EDTA) (mg/dL), LacCer(d18:1/18:0)/LDL cholesterol (EDTA) (mg/dL), LacCer(d18:1/18:0)/total cholesterol (EDTA) (mg/dL), LacCer(d18:1/18:0)/total-c/HDL-c, LacCer(d18:1/18:0)/triglycerides (EDTA) (mg/dL), LacCer(d18:1/20:0)/apoA1/apoB, LacCer(d18:1/20:0)/apolipoprotein A-I (mg/dL), LacCer(d18:1/20:0)/apolipoprotein B (mg/dL), LacCer(d18:1/20:0)/HDL cholesterol (EDTA) (mg/dL), LacCer(d18:1/20:0)/LDL cholesterol (EDTA) (mg/dL), LacCer(d18:1/20:0)/LDL-c/HDL-c, LacCer(d18:1/20:0)/total cholesterol (EDTA) (mg/dL), LacCer(d18:1/20:0)/total-c/HDL-c, LacCer(d18:1/20:0)/triglycerides (EDTA) (mg/dL), LacCer(d18:1/22:0)/apoA1/apoB, LacCer(d18:1/22:0)/apolipoprotein A-I (mg/dL), LacCer(d18:1/22:0)/apolipoprotein B (mg/dL), LacCer(d18:1/22:0)/HDL cholesterol (EDTA) (mg/dL), LacCer(d18:1/22:0)/LDL cholesterol (EDTA) (mg/dL), LacCer(d18:1/22:0)/total cholesterol (EDTA) (mg/dL), LacCer(d18:1/22:0)/total-c/HDL-c, LacCer(d18:1/22:0)/triglycerides (EDTA) (mg/dL), LacCer(d18:1/24:0)/apoA1/apoB, LacCer(d18:1/24:1)/apolipoprotein A-I (mg/dL), LacCer(d18:1/24:1)/apolipoprotein B (mg/dL), LacCer(d18:1/24:1)/total cholesterol (EDTA) (mg/dL), LacCer(d18:1/24:1)/triglycerides (EDTA) (mg/dL), PC O-32:0 (KDdiA-PC)/apolipoprotein A-I (mg/dL), P C O-32:0 (KDdiA-PC)/triglycerides (EDTA) (mg/dL), PC O-34:1/triglycerides (EDTA) (mg/dL), PS O-16:0/18:1-alkenyl (PS O-16:1/18:1-alkyl)/triglycerides (EDTA) (mg/dL), PS O-16:0/18:2-alkenyl/triglycerides (EDTA) (mg/dL), PS O-16:1/18:2-alkyl/triglycerides (EDTA) (mg/dL), PS O-18:2/16:0-alkenyl/HDL cholesterol (EDTA) (mg/dL), PS O-18:2/16:0-alkenyl/triglycerides (EDTA) (mg/dL), Total Cer/apolipoprotein A-I (mg/dL), Total Cer/total cholesterol (EDTA) (mg/dL), Total Cer/triglycerides (EDTA) (mg/dL), Total GlcCer/apolipoprotein B (mg/dL), Total GlcCer/total cholesterol (EDTA) (mg/dL), Total LacCer/apolipoprotein A-I (mg/dL), Total LacCer/apolipoprotein B (mg/dL), Total LacCer/total cholesterol (EDTA) (mg/dL) and Total LacCer/triglycerides (EDTA) (mg/dL);

and wherein the one or more lipid-clinical concentration ratio(s) whose decrease is (are) compared to the control is (are) selected from Tables 6a and 9a:

CE 14:0/apolipoprotein B (mg/dL), CE 14:0/LDL cholesterol (EDTA) (mg/dL), CE 14:0/LDL-c/HDL-c, CE 14:0/total cholesterol (EDTA) (mg/dL), CE 14:0/total-c/HDL-c, CE 16:1/apolipoprotein B (mg/dL), CE 16:1/HDL cholesterol (EDTA) (mg/dL), CE 16:1/LDL cholesterol (EDTA) (mg/dL), CE 16:1/total cholesterol (EDTA) (mg/dL), CE 17:1/LDL-c/HDL-c, CE 18:3/apoA1/apoB, CE 18:3/apolipoprotein A-I (mg/dL), CE 18:3/apolipoprotein B (mg/dL), CE 18:3/HDL cholesterol (EDTA) (mg/dL), CE 18:3/LDL cholesterol (EDTA) (mg/dL), CE 18:3/LDL-c/HDL-c, CE 18:3/total cholesterol (EDTA) (mg/dL), CE 18:3/total-c/HDL-c, CE 20:3/apolipoprotein B (mg/dL), CE 20:3/LDL-c/HDL-c, CE 20:3/total-c/HDL-c, CE 20:5/apolipoprotein B (mg/dL), CE 20:5/HDL cholesterol (EDTA) (mg/dL), CE 20:5/LDL cholesterol (EDTA) (mg/dL), Cer(d18:0/22:0)/apolipoprotein B (mg/dL), Cer(d18:0/22:0)/LDL-c/HDL-c, Cer(d18:0/22:0)/total-c/HDL-c, Cer(d18:0/24:0)/apolipoprotein A-I (mg/dL), Cer(d18:0/24:0)/apolipoprotein B (mg/dL), Cer(d18:0/24:0)/HDL cholesterol (EDTA) (mg/dL), Cer(d18:0/

24:0)/LDL cholesterol (EDTA) (mg/dL), Cer(d18:0/24:0)/LDL-c/HDL-c, Cer(d18:0/24:0)/total cholesterol (EDTA) (mg/dL), Cer(d18:0/24:0)/total-c/HDL-c, LPC 18:2/apoA1/apoB, LPC 18:2/apolipoprotein B (mg/dL), LPC 18:2/HDL cholesterol (EDTA) (mg/dL), LPC 18:2/LDL cholesterol (EDTA) (mg/dL), LPC 18:2/LDL-c/HDL-c, LPC 18:2/total cholesterol (EDTA) (mg/dL), PC 16:0/20:3/apolipoprotein B (mg/dL), PC 16:0/20:3/HDL cholesterol (EDTA) (mg/dL), PC 16:0/20:3/LDL-c/HDL-c, PC 16:0/20:3/total-c/HDL-c, PC 16:0/20:4/apolipoprotein A-I (mg/dL), PC 16:0/20:4/apolipoprotein B (mg/dL), PC 16:0/20:4/LDL cholesterol (EDTA) (mg/dL), PC 16:0/20:4/LDL-c/HDL-c, PC 16:0/20:4/total cholesterol (EDTA) (mg/dL), PC 16:0/20:4/total-c/HDL-c, PC 18:0/18:1/LDL-c/HDL-c, PC 18:0/20:3/LDL-c/HDL-c, PC 18:0/20:3/total-c/HDL-c, PC 18:0/20:4/apoA1/apoB, Total LPC/LDL-c/HDL-c, Total LPC/total-c/HDL-c, Total PC/apolipoprotein B (mg/dL), Total PC/LDL-c/HDL-c, Total PC/total cholesterol (EDTA) (mg/dL) and Total PC/total-c/HDL-c.

In yet another alternative embodiment the invention relates to a method for evaluating the effectiveness of a treatment of CVD and/or one or more of its complications, such as AMI or CVD death, in a subject, wherein the subject is not undergoing statin treatment and wherein said method comprises determining in a sample from said subject one or more lipid-clinical concentration ratio(s), wherein (an) increased or decreased lipid-clinical concentration ratio(s) in said sample, when compared to a control sample, is (are) indicative of effectiveness of said treatment, wherein the one or more lipid-clinical concentration ratio(s) whose increase (s) is (are) compared to the control is (are) selected from (Tables 6b and 9b):

Cer(d18:1/16:0)/apolipoprotein A-I (mg/dL), Cer(d18:1/16:0)/LDL cholesterol (EDTA) (mg/dL), Cer(d18:1/16:0)/triglycerides (EDTA) (mg/dL), Cer(d18:1/18:0)/apolipoprotein A-I (mg/dL), Cer(d18:1/18:0)/apolipoprotein B (mg/dL), Cer(d18:1/18:0)/HDL cholesterol (EDTA) (mg/dL), Cer(d18:1/18:0)/total cholesterol (EDTA) (mg/dL), Cer(d18:1/18:0)/total-c/HDL-c, Cer(d18:1/18:0)/triglycerides (EDTA) (mg/dL), Cer(d18:1/20:0)/apolipoprotein A-I (mg/dL), Cer(d18:1/20:0)/apolipoprotein B (mg/dL), Cer(d18:1/20:0)/HDL cholesterol (EDTA) (mg/dL), Cer(d18:1/20:0)/LDL cholesterol (EDTA) (mg/dL), Cer(d18:1/20:0)/total cholesterol (EDTA) (mg/dL), Cer(d18:1/20:0)/total-c/HDL-c, Cer(d18:1/20:0)/triglycerides (EDTA) (mg/dL), Cer(d18:1/22:0)/apolipoprotein A-I (mg/dL), Cer(d18:1/22:0)/apolipoprotein B (mg/dL), Cer(d18:1/22:0)/LDL cholesterol (EDTA) (mg/dL), Cer(d18:1/22:0)/total cholesterol (EDTA) (mg/dL), Cer(d18:1/22:0)/triglycerides (EDTA) (mg/dL), Cer(d18:1/24:0)/apolipoprotein A-I (mg/dL), Cer(d18:1/24:0)/apolipoprotein B (mg/dL), Cer(d18:1/24:0)/LDL cholesterol (EDTA) (mg/dL), Cer(d18:1/24:0)/total cholesterol (EDTA) (mg/dL), Cer(d18:1/24:1)/apolipoprotein A-I (mg/dL), Cer(d18:1/24:1)/apolipoprotein B (mg/dL), Cer(d18:1/24:1)/HDL cholesterol (EDTA) (mg/dL), Cer(d18:1/24:1)/LDL cholesterol (EDTA) (mg/dL), Cer(d18:1/24:1)/LDL-c/HDL-c, Cer(d18:1/24:1)/total cholesterol (EDTA) (mg/dL), Cer(d18:1/24:1)/total-c/HDL-c, Cer(d18:1/24:1)/triglycerides (EDTA) (mg/dL), GlcCer(d18:1/20:0)/apolipoprotein B (mg/dL), GlcCer(d18:1/20:0)/total cholesterol (EDTA) (mg/dL), GlcCer(d18:1/24:1)/apolipoprotein B (mg/dL), GlcCer(d18:1/26:1)/apolipoprotein A-I (mg/dL), LacCer(d18:1/16:0)/triglycerides (EDTA) (mg/dL), LacCer(d18:1/18:0)/apolipoprotein A-I (mg/dL), LacCer(d18:1/18:0)/apolipoprotein B (mg/dL), LacCer(d18:1/18:0)/total cholesterol (EDTA) (mg/dL), LacCer(d18:1/20:0)/apoA1/apoB, LacCer(d18:1/20:0)/apolipoprotein A-I (mg/dL), LacCer(d18:1/20:0)/apolipoprotein B (mg/dL), LacCer(d18:1/20:0)/HDL cholesterol (EDTA) (mg/dL), LacCer(d18:1/20:0)/LDL cholesterol (EDTA) (mg/dL), LacCer(d18:1/20:0)/LDL-c/HDL-c, LacCer(d18:1/20:0)/total cholesterol (EDTA) (mg/dL), LacCer(d18:1/20:0)/total-c/HDL-c, LacCer(d18:1/20:0)/triglycerides (EDTA) (mg/dL), LacCer(d18:1/22:0)/apoA1/apoB, LacCer(d18:1/22:0)/apolipoprotein A-I (mg/dL), LacCer(d18:1/22:0)/apolipoprotein B (mg/dL), LacCer(d18:1/22:0)/HDL cholesterol (EDTA) (mg/dL), LacCer(d18:1/22:0)/LDL cholesterol (EDTA) (mg/dL), LacCer(d18:1/22:0)/total cholesterol (EDTA) (mg/dL), LacCer(d18:1/24:1)/apolipoprotein A-I (mg/dL), LacCer(d18:1/24:1)/apolipoprotein B (mg/dL), LacCer(d18:1/24:1)/total cholesterol (EDTA) (mg/dL), LacCer(d18:1/24:1)/triglycerides (EDTA) (mg/dL), PC O-34:1/apolipoprotein B (mg/dL), PS O-16:0/18:2-alkenyl/triglycerides (EDTA) (mg/dL), PS O-16:1/18:2-alkyl/triglycerides (EDTA) (mg/dL), Total Cer/apolipoprotein A-I (mg/dL), Total Cer/apolipoprotein B (mg/dL), Total Cer/LDL cholesterol (EDTA) (mg/dL), Total Cer/total cholesterol (EDTA) (mg/dL), Total DAG/apolipoprotein A-I (mg/dL), Total DAG/triglycerides (EDTA) (mg/dL), Total GlcCer/apolipoprotein B (mg/dL), Total LacCer/apolipoprotein A-I (mg/dL), Total LacCer/apolipoprotein B (mg/dL) and Total LacCer/total cholesterol (EDTA) (mg/dL).

and wherein the one or more lipid-clinical concentration ratio(s) whose decrease is (are) compared to the control is (are) selected from (Tables 6b and 9b):

CE 14:0/apoA1/apoB, CE 14:0/apolipoprotein B (mg/dL), CE 14:0/LDL-c/HDL-c, CE 14:0/total-c/HDL-c, CE 16:1/apoA1/apoB, CE 18:3/apoA1/apoB, CE 18:3/apolipoprotein A-I (mg/dL), CE 18:3/apolipoprotein B (mg/dL), CE 18:3/HDL cholesterol (EDTA) (mg/dL), CE 18:3/LDL cholesterol (EDTA) (mg/dL), CE 18:3/LDL-c/HDL-c, CE 18:3/total cholesterol (EDTA) (mg/dL), CE 18:3/total-c/HDL-c, CE 20:5/triglycerides (EDTA) (mg/dL), Cer(d18:0/24:0)/apolipoprotein B (mg/dL), Cer(d18:0/24:0)/total cholesterol (EDTA) (mg/dL), Cer(d18:0/24:0)/total-c/HDL-c, PC 18:0/20:4/apoA1/apoB, PC O-38:6/apolipoprotein A-I (mg/dL), Total LPC/apoA1/apoB and Total PC/apolipoprotein A-I (mg/dL).

In a preferred embodiment (for subjects that are either undergoing or not undergoing statin treatment), the one or more lipid-clinical concentration ratio(s) whose increase is (are) compared to the control is (are) selected from (Table 12):

Cer(d18:1/20:0)/apolipoprotein A-I (mg/dL), Cer(d18:1/24:1)/apolipoprotein A-I (mg/dL), LacCer(d18:1/20:0)/apolipoprotein A-I (mg/dL), Total Cer/apolipoprotein A-I (mg/dL), Total LacCer/apolipoprotein A-I (mg/dL), Cer(d18:1/18:0)/apolipoprotein A-I (mg/dL), LacCer(d18:1/22:0)/apolipoprotein A-I (mg/dL), LacCer(d18:1/20:0)/HDL cholesterol (EDTA) (mg/dL) and Cer(d18:1/24:1)/apolipoprotein B (mg/dL).

In another preferred embodiment, the one or more lipid-clinical concentration ratio(s) whose decrease is (are) compared to the control is (are) selected from (Table 12):

Cer(d18:0/24:0)/apolipoprotein B (mg/dL), Cer(d18:0/24:0)/total cholesterol (EDTA) (mg/dL), Cer(d18:0/24:0)/apolipoprotein B (mg/dL), PC 16:0/20:4/apolipoprotein B (mg/dL) and Cer(d18:0/24:0)/apolipoprotein A-I (mg/dL).

In a particularly preferred embodiment, the lipid-clinical concentration ratio(s) whose increased is (are) compared to the control are selected from (Table 13):
Cer(d18:1/20:0)/apolipoprotein A-I (mg/dL), Cer(d18:1/24:1)/apolipoprotein A-I (mg/dL), LacCer(d18:1/20:0)/apolipoprotein A-I (mg/dL), Total LacCer/apolipoprotein A-I (mg/dL), LacCer(d18:1/20:0)/HDL cholesterol (EDTA) (mg/dL) and Cer(d18:1/18:0)/apolipoprotein A-I (mg/dL).

For the purposes of the invention, and particularly for lipid-clinical concentration ratios, an Apolipoprotein A-I measurement may alternatively be an Apolipoprotein A-II measurement.

Claim 3 (note claims only have preferred embodiments)
In yet another aspect the invention relates to a method of choosing an appropriate treatment of CVD and/or one or more of its complications, such as AMI or CVD death, in a subject, comprising determining in a sample from said subject the concentration of one or more lipid(s), wherein (an) increased or decreased concentration(s) in said sample, when compared to a control sample, is (are) indicative of said subject being in need of treatment or a change in, or supplementation of, an already administered treatment, wherein the one or more lipid(s) whose increase(s) in concentration is (are) compared to the control is (are) selected from (Tables 4a and 7a):
Cer(d18:1/18:0), Cer(d18:1/20:0), Cer(d18:1/24:1), GlcCer(d18:1/18:0), LacCer(d18:1/18:0), LacCer(d18:1/20:0), LacCer(d18:1/22:0), LacCer(d18:1/24:0), PC 0-32:0 (KDdiA-PC), PS O-16:0/18:2-alkenyl, PS O-16:1/18:2-alkyl, PS O-18:0/18:2-alkenyl (PS O-18:1/18:2-alkyl), PS O-18:2/16:0-alkenyl and Total LacCer;

and wherein the one or more lipid(s) whose decrease(s) in concentration is (are) compared to the control is (are) selected from (Tables 4a and 7a):
CE 14:0, CE 16:0, CE 17:1, CE 20:3, Cer(d18:0/22:0), Cer(d18:0/24:0), LPC 18:1, PC 16:0/18:2, PC 16:0/20:3, PC 16:0/22:6, PC 18:0/18:1, PC 18:0/20:3, PC 18:0/20:4, PC 18:1/18:2, SM (d18:1/14:0) (d18:1/13:1-OH), SM (d18:1/23:0) (d18:1/22:1-OH), SM (d18:1/24:0) (d18:1/23:1-OH), Total CE, Total LPC and Total PC.

In yet another aspect the invention relates to a method of choosing an appropriate treatment of CVD and/or one or more of its complications, such as AMI or CVD death, in a subject, wherein the subject is not undergoing statin treatment and wherein said method comprises determining in a sample from said subject the concentration of one or more lipid(s), wherein (an) increased or decreased concentration(s) in said sample, when compared to a control sample, is (are) indicative of said subject being in need of treatment or a change in, or supplementation of, an already administered treatment, wherein the one or more lipid(s) whose increase(s) in concentration is (are) compared to the control is (are) selected from (Tables 4b and 7b):
Cer(d18:1/16:0), Cer(d18:1/18:0), Cer(d18:1/20:0), Cer(d18:1/22:0), Cer(d18:1/24:1), Cer(d18:1/26:1), GlcCer(d18:1/18:0), GlcCer(d18:1/20:0), GlcCer(d18:1/24:1), GlcCer(d18:1/26:1), LacCer(d18:1/18:0), LacCer(d18:1/20:0), LacCer(d18:1/22:0), LacCer(d18:1/24:0), LacCer(d18:1/24:1), PC O-32:0 (KDdiA-PC), PS O-16:0/18:2-alkenyl, PS O-16:1/18:2-alkyl, PS O-18:2/16:0-alkenyl, Total Cer, Total DAG and Total LacCer;

and wherein the one or more lipid(s) whose decrease(s) in concentration is (are) compared to the control is (are) selected from (Tables 4b and 7b):
CE 14:0, CE 17:1, CE 20:3, Cer(d18:0/24:0), LPC 18:1, PC 16:0/20:3, PC 16:0/20:4, PC 18:0/20:4, PC O-40:3, SM (d18:1/14:0) (d18:1/13:1-OH), Total LPC and Total PC.

In a preferred embodiment (for subjects that are either undergoing or not undergoing statin treatment), the one or more lipid(s) whose increase in concentration is (are) compared to the control is (are) selected from (Table 10):
Cer(d18:1/20:0), LacCer(d18:1/20:0), Cer(d18:1/24:1), LacCer(d18:1/24:1), PS O-18:2/16:0-alkenyl, PS O-16:1/18:2-alkyl, Total Cer, Total LacCer, GlcCer(d18:1/24:1), LacCer(d18:1/22:0) and Cer(d18:1/18:0).

In another preferred embodiment, the one or more lipid(s) whose decrease in concentration is (are) compared to the control is (are) selected from (Table 10):
Total PC, PC 16:0/20:4, Cer(d18:0/24:0), Total LPC, CE 14:0, CE 20:3, CE 17:1, PC 16:0/20:3, LPC 18:1, PC 18:0/20:3, PC 18:0/18:1 and Cer(d18:0/22:0).

In a particularly preferred embodiment, the one or more lipid(s) whose increase in concentration is (are) compared to the control is (are) selected from (Table 13):
Cer(d18:1/20:0), LacCer(d18:1/20:0), Cer(d18:1/24:1), LacCer(d18:1/24:1), LacCer(d18:1/22:0) and Cer(d18:1/18:0);

and the one or more lipid(s) whose decrease in concentration is (are) compared to the control is (are) selected from (Table 13): PC 16:0/20:4 and Cer(d18:0/24:0).

In an alternative embodiment the invention relates to a method of choosing an appropriate treatment of CVD and/or one or more of its complications, such as AMI or CVD death, in a subject, comprising determining in a sample from said subject one or more lipid-lipid ratio(s), wherein (an) increased or decreased lipid-lipid ratio(s) in said sample, when compared to a control sample, is (are) indicative of said subject being in need of treatment or a change in, or supplementation of, an already administered treatment, wherein the one or more lipid-lipid ratio(s) whose increase(s) is (are) compared to the control is (are) selected from (Tables 5a and 8a):
CE 16:0/CE 18:3, CE 18:2/CE 18:3, CE 19:1/Cer(d18:0/22:0), Cer(d18:1/16:0)/LPC 18:1, Cer(d18:1/16:0)/Total PC, Cer(d18:1/18:0)/LPC 16:0, Cer(d18:1/18:0)/LPC 18:1, Cer(d18:1/18:0)/PC 16:0/18:1, Cer(d18:1/18:0)/PC 16:0/20:3, Cer(d18:1/18:0)/PC 16:0/20:4, Cer(d18:1/18:0)/PC 18:0/20:4, Cer(d18:1/18:0)/Total LPC, Cer(d18:1/18:0)/Total PC, Cer(d18:1/20:0)/PC 16:0/18:1, Cer(d18:1/20:0)/PC 16:0/20:3, Cer(d18:1/20:0)/PC 16:0/20:4, Cer(d18:1/20:0)/PC 18:0/20:4, Cer(d18:1/20:0)/PC 18:1/18:1, Cer(d18:1/20:0)/Total PC, Cer(d18:1/22:0)/LPC 18:2, Cer(d18:1/22:0)/PC 16:0/20:3, Cer(d18:1/22:0)/PC 16:0/20:4, Cer(d18:1/22:0)/Total PC, Cer(d18:1/24:1)/LPC 18:1, Cer(d18:1/24:1)/LPC 18:2, Cer(d18:1/24:1)/PC 16:0/18:1, Cer(d18:1/24:1)/PC 16:0/20:3, Cer(d18:1/24:1)/PC 16:0/20:4, Cer(d18:1/24:1)/PC 18:0/18:1, Cer(d18:1/24:1)/PC 18:0/20:3, Cer(d18:1/24:1)/PC 18:0/20:4, Cer(d18:1/24:1)/SM (d18:1/24:0) (d18:1/23:1-OH), Cer(d18:1/24:1)/Total CE, Cer(d18:1/24:1)/Total LPC, Cer(d18:1/24:1)/Total PC, Cer(d18:1/26:0)/PC O-40:0, GlcCer(d18:1/20:0)/PC 16:0/20:4, GlcCer(d18:1/20:0)/Total PC, GlcCer(d18:1/26:0)/Total CE, LacCer(d18:1/16:0)/Total LPC, LacCer(d18:1/18:0)/PC 16:0/18:1, LacCer (d18:1/18:0)/PC 16:0/20:3, LacCer(d18:1/18:0)/PC 18:0/18:1, LacCer(d18:1/18:0)/PC 18:0/20:3, LacCer (d18:1/18:0)/PC 18:1/18:1, LacCer(d18:1/18:0)/PC 18:1/18:2, LacCer(d18:1/18:0)/Total LPC, LacCer (d18:1/18:0)/Total PC, LacCer(d18:1/20:0)/PC 16:0/ 18:1, LacCer(d18:1/20:0)/PC 16:0/20:3, LacCer(d18: 1/20:0)/PC 18:0/18:1, LacCer(d18:1/20:0)/PC 18:0/ 20:3 LacCer(d18:1/20:0)/PC 18:1/18:1, LacCer(d18:1/ 20:0)/PC 18:1/18:2, LacCer(d18:1/20:0)/PC 18:2/18:2, LacCer(d18:1/20:0)/SM (d18:1/17:1-OH), LacCer (d18:1/20:0)/SM (d18:1/18:0), LacCer(d18:1/20:0)/Total LPC, LacCer(d18:1/20:0)/Total PC, LacCer(d18:1/ 20:0)/Total SM, LacCer(d18:1/22:0)/PC 16:0/20:3, LacCer(d18:1/22:0)/PC 16:0/20:4, LacCer(d18:1/22: 0)/PC 18:0/20:3, LacCer(d18:1/22:0)/SM (d18:1/14:0) (d18:1/13:1-OH), LacCer(d18:1/22:0)/Total LPC, LacCer(d18:1/22:0)/Total PC, LacCer(d18:1/24:0)/PC 16:0/20:3, LacCer(d18:1/24:0)/Total LPC, LacCer (d18:1/24:1)/Total LPC, LacCer(d18:1/24:1)/Total PC, LacCer(d18:1/24:1)/Total PC O, PC 16:0/16:0/PC 16:0/20:4, PC 16:0/16:0/Total PC, PC 16:0/18:2/Total PC, PC O-18:0/18:2-alkyl/PC O-36:5, PC O-32:0 (KDdiA-PC)/PC O-38:5, PS O-16:0/18:2-alkenyl/Total PS O, PS O-16:1/18:2-alkyl/Total PS O, PS O-18:0/18:2-alkenyl (PS O-18:1/18:2-alkyl)/Total PS O, PS O-18: 2/16:0-alkenyl/Total PS O, Total Cer/Total PC, Total LacCer/Total PC and Total LacCer/Total PC O;

and wherein one or more lipid-lipid ratio(s) whose decrease is (are) compared to the control is (are) selected from (Tables 5a and 8a):

CE 14:0/Cer(d18:1/24:1), CE 16:0/Cer(d18:1/24:1), CE 16:1/CE 19:1, CE 16:1/Cer(d18:1/18:0), CE 16:1/Cer (d18:1/20:0), CE 16:1/Cer(d18:1/24:1), CE 16:1/GlcCer(d18:1/18:0), CE 16:1/GlcCer(d18:1/20:0), CE 16:1/LacCer(d18:1/16:0), CE 16:1/LacCer(d18:1/18: 0), CE 16:1/LacCer(d18:1/20:0), CE 16:1/LacCer(d18: 1/22:0), CE 16:1/LacCer(d18:1/24:0), CE 16:1/PC 16:0/16:0, CE 16:1/Total LacCer, CE 17:1/Cer(d18:1/ 24:1), CE 17:1/GlcCer(d18:1/24:1), CE 17:1/LacCer (d18:1/18:0), CE 18:1/Total LacCer, CE 18:3/Cer(d18: 1/16:0), CE 18:3/Cer(d18:1/18:0), CE 18:3/Cer(d18:1/ 20:0), CE 18:3/Cer(d18:1/22:0), CE 18:3/Cer(d18:1/ 24:0), CE 18:3/Cer(d18:1/24:1), CE 18:3/GlcCer(d18: 1/18:0), CE 18:3/GlcCer(d18:1/20:0), CE 18:3/LacCer (d18:1/18:0), CE 18:3/LacCer(d18:1/20:0), CE 18:3/ LacCer(d18:1/22:0), CE 18:3/LacCer(d18:1/24:0), CE 18:3/PC 16:0/16:0, CE 18:3/PC O-34:1, CE 18:3/PS O-16:0/18:1-alkenyl (PS O-16:1/18:1-alkyl), CE 18:3/ PS O-16:0/18:2-alkenyl, CE 18:3/PS O-16:1/18:2-alkyl, CE 18:3/Total CE, CE 18:3/Total Cer, CE 18:3/ Total LacCer, CE 20:3/Cer(d18:1/24:1), CE 20:3/ LacCer(d18:1/20:0), Cer(d18:0/22:0)/Cer(d18:1/18:0), Cer(d18:0/22:0)/Cer(d18:1/20:0), Cer(d18:0/22:0)/Cer (d18:1/22:0), Cer(d18:0/22:0)/Cer(d18:1/24:1), Cer (d18:0/22:0)/LacCer(d18:1/24:0), Cer(d18:0/22:0)/PS O-16:0/18:2-alkenyl, Cer(d18:0/22:0)/PS O-16:1/18:2-alkyl, Cer(d18:0/22:0)/Total CE, Cer(d18:0/24:0)/Cer (d18:1/16:0), Cer(d18:0/24:0)/Cer(d18:1/18:0), Cer (d18:0/24:0)/Cer(d18:1/20:0), Cer(d18:0/24:0)/Cer (d18:1/22:0), Cer(d18:0/24:0)/Cer(d18:1/24:1), Cer (d18:0/24:0)/GlcCer(d18:1/20:0), Cer(d18:0/24:0)/ LacCer(d18:1/24:0), Cer(d18:0/24:0)/PS O-16:0/18:2-alkenyl, Cer(d18:0/24:0)/PS O-16:1/18:2-alkyl, Cer (d18:0/24:0)/SM (d18:1/17:0) (d18:1/16:1-OH), Cer (d18:0/24:0)/Total CE, Cer(d18:0/24:0)/Total Cer, Cer (d18:0/24:1)/Total CE, GlcCer(d18:1/26:0)/LacCer (d18:1/20:0), GlcCer(d18:1/26:0)/LacCer(d18:1/22:0), LPC 16:0/LacCer(d18:1/20:0), LPC 16:0/LacCer(d18: 1/22:0), LPC 16:0/LacCer(d18:1/24:1), LPC 16:0/Total LacCer, LPC 18:1/LacCer(d18:1/20:0), LPC 18:2/LacCer(d18:1/20:0), LPC 18:2/PS O-16:0/18:2-alkenyl, LPC 18:2/PS O-16:1/18:2-alkyl, PC 16:0/20:3/PS O-16:0/18:2-alkenyl, PC 16:0/20:3/PS O-16:1/18:2-alkyl, PC 18:1/18:2/PS O-16:0/18:2-alkenyl, PC 18:1/18: 2/PS O-16:1/18:2-alkyl, SM (d18:1/24:0) (d18:1/23:1-OH)/Total Cer and Total LPC/Total LacCer.

In an alternative embodiment the invention relates to a method of choosing an appropriate treatment of CVD and/or one or more of its complications, such as AMI or CVD death, in a subject, wherein the subject is not undergoing statin treatment and wherein said method comprises determining in a sample from said subject one or more lipid-lipid ratio(s), wherein (an) increased or decreased lipid-lipid ratio(s) in said sample, when compared to a control sample, is (are) indicative of said subject being in need of treatment or a change in, or supplementation of, an already administered treatment, wherein the one or more lipid-lipid ratio(s) whose increase(s) is (are) compared to the control is (are) selected from (Tables 5b and 8b):

CE 16:0/CE 18:3, CE 18:0/CE 18:3, CE 18:2/CE 18:3, Cer(d18:1/16:0)/LPC 18:1, Cer(d18:1/16:0)/Total PC, Cer(d18:1/18:0)/LPC 18:1, Cer(d18:1/18:0)/PC 16:0/ 18:1, Cer(d18:1/18:0)/PC 16:0/20:3, Cer(d18:1/18:0)/ PC 16:0/20:4, Cer(d18:1/18:0)/PC 18:0/18:1, Cer(d18: 1/18:0)/PC 18:0/20:4, Cer(d18:1/18:0)/PC 18:1/18:1, Cer(d18:1/18:0)/SM (d18:1/14:0) (d18:1/13:1-OH), Cer(d18:1/18:0)/SM (d18:1/17:2-OH), Cer(d18:1/18: 0)/SM (d18:1/18:1), Cer(d18:1/18:0)/Total CE, Cer (d18:1/18:0)/Total LPC, Cer(d18:1/18:0)/Total PC, Cer (d18:1/20:0)/PC 16:0/18:1, Cer(d18:1/20:0)/PC 16:0/ 20:3, Cer(d18:1/20:0)/PC 16:0/20:4, Cer(d18:1/20:0)/ PC 18:0/18:1, Cer(d18:1/20:0)/PC 18:0/20:4, Cer(d18: 1/20:0)/PC 18:1/18:1, Cer(d18:1/20:0)/SM (d18:1/14: 0) (d18:1/13:1-OH), Cer(d18:1/20:0)/Total LPC, Cer (d18:1/20:0)/Total PC, Cer(d18:1/20:0)/Total PC O, Cer(d18:1/22:0)/LPC 18:2, Cer(d18:1/22:0)/PC 16:0/ 20:3, Cer(d18:1/22:0)/PC 16:0/20:4, Cer(d18:1/22:0)/ PC 18:0/20:4, Cer(d18:1/22:0)/Total PC, Cer(d18:1/24: 1)/LPC 18:1, Cer(d18:1/24:1)/LPC 18:2, Cer(d18:1/24: 1)/PC 16:0/18:1, Cer(d18:1/24:1)/PC 16:0/18:2, Cer (d18:1/24:1)/PC 16:0/20:3, Cer(d18:1/24:1)/PC 16:0/ 20:4, Cer(d18:1/24:1)/PC 18:0/18:1, Cer(d18:1/24:1)/ PC 18:0/18:2, Cer(d18:1/24:1)/PC 18:0/20:3, Cer(d18: 1/24:1)/PC 18:0/20:4, Cer(d18:1/24:1)/PC 18:1/18:1, Cer(d18:1/24:1)/PC 18:1/18:2, Cer(d18:1/24:1)/PC O-40:3, Cer(d18:1/24:1)/SM (d18:1/17:1-OH), Cer (d18:1/24:1)/SM (d18:1/18:0), Cer(d18:1/24:1)/SM (d18:1/23:0) (d18:1/22:1-OH), Cer(d18:1/24:1)/SM (d18:1/24:0) (d18:1/23:1-OH), Cer(d18:1/24:1)/Total CE, Cer(d18:1/24:1)/Total LPC, Cer(d18:1/24:1)/Total PC, GlcCer(d18:1/26:0)/Total CE, GlcCer(d18:1/26:1)/ Total CE, LacCer(d18:1/18:0)/Total PC, LacCer(d18: 1/20:0)/PC 16:0/20:3, LacCer(d18:1/20:0)/PC 16:0/20: 4, LacCer(d18:1/20:0)/PC 18:0/18:1, LacCer(d18:1/20: 0)/PC 18:0/20:3, LacCer(d18:1/20:0)/PC 18:0/20:4, LacCer(d18:1/20:0)/PC 18:1/18:2, LacCer(d18:1/20: 0)/SM (d18:1/17:1-OH), LacCer(d18:1/20:0)/SM (d18: 1/18:0), LacCer(d18:1/20:0)/Total CE, LacCer(d18:1/ 20:0)/Total LPC, LacCer(d18:1/20:0)/Total PC, LacCer (d18:1/20:0)/Total SM, LacCer(d18:1/24:0)/Total LPC, PC 16:0/16:0/PC 16:0/20:4, PC 16:0/16:0/Total PC, PC O-32:0 (KDdiA-PC)/Total PC O, PS O-16:0/18:2-alkenyl/Total PC, PS O-16:0/18:2-alkenyl/Total PC o, PS O-16:0/18:2-alkenyl/Total PS O, PS O-16:1/18:2-alkyl/ Total PC, PS O-16:1/18:2-alkyl/Total PC O, PS O-16: 1/18:2-alkyl/Total PS O, PS O-18:2/16:0-alkenyl/Total PC O, PS O-18:2/16:0-alkenyl/Total PS O, SM (d18:1/17:0) (d18:1/16:1-OH)/Total PC O, Total Cer/ Total PC, Total DAG/Total LPC, Total DAG/Total PC, Total DAG/Total PC O and Total LacCer/Total PC;

and wherein the one or more lipid-lipid ratio(s) whose decrease(s) is (are) compared to the control is (are) selected from (Tables 5b and 8b):

CE 14:0/Cer(d18:1/18:0), CE 14:0/Cer(d18:1/24:1), CE 14:0/Total DAG, CE 15:0/Cer(d18:1/20:0), CE 16:0/ Cer(d18:1/18:0), CE 16:0/Cer(d18:1/24:1), CE 16:1/ CE 19:1, CE 16:1/Cer(d18:1/18:0), CE 16:1/Cer(d18: 1/20:0), CE 16:1/Cer(d18:1/24:1), CE 16:1/GlcCer (d18:1/24:1), CE 16:1/LacCer(d18:1/18:0), CE 16:1/ LacCer(d18:1/24:0), CE 16:1/Total LacCer, CE 17:1/ Cer(d18:1/18:0), CE 17:1/Cer(d18:1/24:1), CE 18:2/ Cer(d18:1/20:0), CE 18:2/Cer(d18:1/24:1), CE 18:3/ Cer(d18:1/16:0), CE 18:3/Cer(d18:1/18:0), CE 18:3/ Cer(d18:1/20:0), CE 18:3/Cer(d18:1/22:0), CE 18:3/ Cer(d18:1/24:0), CE 18:3/Cer(d18:1/24:1), CE 18:3/ GlcCer(d18:1/20:0), CE 18:3/LacCer(d18:1/20:0), CE 18:3/LacCer(d18:1/22:0), CE 18:3/LacCer(d18:1/24: 0), CE 18:3/PC 16:0/16:0, CE 18:3/PC O-34:1, CE 18:3/PS O-16:0/18:2-alkenyl, CE 18:3/PS O-16:1/18: 2-alkyl, CE 18:3/Total CE, CE 18:3/Total Cer, CE 18:3/Total DAG, CE 18:3/Total LacCer, CE 20:3/Cer (d18:1/24:1), CE 20:3/LacCer(d18:1/20:0), CE 20:4/ Cer(d18:1/18:0), CE 20:4/Cer(d18:1/24:1), CE 20:4/ GlcCer(d18:1/20:0), CE 20:4/GlcCer(d18:1/24:1), CE 20:4/LacCer(d18:1/20:0), CE 20:5/LacCer(d18:1/20: 0), Cer(d18:0/22:0)/Cer(d18:1/18:0), Cer(d18:0/22:0)/ Cer(d18:1/20:0), Cer(d18:0/22:0)/Cer(d18:1/24:1), Cer (d18:0/22:0)/PS O-16:0/18:2-alkenyl, Cer(d18:0/22:0)/ PS O-16:1/18:2-alkyl, Cer(d18:0/22:0)/Total CE, Cer (d18:0/22:0)/Total DAG, Cer(d18:0/22:0)/Total GicCer, Cer(d18:0/24:0)/Cer(d18:1/18:0), Cer(d18:0/ 24:0)/Cer(d18:1/20:0), Cer(d18:0/24:0)/Cer(d18:1/24: 1), Cer(d18:0/24:0)/PS O-16:0/18:2-alkenyl, Cer(d18: 0/24:0)/PS O-16:1/18:2-alkyl, Cer(d18:0/24:0)/Total CE, Cer(d18:0/24:0)/Total Cer, DAG 16:0/18:1/Total DAG, GlcCer(d18:1/26:0)/LacCer(d18:1/20:0), LPC 16:0/LacCer(d18:1/24:0), LPC 18:1/LacCer(d18:1/20: 0), LPC 18:2/LacCer(d18:1/20:0), PC 16:0/20:3/PS O-16:0/18:2-alkenyl, PC 16:0/20:3/PS O-16:1/18:2-alkyl, PC 16:0/20:4/PS O-16:0/18:2-alkenyl, PC 16:0/20: 4/PS O-16:1/18:2-alkyl, PC 16:0/20:4/Total DAG, PC 18:0/20:3/PS O-16:0/18:2-alkenyl, PC 18:0/20:3/PS O-16:1/18:2-alkyl, PC 18:0/20:3/PS O-18:2/16:0-alkenyl, PC 18:0/20:4/PS O-16:0/18:2-alkenyl, PC 18:0/ 20:4/PS O-16:1/18:2-alkyl, PC 18:1/18:2/PS O-16:0/ 18:2-alkenyl, PC 18:1/18:2/PS O-16:1/18:2-alkyl, PC 18:1/18:2/Total Cer, PC O-40:3/PS O-18:2/16:0-alkenyl, SM (d18:1/23:0) (d18:1/22:1-OH)/Total DAG, SM (d18:1/24:0) (d18:1/23:1-OH)/Total Cer, Total CE/Total DAG and Total LPC/Total LacCer.

In a preferred embodiment (for subjects that are either undergoing or not undergoing statin treatment), the one or more lipid-lipid ratio(s) whose increase is (are) compared to the control is (are) selected from (Table 11):

GlcCer(d18:1/26:1)/Total CE, Cer(d18:1/24:1)/Total PC, Cer(d18:1/24:1)/PC 16:0/20:4, Cer(d18:1/20:0)/PC 16:0/20:4, LacCer(d18:1/20:0)/PC 16:0/20:3, Total Cer/Total PC, Total LacCer/Total PC, LacCer(d18:1/ 20:0)/PC 18:1/18:2, PS O-16:0/18:2-alkenyl/Total PS O, Cer(d18:1/18:0)/PC 16:0/20:4, LacCer(d18:1/20:0)/ Total LPC and LacCer(d18:1/20:0)/PC 16:0/20:4;

In another preferred embodiment, the one or more lipid-lipid ratio(s) whose decrease is (are) compared to the control is (are) selected from (Table 11):

Cer(d18:0/24:0)/Cer(d18:1/24:1), Cer(d18:0/22:0)/Cer (d18:1/24:1), DAG 16:0/18:1/Total DAG, Cer(d18:0/ 24:0)/Cer(d18:1/22:0), Cer(d18:0/24:0)/Total CE, Cer (d18:0/24:0)/Cer(d18:1/24:1), Cer(d18:0/24:0)/Total Cer, Cer(d18:0/24:0)/Cer(d18:1/18:0), Cer(d18:0/24: 0)/PS O-16:0/18:2-alkenyl, Cer(d18:0/24:0)/LacCer (d18:1/24:0), Cer(d18:0/22:0)/Cer(d18:1/18:0), Cer (d18:0/24:0)/Cer(d18:1/22:0), Cer(d18:0/22:0)/Cer (d18:1/20:0), Cer(d18:0/22:0)/PS O-16:0/18:2-alkenyl, Cer(d18:0/22:0)/PS O-16:1/18:2-alkyl, GlcCer(d18:1/ 26:0)/LacCer(d18:1/20:0), Total LPC/Total LacCer and GlcCer(d18:1/26:0)/LacCer(d18:1/22:0).

In a particularly preferred embodiment, the one or more lipid-lipid ratio(s) whose increase is (are) compared to the control is (are) selected from (Table 13):

Cer(d18:1/24:1)/PC 16:0/20:4, LacCer(d18:1/20:0)/PC 16:0/20:3, PS O-16:0/18:2-alkenyl/Total PS 0 and Cer (d18:1/18:0)/PC 16:0/20:4;

and the one or more lipid-lipid ratio(s) whose decrease is (are) compared to the control is (are) selected from (Table 13):

GlcCer(d18:1/26:0)/LacCer(d18:1/20:0), DAG 16:0/18: 1/Total DAG, Cer(d18:0/24:0)/Total Cer, Total LPC/ Total LacCer, GlcCer(d18:1/26:0)/LacCer(d18:1/22:0), Cer(d18:0/24:0)/Cer(d18:1/24:1), Cer(d18:0/24:0)/Cer (d18:1/18:0), Cer(d18:0/24:0)/PS O-16:0/18:2-alkenyl, Cer(d18:0/24:0)/Cer(d18:1/22:0), Cer(d18:0/22:0)/PS O-16:0/18:2-alkenyl, Cer(d18:0/22:0)/PS O-16:1/18:2-alkyl and Cer(d18:0/24:0)/LacCer(d18:1/24:0). In yet another embodiment the invention relates to a method of choosing an appropriate treatment of CVD and/or one or more of its complications, such as AMI or CVD death, in a subject, comprising determining in a sample from said subject one or more lipid-clinical concentration ratio(s), wherein (an) increased or decreased lipid-clinical concentration ratio(s) in said sample, when compared to a control sample, is (are) indicative of said subject being in need of treatment or a change in, or supplementation of, an already administered treatment, wherein the one or more lipid-clinical concentration ratio(s) whose increase is (are) compared to the control is (are) selected from (Tables 6a and 9a):

Cer(d18:1/16:0)/triglycerides (EDTA) (mg/dL), Cer(d18: 1/18:0)/apolipoprotein A-I (mg/dL), Cer(d18:1/18:0)/ apolipoprotein B (mg/dL), Cer(d18:1/18:0)/HDL cholesterol (EDTA) (mg/dL), Cer(d18:1/18:0)/total cholesterol (EDTA) (mg/dL), Cer(d18:1/18:0)/total-c/ HDL-c, Cer(d18:1/18:0)/triglycerides (EDTA) (mg/ dL), Cer(d18:1/20:0)/apolipoprotein A-I (mg/dL), Cer (d18:1/20:0)/apolipoprotein B (mg/dL), Cer(d18:1/20: 0)/HDL cholesterol (EDTA) (mg/dL), Cer(d18:1/20:0)/ total cholesterol (EDTA) (mg/dL), Cer(d18:1/20:0)/ triglycerides (EDTA) (mg/dL), Cer(d18:1/22:0)/ apolipoprotein B (mg/dL), Cer(d18:1/22:0)/LDL cholesterol (EDTA) (mg/dL), Cer(d18:1/22:0)/triglycerides (EDTA) (mg/dL), Cer(d18:1/24:1)/apolipoprotein A-I (mg/dL), Cer(d18:1/24:1)/apolipoprotein B (mg/dL), Cer(d18:1/24:1)/LDL cholesterol (EDTA) (mg/dL), Cer(d18:1/24:1)/total cholesterol (EDTA) (mg/dL), Cer(d18:1/24:1)/total-c/HDL-c, Cer(d18:1/ 24:1)/triglycerides (EDTA) (mg/dL), GlcCer(d18:1/24: 0)/total cholesterol (EDTA) (mg/dL), LacCer(d18:1/

16:0)/triglycerides (EDTA) (mg/dL), LacCer(d18:1/18:0)/apolipoprotein A-I (mg/dL), LacCer(d18:1/18:0)/apolipoprotein B (mg/dL), LacCer(d18:1/18:0)/HDL cholesterol (EDTA) (mg/dL), LacCer(d18:1/18:0)/LDL cholesterol (EDTA) (mg/dL), LacCer(d18:1/18:0)/total cholesterol (EDTA) (mg/dL), LacCer(d18:1/18:0)/total-c/HDL-c, LacCer(d18:1/18:0)/triglycerides (EDTA) (mg/dL), LacCer(d18:1/20:0)/apoA1/apoB, LacCer(d18:1/20:0)/apolipoprotein A-I (mg/dL), LacCer(d18:1/20:0)/apolipoprotein B (mg/dL), LacCer(d18:1/20:0)/HDL cholesterol (EDTA) (mg/dL), LacCer(d18:1/20:0)/LDL cholesterol (EDTA) (mg/dL), LacCer(d18:1/20:0)/LDL-c/HDL-c, LacCer(d18:1/20:0)/total cholesterol (EDTA) (mg/dL), LacCer(d18:1/20:0)/total-c/HDL-c, LacCer(d18:1/20:0)/triglycerides (EDTA) (mg/dL), LacCer(d18:1/22:0)/apoA1/apoB, LacCer(d18:1/22:0)/apolipoprotein A-I (mg/dL), LacCer(d18:1/22:0)/apolipoprotein B (mg/dL), LacCer(d18:1/22:0)/HDL cholesterol (EDTA) (mg/dL), LacCer(d18:1/22:0)/LDL cholesterol (EDTA) (mg/dL), LacCer(d18:1/22:0)/total cholesterol (EDTA) (mg/dL), LacCer(d18:1/22:0)/total-c/HDL-c, LacCer(d18:1/22:0)/triglycerides (EDTA) (mg/dL), LacCer(d18:1/24:0)/apoA1/apoB, LacCer(d18:1/24:1)/apolipoprotein A-I (mg/dL), LacCer(d18:1/24:1)/apolipoprotein B (mg/dL), LacCer(d18:1/24:1)/total cholesterol (EDTA) (mg/dL), LacCer(d18:1/24:1)/triglycerides (EDTA) (mg/dL), PC O-32:0 (KDdiA-PC)/apolipoprotein A-I (mg/dL), P C O-32:0 (KDdiA-PC)/triglycerides (EDTA) (mg/dL), PC O-34:1/triglycerides (EDTA) (mg/dL), PS O-16:0/18:1-alkenyl (PS O-16:1/18:1-alkyl)/triglycerides (EDTA) (mg/dL), PS O-16:0/18:2-alkenyl/triglycerides (EDTA) (mg/dL), PS O-16:1/18:2-alkyl/triglycerides (EDTA) (mg/dL), PS O-18:2/16:0-alkenyl/HDL cholesterol (EDTA) (mg/dL), PS O-18:2/16:0-alkenyl/triglycerides (EDTA) (mg/dL), Total Cer/apolipoprotein A-I (mg/dL), Total Cer/total cholesterol (EDTA) (mg/dL), Total Cer/triglycerides (EDTA) (mg/dL), Total GlcCer/apolipoprotein B (mg/dL), Total GlcCer/total cholesterol (EDTA) (mg/dL), Total LacCer/apolipoprotein A-I (mg/dL), Total LacCer/apolipoprotein B (mg/dL), Total LacCer/total cholesterol (EDTA) (mg/dL) and Total LacCer/triglycerides (EDTA) (mg/dL);

and wherein the one or more lipid-clinical concentration ratio(s) whose decrease is (are) compared to the control is (are) selected from (Tables 6a and 9a):

CE 14:0/apolipoprotein B (mg/dL), CE 14:0/LDL cholesterol (EDTA) (mg/dL), CE 14:0/LDL-c/HDL-c, CE 14:0/total cholesterol (EDTA) (mg/dL), CE 14:0/total-c/HDL-c, CE 16:1/apolipoprotein B (mg/dL), CE 16:1/HDL cholesterol (EDTA) (mg/dL), CE 16:1/LDL cholesterol (EDTA) (mg/dL), CE 16:1/total cholesterol (EDTA) (mg/dL), CE 17:1/LDL-c/HDL-c, CE 18:3/apoA1/apoB, CE 18:3/apolipoprotein A-I (mg/dL), CE 18:3/apolipoprotein B (mg/dL), CE 18:3/HDL cholesterol (EDTA) (mg/dL), CE 18:3/LDL cholesterol (EDTA) (mg/dL), CE 18:3/LDL-c/HDL-c, CE 18:3/total cholesterol (EDTA) (mg/dL), CE 18:3/total-c/HDL-c, CE 20:3/apolipoprotein B (mg/dL), CE 20:3/LDL-c/HDL-c, CE 20:3/total-c/HDL-c, CE 20:5/apolipoprotein B (mg/dL), CE 20:5/HDL cholesterol (EDTA) (mg/dL), CE 20:5/LDL cholesterol (EDTA) (mg/dL), Cer(d18:0/22:0)/apolipoprotein B (mg/dL), Cer(d18:0/22:0)/LDL-c/HDL-c, Cer(d18:0/22:0)/total-c/HDL-c, Cer(d18:0/24:0)/apolipoprotein A-I (mg/dL), Cer(d18:0/24:0)/apolipoprotein B (mg/dL), Cer(d18:0/24:0)/HDL cholesterol (EDTA) (mg/dL), Cer(d18:0/24:0)/LDL cholesterol (EDTA) (mg/dL), Cer(d18:0/24:0)/LDL-c/HDL-c, Cer(d18:0/24:0)/total cholesterol (EDTA) (mg/dL), Cer(d18:0/24:0)/total-c/HDL-c, LPC 18:2/apoA1/apoB, LPC 18:2/apolipoprotein B (mg/dL), LPC 18:2/HDL cholesterol (EDTA) (mg/dL), LPC 18:2/LDL cholesterol (EDTA) (mg/dL), LPC 18:2/LDL-c/HDL-c, LPC 18:2/total cholesterol (EDTA) (mg/dL), PC 16:0/20:3/apolipoprotein B (mg/dL), PC 16:0/20:3/HDL cholesterol (EDTA) (mg/dL), PC 16:0/20:3/LDL-c/HDL-c, PC 16:0/20:3/total-c/HDL-c, PC 16:0/20:4/apolipoprotein A-I (mg/dL), PC 16:0/20:4/apolipoprotein B (mg/dL), PC 16:0/20:4/LDL cholesterol (EDTA) (mg/dL), PC 16:0/20:4/LDL-c/HDL-c, PC 16:0/20:4/total cholesterol (EDTA) (mg/dL), PC 16:0/20:4/total-c/HDL-c, PC 18:0/18:1/LDL-c/HDL-c, PC 18:0/20:3/LDL-c/HDL-c, PC 18:0/20:3/total-c/HDL-c, PC 18:0/20:4/apoA1/apoB, Total LPC/LDL-c/HDL-c, Total LPC/total-c/HDL-c, Total PC/apolipoprotein B (mg/dL), Total PC/LDL-c/HDL-c, Total PC/total cholesterol (EDTA) (mg/dL) and Total PC/total-c/HDL-c.

In yet another embodiment the invention relates to a method of choosing an appropriate treatment of CVD and/or one or more of its complications, such as AMI or CVD death, in a subject, wherein the subject is not undergoing statin treatment and wherein said method comprises determining in a sample from said subject one or more lipid-clinical concentration ratio(s), wherein (an) increased or decreased lipid-clinical concentration ratio(s) in said sample, when compared to a control sample, is (are) indicative of said subject being in need of treatment or a change in, or supplementation of, an already administered treatment, wherein the one or more lipid-clinical concentration ratio(s) whose increase is (are) compared to the control is (are) selected from (Tables 6b and 9b):

Cer(d18:1/16:0)/apolipoprotein A-I (mg/dL), Cer(d18:1/16:0)/LDL cholesterol (EDTA) (mg/dL), Cer(d18:1/16:0)/triglycerides (EDTA) (mg/dL), Cer(d18:1/18:0)/apolipoprotein A-I (mg/dL), Cer(d18:1/18:0)/apolipoprotein B (mg/dL), Cer(d18:1/18:0)/HDL cholesterol (EDTA) (mg/dL), Cer(d18:1/18:0)/total cholesterol (EDTA) (mg/dL), Cer(d18:1/18:0)/total-c/HDL-c, Cer(d18:1/18:0)/triglycerides (EDTA) (mg/dL), Cer(d18:1/20:0)/apolipoprotein A-I (mg/dL), Cer(d18:1/20:0)/apolipoprotein B (mg/dL), Cer(d18:1/20:0)/HDL cholesterol (EDTA) (mg/dL), Cer(d18:1/20:0)/LDL cholesterol (EDTA) (mg/dL), Cer(d18:1/20:0)/total cholesterol (EDTA) (mg/dL), Cer(d18:1/20:0)/total-c/HDL-c, Cer(d18:1/20:0)/triglycerides (EDTA) (mg/dL), Cer(d18:1/22:0)/apolipoprotein A-I (mg/dL), Cer(d18:1/22:0)/apolipoprotein B (mg/dL), Cer(d18:1/22:0)/LDL cholesterol (EDTA) (mg/dL), Cer(d18:1/22:0)/total cholesterol (EDTA) (mg/dL), Cer(d18:1/22:0)/triglycerides (EDTA) (mg/dL), Cer(d18:1/24:0)/apolipoprotein A-I (mg/dL), Cer(d18:1/24:0)/apolipoprotein B (mg/dL), Cer(d18:1/24:0)/LDL cholesterol (EDTA) (mg/dL), Cer(d18:1/24:0)/total cholesterol (EDTA) (mg/dL), Cer(d18:1/24:1)/apolipoprotein A-I (mg/dL), Cer(d18:1/24:1)/apolipoprotein B (mg/dL), Cer(d18:1/24:1)/HDL cholesterol (EDTA) (mg/dL), Cer(d18:1/24:1)/LDL cholesterol (EDTA) (mg/dL), Cer(d18:1/24:1)/LDL-c/HDL-c, Cer(d18:1/24:1)/total cholesterol (EDTA) (mg/dL), Cer(d18:1/24:1)/total-c/HDL-c, Cer(d18:1/24:1)/triglycerides (EDTA) (mg/dL), GlcCer(d18:1/20:0)/apolipoprotein B (mg/dL), GlcCer(d18:1/20:0)/total cholesterol (EDTA) (mg/dL), GlcCer(d18:1/24:1)/apolipoprotein B (mg/dL), GlcCer(d18:1/26:1)/apolipoprotein A-I (mg/dL), LacCer(d18:1/16:0)/triglycerides (EDTA) (mg/dL), LacCer(d18:1/18:0)/apolipoprotein A-I (mg/dL), LacCer(d18:1/18:0)/apolipoprotein B (mg/dL), LacCer(d18:1/18:0)/total cholesterol (EDTA) (mg/dL), LacCer(d18:1/20:0)/apoA1/apoB, LacCer(d18:1/20:0)/apolipoprotein A-I (mg/dL), LacCer(d18:1/20:0)/apolipoprotein B (mg/dL), LacCer(d18:1/20:0)/HDL cholesterol (EDTA) (mg/dL), LacCer(d18:1/20:0)/LDL cholesterol (EDTA) (mg/dL), LacCer(d18:1/20:0)/LDL-c/HDL-c, LacCer(d18:1/20:0)/total cholesterol (EDTA) (mg/dL), LacCer(d18:1/20:0)/total-c/HDL-c, LacCer(d18:1/20:0)/triglycerides (EDTA) (mg/dL), LacCer(d18:1/22:0)/apoA1/apoB, LacCer(d18:1/22:0)/apolipoprotein A-I (mg/dL), LacCer(d18:1/22:0)/apolipoprotein B (mg/dL), LacCer(d18:1/22:0)/HDL cholesterol (EDTA) (mg/dL), LacCer(d18:1/22:0)/LDL cholesterol (EDTA) (mg/dL), LacCer(d18:1/22:0)/total cholesterol (EDTA) (mg/dL), LacCer(d18:1/24:1)/apolipoprotein A-I (mg/dL), LacCer(d18:1/24:1)/apolipoprotein B (mg/dL), LacCer(d18:1/24:1)/total cholesterol (EDTA) (mg/dL), LacCer(d18:1/24:1)/triglycerides (EDTA) (mg/dL), PC O-34:1/apolipoprotein B (mg/dL), PS O-16:0/18:2-alkenyl/triglycerides (EDTA) (mg/dL), PS O-16:1/18:2-alkyl/triglycerides (EDTA) (mg/dL), Total Cer/apolipoprotein A-I (mg/dL), Total Cer/apolipoprotein B (mg/dL), Total Cer/LDL cholesterol (EDTA) (mg/dL), Total Cer/total cholesterol (EDTA) (mg/dL), Total DAG/apolipoprotein A-I (mg/dL), Total DAG/triglycerides (EDTA) (mg/dL), Total GicCer/apolipoprotein B (mg/dL), Total LacCer/apolipoprotein A-I (mg/dL), Total LacCer/apolipoprotein B (mg/dL) and Total LacCer/total cholesterol (EDTA) (mg/dL).

and wherein the one or more lipid-clinical concentration ratio(s) whose decrease is (are) compared to the control is (are) selected from (Tables 6b and 9b):
CE 14:0/apoA1/apoB, CE 14:0/apolipoprotein B (mg/dL), CE 14:0/LDL-c/HDL-c, CE 14:0/total-c/HDL-c, CE 16:1/apoA1/apoB, CE 18:3/apoA1/apoB, CE 18:3/apolipoprotein A-I (mg/dL), CE 18:3/apolipoprotein B (mg/dL), CE 18:3/HDL cholesterol (EDTA) (mg/dL), CE 18:3/LDL cholesterol (EDTA) (mg/dL), CE 18:3/LDL-c/HDL-c, CE 18:3/total cholesterol (EDTA) (mg/dL), CE 18:3/total-c/HDL-c, CE 20:5/triglycerides (EDTA) (mg/dL), Cer(d18:0/24:0)/apolipoprotein B (mg/dL), Cer(d18:0/24:0)/total cholesterol (EDTA) (mg/dL), Cer(d18:0/24:0)/total-c/HDL-c, PC 18:0/20:4/apoA1/apoB, PC O-38:6/apolipoprotein A-I (mg/dL), Total LPC/apoA1/apoB and Total PC/apolipoprotein A-I (mg/dL).

In a preferred embodiment (for subjects that are either undergoing or not undergoing statin treatment), the one or more lipid-clinical concentration ratio(s) whose increase is (are) compared to the control is (are) selected from (Table 12):
Cer(d18:1/20:0)/apolipoprotein A-I (mg/dL), Cer(d18:1/24:1)/apolipoprotein A-I (mg/dL), LacCer(d18:1/20:0)/apolipoprotein A-I (mg/dL), Total Cer/apolipoprotein A-I (mg/dL), Total LacCer/apolipoprotein A-I (mg/dL), Cer(d18:1/18:0)/apolipoprotein A-I (mg/dL), LacCer(d18:1/22:0)/apolipoprotein A-I (mg/dL), LacCer(d18:1/20:0)/HDL cholesterol (EDTA) (mg/dL) and Cer(d18:1/24:1)/apolipoprotein B (mg/dL).

In another preferred embodiment, the one or more lipid-clinical concentration ratio(s) whose decrease is (are) compared to the control is (are) selected from (Table 12):
Cer(d18:0/24:0)/apolipoprotein B (mg/dL), Cer(d18:0/24:0)/total cholesterol (EDTA) (mg/dL), Cer(d18:0/24:0)/apolipoprotein B (mg/dL), PC 16:0/20:4/apolipoprotein B (mg/dL) and Cer(d18:0/24:0)/apolipoprotein A-I (mg/dL).

In a particularly preferred embodiment, the one or more lipid-clinical concentration ratio(s) whose increase is (are) compared to the control is (are) selected from (Table 13):
Cer(d18:1/20:0)/apolipoprotein A-I (mg/dL), Cer(d18:1/24:1)/apolipoprotein A-I (mg/dL), LacCer(d18:1/20:0)/apolipoprotein A-I (mg/dL), Total LacCer/apolipoprotein A-I (mg/dL), LacCer(d18:1/20:0)/HDL cholesterol (EDTA) (mg/dL) and Cer(d18:1/18:0)/apolipoprotein A-I (mg/dL).

For the purposes of the invention, and particularly for lipid-clinical concentration ratios, an Apolipoprotein A-I measurement may alternatively be an Apolipoprotein A-II measurement.

Claim 5In one embodiment of the invention, the treatment the effectiveness of which is to be evaluated or which is to be chosen as appropriate in accordance with the methods described and claimed herein, is a lipid modifying treatment.

Claim 7For the purposes of the invention, at least one lipid concentration, lipid-lipid ratio or lipid-clinical concentration ratio from Tables 4-13, or combinations thereof, may be determined to assess whether the patient is at risk to develop one or more of CVD complications such as AMI or CVD death; to evaluate the effectiveness of the treatment of CVD and/or one or more of its complications, such as AMI or CVD death in a subject; or to choose an appropriate treatment of CVD and/or one or more of its complications, such as AMI or CVD death in a subject. However, it is also possible, and may be advantageous, to determine at least 2, at least 3, at least 4, at least 5, at least 6, at least 7, or at least 8 lipid concentrations, lipid-lipid ratios or lipid-clinical concentration ratios from Tables 4-13, or combinations thereof, in this regard. Where more than one lipidomic markers are determined and used for the assessment, it may be advantageous that a specific lipid concentration, lipid-lipid ratio, lipid-clinical concentration ratio or combination thereof, is given greater weight than others in the above-mentioned assessment, evaluation or choice.

Preferred embodiments of the invention are methods wherein the one or more lipid(s) or lipid ratio(s), or combination thereof, comprise(s): (particularly preferred lipid species and ratios in claim 6) Cer(d18:1/20:0), LacCer(d18:1/20:0), Cer(d18:1/24:1), LacCer(d18:1/24:1), LacCer(d18:1/22:0), Cer(d18:1/18:0), PC 16:0/20:4, Cer(d18:0/24:0), Cer(d18:1/24:1)/PC 16:0/20:4, LacCer(d18:1/20:0)/PC 16:0/20:3, PS O-16:0/18:2-alkenyl/Total PS O, Cer(d18:1/18:0)/PC 16:0/20:4, GlcCer(d18:1/26:0)/LacCer(d18:1/20:0), DAG 16:0/18:1/Total DAG, Cer(d18:0/24:0)/Total Cer, Total LPC/Total LacCer, GlcCer(d18:1/26:0)/LacCer(d18:1/22:0), Cer(d18:0/24:0)/Cer(d18:1/24:1), Cer(d18:0/24:0)/Cer(d18:1/18:0), Cer(d18:0/24:0)/PS O-16:0/18:2-alkenyl, Cer(d18:0/24:0)/Cer(d18:1/22:0), Cer(d18:0/22:0)/PS O-16:0/18:2-alkenyl, Cer(d18:0/22:0)/PS O-16:1/18:2-alkyl, Cer(d18:0/24:0)/LacCer(d18:1/24:0), Cer(d18:1/20:0)/apolipoprotein A-I (mg/dL), Cer(d18:1/24:1)/apolipoprotein A-I (mg/dL), LacCer(d18:1/20:0)/apolipoprotein A-I (mg/dL), Total LacCer/apolipoprotein A-I (mg/dL), LacCer(d18:1/20:0)/HDL cholesterol (EDTA) (mg/dL) and Cer(d18:1/18:0)/apolipoprotein A-I (mg/dL).

In the context of the present invention, CVD is typically characterized by coronary artery disease, peripheral artery disease, a stroke and/or CVD death. The CVD in the subject whose sample is analyzed in accordance with the invention may be atherosclerosis-induced. However, the invention also embodies methods involving subjects who are at risk of developing CVD, but who may or may not have atherosclerosis.

In a further embodiment, the methods of the invention may further comprise determining the serum level of total cholesterol, low-density lipoprotein cholesterol (LDL-C), high-density lipoprotein cholesterol (HDL-C), Apolipoprotein B (ApoB) and/or Apolipoprotein C-III in the subject's sample. In one embodiment of the invention, the subject does not have elevated serum levels of one or more of total cholesterol, low-density lipoprotein cholesterol (LDL-C), Apolipoprotein C-III or Apolipoprotein B (ApoB), or a decreased serum level of HDL-cholesterol (HDL-C).

As mentioned above, for the purposes of the present invention, a control sample may be obtained from (a) CAD patient(s) or a group of CAD patients that has/have remained free of any major CVD complications e.g., by mixing a variety of samples from said population. If a group of CAD patients is used then several lipid profiles from a population are combined and the lipidomic marker is created from this combination. The levels or amounts of the individual lipids or the lipid-lipid ratios or lipid-clinical concentration ratios in the sample from a subject are compared to the levels or amounts of the lipids or lipid ratios in the control for determining the risk of one or more of CVD complications, such as AMI or CVD death, in said subject.

The invention encompasses the analysis of lipid concentrations, lipid-lipid ratios and/or lipid-clinical concentration ratios in samples from a subject that has been or is being treated with one or more statins and/or any other HMG-CoA reductase inhibitor.

Alternatively, the invention encompasses the analysis of lipid concentrations, lipid-lipid ratios and/or lipid-clinical concentration ratios in samples from a subject that has not yet undergone statin therapy or therapy with any other HMG-CoA reductase inhibitor.

In accordance with the aspects and embodiments of the invention described and claimed herein, the statin may be one selected from the group consisting of atorvastatin, cerivastatin, fluvastatin, fluvastatin XL, lovastatin, pitavastatin, pravastatin, rosuvastatin, and simvastatin.

Collecting information on a lipidomic marker or a lipidomic profile from a subject's biological sample can be performed via various chemical and high resolution analytical techniques. Suitable analytical techniques include but are not limited to mass spectrometry and nuclear resonance spectroscopy. Any high resolution technique capable of resolving individual lipids or lipid classes and providing structural information of the same can be used to collect the lipid profile from the biological sample. For methods of the present invention the level of the lipid is determined by using mass spectrometry, nuclear magnetic resonance spectroscopy, fluorescence spectroscopy or dual polarisation interferometry, a high performance separation method such as HPLC or UPLC and/or an immunoassay such as an ELISA. According to an alternative or further embodiment an analyte in a sample can be detected and/or quantified by combining the analyte with a binding moiety capable of specifically binding the analyte. The binding moiety can include, for example, a member of a ligand-receptor pair, i.e., a pair of molecules capable of having a specific binding interaction. The binding moiety can also include, for example, a member of a specific binding pair, such as antibody-antigen, enzyme-substrate, nucleic acid-based ligands, other protein ligands, or other specific binding pairs known in the art. In a preferred embodiment, the lipidomic profile is collected with mass spectrometry (MS), wherein the MS instrument may be coupled to direct infusion methods and high performance separation methods such as HPLC or HPLC. The amount of the individual lipids or lipid classes in the collected lipidomic profile is used when comparing the collected lipid profile to a control.

The methods of the present invention may be used for determining a risk of said patient to develop CVD complications, particularly severe CVD complications such as death and myocardial infarction (MI), including acute myocardial infarction (AMI).

In one embodiment of the invention, a method for treating or preventing CVD complications, such as AMI or CVD death, in a subject in need thereof is provided. The method comprises administering a therapeutically effective dose of a drug capable of modulating one or more of the lipid concentration(s), lipid-lipid ratio(s) or lipid-clinical concentration ratio(s) described in Tables 4-13, wherein the dose is such that said one or more lipid concentration(s), lipid-lipid ratio(s) or lipid-clinical concentration ratio(s) in a sample of said subject does not significantly change when compared to (a) corresponding lipid concentration(s), (a) corresponding lipid-lipid ratio(s) or (a) corresponding lipid-clinical concentration ratio(s) in a control, e.g., a control sample. In a preferred embodiment, the drug is a statin or another HMG CoA reductase inhibitor. Particularly preferred statins in this regard are atorvastatin, cerivastatin, fluvastatin, fluvastatin XL, lovastatin, pitavastatin, pravastatin, rosuvastatin or simvastatin. In another preferred embodiment, the drug is niacin (nicotinic acid); a cholesterol absorption inhibitor, such as ezetimibe or SCH-48461; a cholesteryl ester transfer protein (CETP) inhibitor, such as torcetrapib, anacetrapib or JTT-705; a bile acids sequestrant, such as colesevelam, cholestyramine and colestipol; or a fibrate, such as fenofibrate, gemfibrozil, clofibrate, and bezafibrate. Alternatively, it may also be a phytosterol.

Also embodied by the present invention is a lipid as described herein, e.g. a lipid from any of Tables 4, 7, 10 or 13, for use in preventing or treating a subject at risk to develop CVD complications such as AMI or CVD death, wherein the said lipid is to be taken as a dietary supplement or a medicament. A corresponding method of treatment is likewise encompassed. Likewise, the invention also encompasses a modulator for use for modulating a lipid concentration, lipid-lipid ratio or lipid-clinical concentration ratio as described herein, e.g., in Tables 4-13, in a subject at risk to develop CVD and/or one or more of its complications such as AMI or CVD death. A corresponding method of treatment is likewise encompassed. In a further embodiment, the said modulator is a small molecule, an antisense RNA, a small interfering RNA (siRNA) or a natural or modified lipid.

In one embodiment of the present invention, an antibody against any one of the lipids in Tables 4-13 is used for predicting one or more CVD complications such as AMI or CVD death. In another embodiment of the invention, the antibody may be used for preventing or treating one or more of the above complications in a subject.

Any of the methods, drugs, lipids or antibodies of the present invention may be used for a subject which is at risk to develop or has suffered from one or more CVD complications such as acute myocardial infarction and/or a cardiovascular death. For the purposes of the invention, CVD complication(s) includes severe CVD complication(s), particularly death.

Also encompassed by the present invention is a kit for predicting CVD complications or for performing any of the methods or uses of the present invention, wherein the kit comprises a lipid standard chosen from the lipids in Tables 4, 7, 10 or 13, one or more control lipidomic markers, an antibody against one of the said lipids, and reagents for performing the method.

BRIEF DESCRIPTION OF THE FIGURES

FIG. 1.

This FIGURE demonstrates the importance of molecular lipid measurements. Two examples are given in this FIGURE to illustrate that two closely related molecular lipids may have a very different or even opposite effect on CVD complications. First quadrangles are used to indicate two Lactosylceramides (LacCer). LacCer (18:1/20:0) is a significant predictor for CVD Death, while closely related LacCer (18:1/16:0) has only limited or no value as a risk predictor. Second example proves that that two lipid species from the same lipid class may have even an opposite effect on CVD events. PC (18:0/20:4) proved to be a protective lipid against CVD death while PC (16:0/16:0) seems to increase CVD complications.

DETAILED DESCRIPTION OF THE INVENTION

Definitions

Coronary vascular disease/cardiovascular disease (CVD) has its general meaning in the art and is used to classify numerous conditions that affect the heart, heart valves, blood, and vasculature of the body, including CAD. In the present invention the terms CVD and CAD may be used interchangeably. Cardiovascular diseases include endothelial dysfunction, coronary artery disease, angina pectoris, myocardial infarction, atherosclerosis, congestive heart failure, hypertension, cerebrovascular disease, stroke, transient ischemic attacks, deep vein thrombosis, peripheral artery disease, cardiomyopathy, arrhythmias, aortic stenosis, and aneurysm. Such diseases frequently involve atherosclerosis. In a preferred embodiment of the invention, the cardiovascular disease is a cardiovascular disease associated with atherosclerosis.

CAD is coronary artery disease, AMI is acute myocardial infarction, ACS is acute coronary syndrome, CAC is coronary artery calcification, RCT is reverse cholesterol transport, LDL is low density lipoprotein, HDL is high density lipoprotein, LDL-C is low density lipoprotein cholesterol, HDL-C is high density lipoprotein cholesterol, ApoA is Apolipoprotein A, ApoB is Apolipoprotein B, ApoC is apolipoprotein C, MS is mass spectrometry, HPLC is high performance liquid chromatography, and UPLC is ultra performance liquid chromatography.

As used herein, "a subject" includes all mammals, including without limitation humans, but also non-human primates, dogs, cats, horses, sheep, goats, cows, rabbits, pigs and rodents.

A "sample" is defined as any biological sample obtained from a subject or a group or population of subjects. For the purposes of the present invention, the biological sample may be whole blood, blood serum, or blood plasma. It may also be a tissue sample. However, a preferred embodiment is wherein the biological sample is plasma or serum. Taking a blood sample of a patient is a part of normal clinical practice. The blood sample can be taken in connection with e.g. measuring the cholesterol levels in the patients. The collected blood sample can be prepared and serum or plasma can be separated with techniques well known to a person skilled in the art. Vena blood samples can be collected from patients using a needle and a BD Vacutainer® Plastic Tubes or Vacutainer® Plus Plastic Tubes (BD Vacutainer® SST™ Tubes contain spray-coated silia and a polymer gel for serum separation). Serum can be separated by centrifugation at 1300 RCF for 10 min at room temperature and stored in small plastic tubes at −80° C.

For the purposes of the present invention, lipids from the Lipidomic analysis were named according to the following nomenclature: CE is cholesteryl ester, Cer is ceramide, DAG is diacylglycerol, PC O is ether-linked PC, GD is disialogangliosides, GlcCer is galactosyl- and glucosylceramides, GM is monosialogangliosides, LacCer is lactosylceramides, LPC is lysophosphatidylcholine, PC is Phosphatidylcholine, PE is Phosphatidylethanolamine, PI is Phosphatidylinositol, SM is Sphingomyelin, SiP is sphingosine-1-phosphate.

The nomenclature X:Y indicates, X number of total carbon atoms in the fatty acid(s) portions of the molecule, and Y the total number of double bonds in the fatty acid portion(s) of the molecule.

The nomenclature A/B indicates, for a molecule of DAG and PC, A and B types of fatty acid moieties attached to the glycerol backbone of the molecule.

The nomenclature (dC/A) indicates, for a molecule of Cer, GlcCer, LacCer and SM, C the type of long-chain base with an amide-linked, A, fatty acid moiety.

The wording "compared to a control sample" as used herein will be understood to include embodiments where control samples are actually analyzed in respect of a lipidomic marker of interest, i.e., in respect of the concentration of one or more of the lipid(s), the lipid-lipid ratios, or the lipid-clinical concentration ratios or combinations thereof as specifically described herein in connection with the various aspects and embodiments of the present invention. It will be appreciated, however, that the above wording also includes embodiments where the corresponding information on said lipidomic marker in said control sample is merely taken from the literature, or has been previously determined, calculated or extrapolated, or is yet to be determined, calculated or extrapolated.

As used herein, the term "antibody" includes monoclonal and polyclonal antibodies, whole antibodies, antibody fragments, and antibody sub-fragments that exhibit specific binding to a said lipid. Thus, suitable "antibodies" can be whole immunoglobulins of any class, e.g., IgG, IgM, IgA, IgD, IgE, chimeric antibodies or hybrid antibodies with dual or multiple antigen or epitope specificities, or fragments, e.g., F(ab')$_2$, Fab', Fab and the like, including hybrid fragments, and additionally includes any immunoglobulin or any natural, synthetic or genetically engineered protein that acts like an antibody by binding to a specific antigen to form a complex. The term "antibody" encompasses antigen-binding fragments of antibodies (e.g., single chain antibodies, Fab fragments, F(ab')$_2$, a Fd fragment, a Fv fragment and dAb fragments) as well as complete antibodies. For example, Fab molecules can be expressed and assembled in a genetically transformed host like *E. coli*. A lambda vector system is available thus to express a population of Fab's with a potential diversity equal to or exceeding that of subject generating the predecessor antibody. See Huse W D, et al., *Science* 1989, 246:1275-81. Such Fab's are included in the definition of "antibody." The ability of a given molecule, including an antibody fragment or sub-fragment, to act like an antibody and specifically bind to a specific antigen can be determined by binding assays known in the art, for example, using the antigen of interest as the binding partner.

Antibodies against lipids in accordance with the present invention may be prepared by methods well known to those skilled in the art. For example, mice may be immunized with a lipid with adjuvant. Splenocytes are harvested as a pool from the mice that were administered 3 immunizations at 2-week intervals with test bleeds performed on alternate weeks for serum antibody titers. Splenocytes are prepared as 3 aliquots that are either used immediately in fusion experiments or stored in liquid nitrogen for use in future fusions.

Fusion experiments are then performed according to the procedure of Stewart & Fuller, *J. Immunol. Methods* 1989, 123:45-53. Supernatants from wells with growing hybrids are screened by enzyme-linked immunosorbent assay (ELISA) for monoclonal antibody (MAb) secretors on 96-well ELISA plates coated with the said lipid. ELISA positive cultures are cloned by limiting dilutions, typically resulting in hybridomas established from single colonies after 2 serial cloning experiments.

EXAMPLES

Example 1

Materials and Methods

This study is a sub-cohort of the LURIC study that is a large scale prospective study on cardiovascular epidemiology. LURIC database contains clinical information over 3000 patients including baseline coronary angiography, clinically used biomarker data and also e.g. CVD mortality data for the follow-up period (3 years). In this biomarker study the inventors compared CAD cases (n=62) that died during the follow-up due to CVD with patients (n=173) having a stable CAD. Subjects with a significant atherosclerosis level in the angiogram but no CVD related death during the follow-up were used as controls, while the case group had similarly a significant atherosclerosis based on the angiography at baseline and in addition they died during the follow-up due to acute cardiovascular events. A statistical analysis was performed separately also for cases (n=48) and controls (n=124) that were not treated with statins. The clinical characteristics are described in Table 1.

TABLE 1

Background characteristics for LURIC patients analyzed with lipidomics

| Variable | Controls (n = 173) | Cases (n = 62) |
|---|---|---|
| Age (average) | 60 | 67 |
| LDL-C (mg/dL) | 122 | 117.5 |
| HDL-C (mg/dL) | 37.2 | 35.3 |
| DM2 patients | 62 (36%) | 36 (58%) |
| Hypertensive patients | 101 (58%) | 39 (63%) |
| Lipid lowering users | 49 (28%) | 14 (23%) |
| Smokers (active or quit less than 3 years before sampling) | 46 (27%) | 8 (13%) |

Definition of Cases: All cases had a significant vessel disease (>=20% stenosis) in coronary angiogram and they all died due to CVD during the follow-up.
Definition of Controls: All controls had a significant vessel disease (>=20% stenosis) in coronary angiogram, but they did not die due to CVD during the follow-up.

Example 2

Analytical Methods
Mass Spectrometry Driven Lipidomics

Direct infusion coupled to tandem mass spectrometry, i.e. shotgun lipidomics, and two liquid chromatography tandem mass spectrometry (LC-MS/MS) approaches, i.e. ceramide and cerebroside lipidomics and ganglioside lipidomics, were used to identify lipid biomarkers for coronary artery disease (CVD) risk by analyzing molecular lipid species in human serum, plasma, and carotid artery plaques. The applied methods were optimized especially for quantification of molecular cholesteryl esters (CE), phosphatidylcholines (PC), lysophosphatidylcholines (LPC) and other lysophospholipids (LPL), ether-linked phosphatidylcholines (PC O) and other ether-linked phospholipids (PL O), phosphatidylserines (PS), phosphatidylethanolamines (PE), phosphatidylglycerols (PG), phosphatidylinositols (PI), phosphatidic acids (PA), diacylglycerols (DAG), ceramides (Cer), glucosylceramides (GlcCer) and lactosylceramides (LacCer).

The following materials were used according to the methods. HPLC or LC-MS grade of chloroform, methanol, water, acetonitrile, formic acid, methanol, isopropanol, ammonium acetate, acetic acid, potassium chloride and butylated hydroxytoluene (BHT) were purchased from Sigma-Aldrich (St. Louis, MO, USA).

HPLC column (Acquity BEH C18, 2.1×50 mm id. 1.7 μm) was purchased from Waters (Milford, MA, USA). HPLC pre-column (Widepore C18 4×2.0 mm) was purchased from Phenomenex (Torrance, CA, USA). All labware used for the extraction were resistant to chloroform. Aerosol resistant filter tips (Molecular BioProducts) and Eppendorf 2 ml safe-lock tubes, 96-well twin.tec PCR plates, and Pierce-it-lite thermo-sealing foils were purchased from VWR International (West Chester, PA, USA). CO-RE Filter Tips and 96-well 2 ml Whatman Uniplates were purchased from Hamilton Robotics (Bonaduz, Switzerland). Synthetic lipid standards were purchased from Avanti Polar Lipids (Alabaster, AL, USA) and from Matreya (Pleasant Gap, PA, USA).

Lipids were extracted in chloroform:methanol according to the following protocols. Samples were spiked with known amounts of non-endogenous synthetic internal standards for data normalization and endogenous lipid quantification. In shotgun lipidomics analysis; LPC 17:0, PC 17:0/17:0, PA 17:0/17:0, PE 17:0/17:0, PG 17:0/17:0, PS 17:0/17:0, DAG 17:0/17:0, D6-CE 18:0, in ceramide and cerebroside lipidomics; Cer d18:1/17:0, D3-LacCer d18:1/16:0, and D3-GlcCer d18:1/16:0, were used as internal standards. Post-extract spiked non-endogenous synthetic external standards were used for quality controlling. Stock solutions of standards were prepared by dissolving appropriately weighed amounts of each standard in chloroform:methanol (2:1, V:V) to achieve a final concentration of 500 μM. An internal standard mixture containing each of the standard stock was created and used in lipid extraction.

Samples and quality control samples for each extraction batch were thawed on ice. The carotid artery plaque samples were weighed on ice by using a cryo-box and homogenized in ice-cold 70% methanol in water. The Mixer Mill 301 Teflon adapters were kept at −20° C. Homogenization was performed at 15-25 Hz for 2-15 minutes with Mixer Mill 301 (Retch GmbH, Germany).

Lipid extraction of human samples was carried out in automated fashion using a Hamilton MICROLAB STAR system (Hamilton Robotics, Switzerland). Well-mixed samples were aliquoted into a 96-well 2 ml Whatman Uniplate containing ice-cold methanol and 0.1% BHT. 5 µl of serum and plasma and 30 µl of carotid artery plaques were used for shotgun- and ceramide and cerebroside lipidomics and 100 µl of serum and plasma and 200 µl of carotid artery plaques was used for ganglioside lipidomics. The samples were mixed thoroughly after each step in the extraction protocol. The extraction proceeded at room temperature by adding an appropriate volume of internal standard mixture and chloroform, and methanol and water in the case of ganglioside lipidomics. In shotgun and ceramide and cerebroside lipidomics, the organic phase separation was facilitated by adding 20 mM acetic acid and centrifuging the plate for 5 min at 500× g. The organic phase was transferred into a new 96-well 2 ml Whatman Uniplate. The remaining water-containing phase was washed by adding appropriate volume of chloroform followed by centrifugation. The two organic phases were pooled and evaporated under $N_2$ until dryness. The lipid extracts were then re-dissolved in chloroform:methanol (1:2, v:v) including the addition of the synthetic external standard. In ganglioside lipidomics, after thorough mixing the supernatant was collected after 30 min centrifugation at 2000×g. The remaining pellet was re-extracted with appropriate volume of water and chloroform:methanol (1:2, v:v) and the supernatant was collected in the same way as above. The pooled supernatant was subjected to solvent partitioning by addition of water and inversion of the sample tubes. The upper phase was collected after 30 min centrifugation at 2000×g. The lower phase was thoroughly re-extracted with potassium chloride and the produced upper phase was collected as mentioned above. The upper phases were pooled and evaporated under $N_2$ until dryness. The lipid extracts were then re-dissolved in chloroform:methanol (1:2, v:v). The extracts were stored in 2 ml safe-lock Eppendorf tubes at −20° C. prior to MS analysis. Required volumes of lipid extracts were aliquoted into an Eppendorf 96-well twin.tec PCR plate and the plate was heat-sealed with aluminum foil to avoid evaporation.

In shotgun lipidomics, lipid extracts were analyzed on a hybrid triple quadrupole/linear ion trap mass spectrometer (QTRAP 5500, AB Sciex) equipped with a robotic nanoflow ion source (NanoMate HD, Advion Biosciences). The instruments were operated in positive and negative ion modes. In positive ion the spray voltage was set to 1.0 to 1.4 kV and in negative ion mode to −1.0 to −1.4 kV. A gas pressure of 0.3-0.8 psi was used and the interface heater was set at 60° C. The collision energy (CE) and declustering potential (DP) was optimized for each lipid class using synthetic standards. The mass spectrometer was operated in unit resolution mode using a scan speed of 200 Da/s. Molecular lipids were analyzed in both positive and negative ion modes using multiple precursor ion scanning (MPIS) and neutral loss scanning (NLS). The used precursor ion and neutral loss scans in positive mode and negative mode are summarized in Table 2.

TABLE 2

Shotgun lipidomics.

| Lipid Class | Characteristic Fragment | PIS or NL $[M + H]^+$ (m/z) |
|---|---|---|
| PC/SM/LPC | Phosphorylcholine | 184.1 |
| DAG | FA 14:1 | 283.25 |
| DAG | FA 14:0 | 285.25 |
| DAG | FA 16:2 | 309.25 |
| DAG | FA 16:1 | 311.25 |
| DAG | FA 16:0 | 313.25 |
| DAG | FA 17:0 | 327.25 |
| DAG | FA 18:3 | 335.25 |
| DAG | FA 18:2 | 337.25 |
| DAG | FA 18:1 | 339.25 |
| DAG | FA 18:0 | 341.25 |
| DAG | FA 20:5 | 359.25 |
| DAG | FA 20:4 | 361.25 |
| DAG | FA 20:3 | 363.25 |
| DAG | FA 20:2 | 365.25 |
| DAG | FA 20:1 | 367.25 |
| CE | Cholestadiene | 369.35 |
| d6-CE | d6-Cholestadiene | 375.35 |
| DAG | FA 22:6 | 385.30 |
| DAG | FA 22:5 | 387.30 |
| DAG | FA 22:4 | 389.30 |
| DAG | FA 22:3 | 391.30 |
| PE/PE-O | phosphorylethanolamine | NL 141.0 |
| PS | phosphorylserine | NL 185.0 |
| PG | phosphorylglycerol + $NH_4$ | NL 189.0 |
| PI | phosphorylinositol + $NH_4$ | NL 277.1 |

| Lipid Class | Characteristic Fragment | PIS or NL $[M - H]^-$ (m/z) |
|---|---|---|
| PA/PG/PS/PI | Glycerophosphate-$H_2O$ | 153.000 |
| PC/LPC | Phosphorylcholine | 168.000 |
| PA/PG/PS/PI/PC/LPC | FA 10:1 | 169.100 |
| PA/PG/PS/PI/PC/LPC | FA 10:0 | 171.100 |
| PA/PG/PS/PI/PC/LPC | FA 11:1 | 183.100 |
| PA/PG/PS/PI/PC/LPC | FA 11:0 | 185.200 |
| PE | dilyso PE-$H_2O$ | 196.000 |
| PA/PG/PS/PI/PC/LPC | FA 12:1 | 197.200 |
| PA/PG/PS/PI/PC/LPC | FA 12:0 | 199.200 |
| PA/PG/PS/PI/PC/LPC | FA 13:1 | 211.200 |
| PA/PG/PS/PI/PC/LPC | FA 13:0 | 213.200 |
| PA/PG/PS/PI/PC/LPC | FA 14:2 | 223.200 |
| PA/PG/PS/PI/PC/LPC | FA 14:1 | 225.200 |
| PA/PG/PS/PI/PC/LPC | FA 14:0 | 227.200 |
| PA/PG/PS/PI/PC/LPC | FA 15:2, O-16:2 | 237.200 |
| PA/PG/PS/PI/PC/LPC | FA 15:1, O-16:1 | 239.200 |
| PI | PI-H2O | 241.000 |
| PA/PG/PS/PI/PC/LPC | FA 15:0 | 241.200 |
| PA/PG/PS/PI/PC/LPC | FA 16:2 | 251.200 |
| PA/PG/PS/PI/PC/LPC | FA 16:1 | 253.200 |
| PA/PG/PS/PI/PC/LPC | FA 16:0 | 255.200 |
| PA/PG/PS/PI/PC/LPC | FA 20:5-$CO_2$ | 257.200 |
| PC/LPC | D3-FA 16:0 | 258.200 |
| PA/PG/PS/PI/PC/LPC | FA 20:4-$CO_2$ | 259.200 |
| PA/PG/PS/PI/PC/LPC | FA 17:2 | 265.200 |
| PA/PG/PS/PI/PC/LPC | O-18:2 | 265.300 |
| PA/PG/PS/PI/PC/LPC | FA 17:1 | 267.200 |
| PA/PG/PS/PI/PC/LPC | FA 17:0 | 269.300 |
| PA/PG/PS/PI/PC/LPC | FA 18:3 | 277.200 |
| PA/PG/PS/PI/PC/LPC | FA 18:2 | 279.200 |
| PA/PG/PS/PI/PC/LPC | FA 18:1 | 281.300 |
| PA/PG/PS/PI/PC/LPC | FA 18:0 | 283.300 |
| PA/PG/PS/PI/PC/LPC | FA 22:5-$CO_2$ | 285.300 |
| PA/PG/PS/PI/PC/LPC | FA 22:4-$CO_2$ | 287.300 |
| PA/PG/PS/PI/PC/LPC | FA 19:2 | 293.300 |
| PA/PG/PS/PI/PC/LPC | FA 19:1 | 295.300 |
| PA/PG/PS/PI/PC/LPC | FA 19:0 | 297.300 |
| PA/PG/PS/PI/PC/LPC | FA 20:5 | 301.200 |
| PA/PG/PS/PI/PC/LPC | FA 20:4 | 303.200 |
| PA/PG/PS/PI/PC/LPC | FA 20:3 | 305.200 |
| PA/PG/PS/PI/PC/LPC | FA 20:2 | 307.300 |
| PA/PG/PS/PI/PC/LPC | FA 20:1 | 309.300 |
| PA/PG/PS/PI/PC/LPC | FA 20:0 | 311.300 |
| PA/PG/PS/PI/PC/LPC | FA 22:6 | 327.200 |
| PA/PG/PS/PI/PC/LPC | FA 22:5 | 329.200 |
| PA/PG/PS/PI/PC/LPC | FA 22:4 | 331.300 |
| PA/PG/PS/PI/PC/LPC | FA 22:3 | 333.300 |
| PA/PG/PS/PI/PC/LPC | FA 22:2 | 335.300 |
| PA/PG/PS/PI/PC/LPC | FA 22:1 | 337.300 |
| PA/PG/PS/PI/PC/LPC | FA 22:0 | 339.300 |
| SGalCer | $HSO_4$ | 96.9 |
| PS | Serine-$H_2O$ | NL 87.1 |

In ceramide and cerebroside lipidomics, the high performance liquid chromatography (HPLC) analyses were conducted in the following way. Chromatographic apparatus consisted of a CTC HTC PAL autosampler (CTC Analytics AG, Switzerland), a Rheos Allegro UHPLC pump (Flux Instruments AG, Switzerland), an external column heater set to 60° C. for ceramide and cerebroside lipidomics and 45° C. for ganglioside lipidomics, and the Acquity BEH C18 column with an in-line pre-column. The extracted samples, 10 µl of each, were injected into the pre-column followed by the analytical column and delivered to the mass spectrometer at a flow rate of 500 µl/min. In ceramide and cerebroside lipidomics, A gradient was used for lipid analyte separation with solvent A comprising 10 mM ammonium acetate in HPLC grade water containing 0.1% formic acid and solvent B of 10 mM ammonium acetate in acetonitrile:isopropanol (4:3, V:V) containing 0.1% formic acid. The gradient was constructed in the following way: 0 min—65% B; 2 min—65% B; 2.5 min—75% B; 17.5 min—100% B; 22.5 min—100% B; 22.6 min—65% B; 25 min—65% B.

The lipid extracts were analyzed by HPLC-MS/MS. The MS analysis was performed on a hybrid triple quadrupole/linear ion trap mass spectrometer equipped with the Turbo V™ Ion Source (4000 QTRAP, AB Sciex). The instrument was operating in positive and negative ion modes. The ion source voltage was set to 5500V for ceramide and cerebroside lipidomics and to −4500V for ganglioside lipidomics, and source temperature at 400° C. The collision energy (CE) and declustering potential (DP) was optimized for each lipid class using synthetic standards. A 20 sec dwell time was applied for each scan. Multiple reaction monitoring (MRM) scan mode was used. MRM transitions for each lipid species are summarized in table 3.

TABLE 3

Ceramide and cerebroside lipidomics.

| Lipid | [M + H]⁺ (m/z) | Product [M + H]⁺ (m/z) |
|---|---|---|
| Cer(d18:0/16:0) | 540.5 | 266.25 |
| Cer(d18:0/18:0) | 568.6 | 266.25 |
| Cer(d18:0/20:0) | 596.6 | 266.25 |
| Cer(d18:0/22:0) | 624.6 | 266.25 |
| Cer(d18:0/24:0) | 652.7 | 266.25 |
| Cer(d18:0/24:1) | 650.6 | 266.25 |
| Cer(d18:0/26:0) | 680.7 | 266.25 |
| Cer(d18:0/26:1) | 678.7 | 266.25 |
| Cer(d18:1/16:0) | 538.5 | 264.25 |
| Cer(d18:1/18:0) | 566.5 | 264.25 |
| Cer(d18:1/20:0) | 594.6 | 264.25 |
| Cer(d18:1/22:0) | 622.6 | 264.25 |
| Cer(d18:1/24:0) | 650.6 | 264.25 |
| Cer(d18:1/24:1) | 648.6 | 264.25 |
| Cer(d18:1/26:0) | 678.7 | 264.25 |
| Cer(d18:1/26:1) | 676.7 | 264.25 |
| GlcCer(d18:0/16:0) | 702.6 | 266.25 |
| GlcCer(d18:0/18:0) | 730.6 | 266.25 |
| GlcCer(d18:0/20:0) | 758.6 | 266.25 |
| GlcCer(d18:0/22:0) | 786.7 | 266.25 |
| GlcCer(d18:0/24:0) | 814.7 | 266.25 |
| GlcCer(d18:0/24:1) | 812.7 | 266.25 |
| GlcCer(d18:0/26:0) | 842.7 | 266.25 |
| GlcCer(d18:0/26:1) | 840.7 | 266.25 |
| GlcCer(d18:1/16:0) | 700.6 | 264.25 |
| GlcCer(d18:1/18:0) | 728.6 | 264.25 |
| GlcCer(d18:1/20:0) | 756.6 | 264.25 |
| GlcCer(d18:1/22:0) | 784.7 | 264.25 |
| GlcCer(d18:1/24:0) | 812.7 | 264.25 |
| GlcCer(d18:1/24:1) | 810.7 | 264.25 |
| GlcCer(d18:1/26:0) | 840.7 | 264.25 |
| GlcCer(d18:1/26:1) | 838.7 | 264.25 |
| LacCer(d18:1/16:0) | 862.6 | 264.25 |
| LacCer(d18:1/18:0) | 890.7 | 264.25 |
| LacCer(d18:1/20:0) | 918.7 | 264.25 |
| LacCer(d18:1/22:0) | 946.7 | 264.25 |
| LacCer(d18:1/24:0) | 974.7 | 264.25 |
| LacCer(d18:1/24:1) | 972.7 | 264.25 |
| LacCer(d18:1/26:0) | 1002.8 | 264.25 |
| LacCer(d18:1/26:1) | 1000.8 | 264.25 |
| LacCer(d18:0/16:0) | 864.6 | 266.25 |
| LacCer(d18:0/18:0) | 892.7 | 266.25 |
| LacCer(d18:0/20:0) | 920.7 | 266.25 |
| LacCer(d18:0/22:0) | 948.7 | 266.25 |
| LacCer(d18:0/24:0) | 976.7 | 266.25 |
| LacCer(d18:0/24:1) | 974.7 | 266.25 |
| LacCer(d18:0/26:0) | 1004.8 | 266.25 |
| LacCer(d18:0/26:1) | 1002.8 | 266.25 |
| Cer(d18:1/16:0)-OH | 554.5 | 264.25 |
| Cer(d18:1/18:0)-OH | 582.5 | 264.25 |
| Cer(d18:1/20:0)-OH | 610.6 | 264.25 |
| Cer(d18:1/22:0)-OH | 638.6 | 264.25 |
| Cer(d18:1/24:0)-OH | 666.6 | 264.25 |
| Cer(d18:1/24:1)-OH | 664.6 | 264.25 |
| Cer(d18:1/26:0)-OH | 694.7 | 264.25 |
| Cer(d18:1/26:1)-OH | 692.7 | 264.25 |
| IS D3-LacCer d18:1/16:0 | 865.6 | 264.25 |
| IS D3-GluCer d18:1/16:0 | 703.7 | 264.25 |
| IS Cer d18:1/17:0 | 552.5 | 264.25 |
| ES Cer d17:1/18:0 | 552.5 | 250.25 |

The data processing was done in the following way. Initially the retention time (in LC mode) and identification of each peak was done using endogenous standards and by Information Dependent Acquisition (IDA) experiments where applicable. The raw data were processed according to peak detected and retention time (in LC mode) in automated fashion. A stringent cutoff was applied for separating background noise from actual lipid peaks. Each sample was controlled and only accepted when fulfilling the stringent acceptance criteria. Peak area counts (cps) of detected peaks were converted into a list of corresponding lipid names. Lipids were normalized to their respective internal standard and sample volume or tissue weight to retrieve their concentrations.

Several quality controls were used in the lipidomic analyses. A calibration line using synthetic or isolated standards was obtained prior to sample analysis. Synthetic standards were chosen based on application and had similar properties to the endogenous lipids or analyte(s) of interest. The calibration line consisted of a minimum of five standards points covering the expected quantification range. A sample extracted without standard and standards extracted with no matrix, were included with the calibration line.

The calibration line was used to determine the dynamic quantification range for each lipid class monitored, e.g., the linear quantification limits. As the internal standards used behave in the same way as endogenous lipids they were used for quantifying endogenous lipid species. The calibration lines were based on the same internal standards that were used for quantification of the endogenous lipids.

In each sample extracted for lipids, the ratio of synthetic internal standards (IS) to corresponding post-extract spiked external standard (ES) was determined. The peak area (cps) ratio of internal to external standard (IS/ES) was used for calculating the Coefficient of Variation (CV) across all samples. The IS/ES ratio enabled the calculation of lipid extraction recovery.

Instrument control (IC) was included at the start, middle and end of each run. IC sample analyzed was an extracted reference plasma sample and a set of standards to monitor the instrument's performance, i.e., the intra- and inter-assay variation.

For each platform, a stringent cutoff was applied for separating background noise from actual lipid peaks. Each sample was controlled and only accepted when fulfilling the stringent acceptance criteria. Masses and counts of detected peaks were converted into a list of corresponding lipid names. Lipids were normalized to their respective internal standard and sample volume to retrieve their concentrations.

Statistical Analyses

Percentage changes in lipid concentrations between control and case groups were calculated as follows:

100*(AVG[C] in case group−AVG[C] in control group)/AVG[C] in control group

Statistical significance was assigned based on standard t-test p-values.

In addition, ROC curves were used for finding lipid molecules and concentration cutoffs that separate the best cases from controls. Selectivity is calculated as a number of correctly identified cases divided by the total number of cases. Specificity is calculated as a number of correctly identified controls divided by the total number of controls. Selectivity and specificity was calculated for each lipid concentration, lipid to lipid ratio and ratio of lipid to clinical concentrations.

Example 3

Ethics

The LURIC study was approved by the ethics review committee at the "Landesirztekammer Rheinland-Pfalz" (Mainz, Germany). Written informed consent was obtained from each of the participants.

Results

In this LURIC study sub-cohort, the traditional biomarkers including LDL-cholesterol and HDL-cholesterol concentrations were practically identical in both groups and therefore were not predictive of CVD-related mortality in this study.

Multiple lipidomic markers appeared as significant predictors of CVD death (Tables 4-13). A total of 151 molecular lipids were quantified. The significant predictors were selected based on the top fifty candidates from each category, when available. The biomarker candidates based on molecular lipid concentrations are presented in Tables 4, 7, 10 and 13. The candidates were selected according to the following criteria: t-test p-value≤0.05 or sensitivity≥60% and specificity≥60%. From traditional clinical chemistry only apolipoprotein A1 and total cholesterol reached statistical significance with p-value lower than 0.05, but % change was less than 10% between controls and cases, other clinical values did not show any statistical significance. The predictive value of new lipidomic biomarkers was increased when their levels were expressed as distinct lipid-lipid ratios or lipid-clinical ratios (e.g. LDL-C or HDL-C). The top biomarker candidates are presented in Table 13. Top candidates from each category, when available, were selected based on the following selection criteria: t-test p-value≤0.05 and sensitivity≥60% and specificity≥60%.

Importance of Detailed Molecular Lipid Analyses

Recent evolvement of mass spectrometry driven lipid analysis approaches has made it possible to resolve complex lipidomes to their molecular lipid species level at high-throughput and quality required for analyses of clinical cohorts. As a result of the high sensitivity and selectivity of the methods, a lipidome-wide analysis of minute sample amounts has become feasible. Present technologies are capable of identifying lipids with different sum compositions, i.e. phosphatidylcholine (PC) 34:1, but more important is the identification of molecular lipid species, e.g. PC 16:0/18:1. In the latter analysis, information of the type of fatty acids and their positions attached to the glycerol backbone making up the particular PC molecule is retrieved.

The seminal work of Shinzawa-Itoh and colleagues showed by highly sophisticated experiments that the oxygen transfer mechanism in cytochrome c oxidase requires a specific phosphatidylglycerol molecular lipid with palmitate and vaccenate at the sn-1 and sn-2 positions respectively on the glycerol backbone (Shinzawa-Itoh K, Aoyama H, Muramoto K et al: *Structures and physiological roles of 13 integral lipids of bovine heart cytochrome c oxidase. EMBO J* 2007, 26:1713-1725). In line with other studies, this undoubtedly indicates that the lipid structure is an essential determinant of the biological effect. Therefore, molecular lipidomics is an essential for biomarker discovery. FIG. 1 illustrates the importance of molecular lipid data by comparing the biomarker value of two PC and LacCer molecules in predicting CVD mortality in the LURIC cohort. The data reveals that while LacCer(d18:1/20:0) is a significant CVD predictor, LacCer (d18:1/18:16:0) has low biomarker potential. In addition, two PC molecules PC (18:0/20:4) and PC (18:0/16:0) have even opposite effects on CVD complications. Thus, it is always necessary to identify and quantify all lipid species for lipid classes of interest including but not limited to cholesterol esters, different phopsholipid classes, ceramides, cerebrosides (lactosylceramides, glycosylceramides), and gangliosides.

TABLE 4

Significant lipids in LURIC study sorted by p-value. Lipid names, p-values and % change for negative correlation are presented. Table 4a shows significant lipids from all study subjects. The significant lipids from subjects not undergoing statin treatment are listed in table 4b.

| Lipid name | p-value | Percentage change |
| --- | --- | --- |
| 4a) Significant lipids in LURIC study sorted by p-value from all study subjects. | | |
| Positive correlation | | |
| LacCer(d18:1/20:0) | 0.00008 | 29.52421 |
| LacCer(d18:1/22:0) | 0.00046 | 22.75541 |
| LacCer(d18:1/18:0) | 0.00094 | 26.78692 |
| Cer(d18:1/18:0) | 0.00177 | 23.30373 |
| Cer(d18:1/20:0) | 0.00302 | 17.32385 |
| LacCer(d18:1/24:1) | 0.00361 | 24.72456 |
| PS O-18:2/16:0-alkenyl | 0.00571 | 49.89286 |
| PS O-16:0/18:2-alkenyl | 0.00670 | 49.99084 |
| PS O-16:1/18:2-alkyl | 0.00670 | 49.99084 |
| Cer(d18:1/24:1) | 0.01142 | 14.88898 |
| Total LacCer | 0.01669 | 13.83938 |
| PS O-18:0/18:2-alkenyl (PS O-18:1/18:2-alkyl) | 0.02899 | 40.93773 |
| LacCer(d18:1/24:0) | 0.04425 | 15.80958 |
| PC O-32:0 (KDdiA-PC) | 0.04546 | 17.40815 |
| GlcCer(d18:1/18:0) | 0.04913 | 12.83156 |
| Negative correlation | | |

TABLE 4-continued

Significant lipids in LURIC study sorted by p-value. Lipid names, p-values and % change for negative correlation are presented. Table 4a shows significant lipids from all study subjects. The significant lipids from subjects not undergoing statin treatment are listed in table 4b.

| Lipid name | p-value | Percentage change |
|---|---|---|
| Total PC | 0.00011 | −16.07367 |
| PC 16:0/20:4 | 0.00077 | −18.06547 |
| Total LPC | 0.00126 | −17.02070 |
| CE 14:0 | 0.00181 | −22.73309 |
| PC 16:0/20:3 | 0.00191 | −18.78110 |
| Cer(d18:0/24:0) | 0.00254 | −27.27562 |
| PC 18:0/20:4 | 0.00303 | −16.02110 |
| CE 20:3 | 0.00312 | −19.02446 |
| CE 17:1 | 0.00694 | −16.90145 |
| PC 18:0/20:3 | 0.00726 | −17.20664 |
| PC 18:0/18:1 | 0.00765 | −18.18002 |
| Cer(d18:0/22:0) | 0.01158 | −22.37263 |
| PC 16:0/22:6 | 0.01180 | −16.65050 |
| LPC 18:1 | 0.01457 | −14.45827 |
| SM (d18:1/23:0) (d18: 1/22:1-OH) | 0.01920 | −14.02360 |
| CE 16:0 | 0.02427 | −10.63490 |
| Total CE | 0.02745 | −11.83333 |
| SM (d18:1/24:0) (d18:1/23:1-OH) | 0.02784 | −13.83715 |
| PC 18:1/18:2 | 0.03666 | −10.83371 |

4b) Significant lipids in LURIC study sorted by p-value from subjects not undergoing statin treatment.

| Positive correlation | | |
|---|---|---|
| Cer(d18:1/20:0) | 0.00004 | 28.00357 |
| Cer(d18:1/18:0) | 0.00009 | 34.32550 |
| LacCer(d18:1/20:0) | 0.00010 | 32.91154 |
| Cer(d18:1/24:1) | 0.00039 | 23.37606 |
| LacCer(d18:1/22:0) | 0.00048 | 25.61851 |
| LacCer(d18:1/18:0) | 0.00144 | 29.19850 |
| LacCer(d18:1/24:1) | 0.00199 | 29.83279 |
| PS O-18:2/16:0-alkenyl | 0.00432 | 33.81177 |
| Cer(d18:1/22:0) | 0.00473 | 18.32126 |
| PS O-16:0/18:2-alkenyl | 0.00590 | 32.17190 |
| PS O-16:1/18:2-alkyl | 0.00590 | 32.17190 |
| Total DAG | 0.00794 | 31.67365 |
| Cer(d18:1/16:0) | 0.00952 | 16.71359 |
| Total Cer | 0.00932 | 15.44601 |
| Total LacCer | 0.01105 | 16.00541 |
| LacCer(d18:1/24:0) | 0.01989 | 19.85622 |
| GlcCer(d18:1/20:0) | 0.02288 | 17.74772 |
| PC O-32:0 (KDdiA-PC) | 0.02467 | 22.23265 |
| GlcCer(d18:1/18:0) | 0.02584 | 16.12961 |
| GlcCer(d18:1/24:1) | 0.03290 | 18.89331 |
| GlcCer(d18:1/26:1) | 0.04702 | 17.52675 |
| Cer(d18:1/26:1) | 0.04802 | 13.59618 |
| Negative correlation | | |
| Total PC | 0.00921 | −12.44220 |
| CE 14:0 | 0.01090 | −21.01258 |
| CE 20:3 | 0.02157 | −16.03606 |
| CE 17:1 | 0.02204 | −15.93952 |
| PC 16:0/20:4 | 0.02256 | −14.96966 |
| PC 18:0/20:4 | 0.03376 | −13.60917 |
| Cer(d18:0/24:0) | 0.03376 | −21.87004 |
| Total LPC | 0.03443 | −12.91576 |
| PC 16:0/20:3 | 0.04337 | −13.43056 |

TABLE 5

Table of significant lipid to lipid ratios in LURIC study sorted by p-value. Lipid names, p-values, % change both for positive and negative correlation are presented. Table 5a shows significant lipids from all study subjects. The significant lipids from subjects not undergoing statin treatment are listed in table 5b.

| Lipid name/lipid name | p-value | Percentage change |
|---|---|---|
| 5a) Significant lipid to lipid ratios in LURIC study sorted by p-value from all study subjects. | | |
| Positive correlation | | |
| GlcCer(d18:1/26:0)/Total CE | 0.0000000 | 12.8050228 |
| GlcCer(d18:1/26:1)/Total CE | 0.0000000 | 29.5576923 |
| PS O-16:0/18:2-alkenyl/Total PS O | 0.0000000 | 26.0723978 |
| PS O-16:1/18:2-alkyl/Total PS O | 0.0000000 | 26.0723978 |
| PS O-18:2/16:0-alkenyl/Total PS O | 0.0000000 | 28.7826715 |
| Cer(d18:1/24:1)/Total PC | 0.0000000 | 38.6612692 |
| PC 16:0/16:0/Total PC | 0.0000000 | 26.1328496 |
| LacCer(d18:1/20:0)/Total PC | 0.0000000 | 55.3076855 |
| Cer(d18:1/24:1)/PC 16:0/20:4 | 0.0000000 | 52.6701270 |
| Cer(d18:1/20:0)/Total PC | 0.0000000 | 40.0940286 |
| LacCer(d18:1/18:0)/Total PC | 0.0000000 | 53.5855166 |
| Cer(d18:1/18:0)/Total PC | 0.0000000 | 48.2586905 |
| Cer(d18:1/18:0)/PC 16:0/20:4 | 0.0000000 | 65.7060860 |
| Cer(d18:1/24:1)/PC 16:0/18:1 | 0.0000000 | 34.2415459 |
| PS O-18:0/18:2-alkenyl (PS O-18:1/18:2-alkyl)/Total PS O | 0.0000000 | 18.7146206 |
| Total LacCer/Total PC | 0.0000001 | 40.0389043 |
| Cer(d18:1/24:1)/PC 16:0/20:3 | 0.0000001 | 39.6033049 |
| Cer(d18:1/22:0)/Total PC | 0.0000001 | 31.3604924 |
| Cer(d18:1/20:0)/PC 16:0/20:4 | 0.0000001 | 55.6619154 |
| LacCer(d18:1/22:0)/Total PC | 0.0000001 | 48.7385500 |
| LacCer(d18:1/20:0)/PC 16:0/20:3 | 0.0000001 | 57.2475183 |
| Cer(d18:1/18:0)/PC 16:0/20:3 | 0.0000002 | 53.4975004 |
| LacCer(d18:1/20:0)/PC 18:0/20:3 | 0.0000002 | 56.3125345 |
| LacCer(d18:1/18:0)/PC 18:0/20:3 | 0.0000002 | 58.4642532 |
| Cer(d18:1/22:0)/PC 16:0/20:4 | 0.0000002 | 42.5755107 |
| LacCer(d18:1/20:0)/PC 18:0/18:1 | 0.0000004 | 50.6042672 |
| Cer(d18:1/24:1)/LPC 18:1 | 0.0000004 | 37.9852355 |
| LacCer(d18:1/20:0)/PC 16:0/18:1 | 0.0000004 | 46.3528827 |
| LacCer(d18:1/20:0)/PC 18:1/18:1 | 0.0000004 | 49.6378601 |
| Cer(d18:1/18:0)/PC 16:0/18:1 | 0.0000004 | 42.1348344 |
| Cer(d18:1/18:0)/PC 18:0/20:4 | 0.0000005 | 55.4207048 |
| Cer(d18:1/24:1)/PC 18:0/20:4 | 0.0000005 | 40.7129933 |
| Cer(d18:1/20:0)/PC 16:0/20:3 | 0.0000005 | 44.8451813 |
| LacCer(d18:1/18:0)/PC 18:0/18:1 | 0.0000006 | 50.0860210 |
| Cer(d18:1/20:0)/PC 16:0/18:1 | 0.0000006 | 35.2897482 |
| LacCer(d18:1/20:0)/PC 18:1/18:2 | 0.0000007 | 47.4807020 |
| Cer(d18:1/24:1)/Total LPC | 0.0000007 | 37.5873387 |
| Total Cer/Total PC | 0.0000007 | 28.8638001 |
| Cer(d18:1/20:0)/PC 18:0/20:4 | 0.0000007 | 46.2204972 |
| LacCer(d18:1/18:0)/PC 18:1/18:1 | 0.0000007 | 47.3110220 |
| LacCer(d18:1/18:0)/PC 16:0/20:3 | 0.0000007 | 55.5925567 |
| LacCer(d18:1/24:1)/Total PC | 0.0000008 | 56.5726916 |
| Cer(d18:1/24:1)/PC 18:0/18:1 | 0.0000008 | 38.3563305 |
| Cer(d18:1/24:1)/PC 18:0/20:3 | 0.0000013 | 39.6802706 |
| LacCer(d18:1/22:0)/PC 16:0/20:4 | 0.0000013 | 57.8428560 |
| LacCer(d18:1/18:0)/PC 16:0/18:1 | 0.0000014 | 45.2070855 |
| LacCer(d18:1/22:0)/PC 18:0/20:3 | 0.0000014 | 50.7183795 |
| Cer(d18:1/20:0)/PC 18:1/18:1 | 0.0000016 | 40.1833717 |
| LacCer(d18:1/18:0)/PC 18:1/18:2 | 0.0000017 | 46.5169450 |

TABLE 5-continued

Table of significant lipid to lipid ratios in LURIC study sorted by p-value. Lipid names, p-values, % change both for positive and negative correlation are presented. Table 5a shows significant lipids from all study subjects. The significant lipids from subjects not undergoing statin treatment are listed in table 5b.

| Lipid name/lipid name | p-value | Percentage change |
|---|---|---|
| Cer(d18:1/22:0)/PC 16:0/20:3 | 0.0000018 | 33.7513783 |
| Negative correlation | | |
| Cer(d18:0/22:0)/Total CE | 0.0000000 | −11.7767698 |
| Cer(d18:0/24:0)/Total CE | 0.0000000 | −18.9531828 |
| Cer(d18:0/24:1)/Total CE | 0.0000000 | −1.2444181 |
| CE 18:3/Cer(d18:1/24:1) | 0.0000000 | −35.9591235 |
| Cer(d18:0/24:0)/Cer(d18:1/24:1) | 0.0000004 | −36.1288066 |
| CE 18:3/Total Cer | 0.0000021 | −30.3105704 |
| CE 18:3/PC 16:0/16:0 | 0.0000028 | −30.4716021 |
| CE 18:3/LacCer(d18:1/20:0) | 0.0000028 | −44.3063424 |
| CE 20:3/Cer(d18:1/24:1) | 0.0000034 | −28.1216690 |
| CE 18:3/PS O-16:0/18:2-alkenyl | 0.0000036 | −38.5094276 |
| CE 18:3/PS O-16:1/18:2-alkyl | 0.0000036 | −38.5094276 |
| CE 18:3/Total LacCer | 0.0000037 | −34.1308012 |
| CE 18:3/Cer(d18:1/20:0) | 0.0000037 | −33.6203392 |
| LPC 18:2/LacCer(d18:1/20:0) | 0.0000040 | −41.6604394 |
| Cer(d18:0/24:0)/Total Cer | 0.0000049 | −31.1431758 |
| Cer(d18:0/24:0)/Cer(d18: 1/18:0) | 0.0000052 | −40.2960344 |
| Cer(d18:0/24:0)/PS O-16:0/18:2-alkenyl | 0.0000059 | −40.8329837 |
| Cer(d18:0/24:0)/PS O-16:1/18:2-alkyl | 0.0000059 | −40.8329837 |
| Cer(d18:0/22:0)/Cer(d18:1/24:1) | 0.0000064 | −32.1886967 |
| Cer(d18:0/24:0)/LacCer(d18:1/24:0) | 0.0000067 | −37.0287234 |
| Cer(d18:0/22:0)/Cer(d18:1/18:0) | 0.0000071 | −36.5400374 |
| CE 14:0/Cer(d18:1/24:1) | 0.0000076 | −29.9054883 |
| CE 18:3/Cer(d18:1/16:0) | 0.0000079 | −32.5598715 |
| CE 18:3/Cer(d18:1/18:0) | 0.0000082 | −38.1543108 |
| Cer(d18:0/24:0)/Cer(d18:1/20:0) | 0.0000087 | −35.4631184 |
| CE 18:3/GlcCer(d18:1/20:0) | 0.0000087 | −36.4665498 |
| CE 18:3/Cer(d18:1/22:0) | 0.0000101 | −30.6595286 |
| Cer(d18:0/24:0)/Cer(d18:1/22:0) | 0.0000105 | −32.4086711 |
| Cer(d18:0/22:0)/PS O-16:0/18:2-alkenyl | 0.0000114 | −37.4226868 |
| Cer(d18:0/22:0)/PS O-16:1/18:2-alkyl | 0.0000114 | −37.4226868 |
| CE 18:3/PC O-34:1 | 0.0000122 | −33.4941413 |
| CE 18:3/Total CE | 0.0000151 | −20.2882080 |
| PC 16:0/20:3/PS O-16:0/18:2-alkenyl | 0.0000154 | −29.5280580 |
| PC 16:0/20:3/PS O-16:1/18:2-alkyl | 0.0000154 | −29.5280580 |
| PC 18:1/18:2/PS O-16:0/18:2-alkenyl | 0.0000155 | −23.7129392 |
| PC 18:1/18:2/PS O-16:1/18:2-alkyl | 0.0000155 | −23.7129392 |
| Cer(d18:0/22:0)/Cer(d18:1/20:0) | 0.0000165 | −31.5266149 |
| CE 18:3/LacCer(d18:1/22:0) | 0.0000174 | −37.1525849 |
| LPC 18:2/PS O-16:0/18:2-alkenyl | 0.0000175 | −30.3450779 |
| LPC 18:2/PS O-16:1/18:2-alkyl | 0.0000175 | −30.3450779 |
| CE 17:1/Cer(d18:1/24:1) | 0.0000186 | −24.8594478 |
| CE 16:0/Cer(d18:1/24:1) | 0.0000188 | −19.2509369 |
| CE 18:3/GlcCer(d18:1/18:0) | 0.0000221 | −35.5601491 |
| CE 18:3/LacCer(d18:1/18:0) | 0.0000326 | −37.4416706 |
| CE 18:3/PS O-16:0/18:1-alkenyl (PS O-16:1/18:1-alkyl) | 0.0000326 | −34.1672013 |
| CE 18:3/Cer(d18:1/24:0) | 0.0000331 | −27.4645341 |
| Cer(d18:0/22:0)/Cer(d18:1/22:0) | 0.0000377 | −28.0899033 |
| LPC 16:0/LacCer(d18:1/20:0) | 0.0000391 | −35.6188222 |
| Cer(d18:0/24:0)/Cer(d18:1/16:0) | 0.0000446 | −34.4695918 |
| Total LPC/Total LacCer | 0.0000469 | −26.0881987 |
| 5b) Significant lipid to lipid ratios in LURIC study sorted by p-value from subjects not undergoing statin treatment | | |
| Positive correlation | | |
| GlcCer(d18:1/26:0)/Total CE | 0.000000 | 13.329316 |
| GlcCer(d18:1/26:1)/Total CE | 0.000000 | 35.356592 |
| PS O-16:0/18:2-alkenyl/Total PS O | 0.000000 | 26.426208 |
| PS O-16:1/18:2-alkyl/Total PS O | 0.000000 | 26.426208 |
| PS O-18:2/16:0-alkenyl/Total PS O | 0.000000 | 29.590682 |
| Cer(d18:1/24:1)/Total PC | 0.000000 | 43.040800 |
| Cer(d18:1/24:1)/PC 16:0/20:4 | 0.000000 | 59.876132 |
| Cer(d18:1/24:1)/PC 18:0/20:4 | 0.000000 | 46.504629 |
| Cer(d18:1/20:0)/Total PC | 0.000000 | 46.216544 |
| PC 16:0/16:0/Total PC | 0.000000 | 28.139641 |
| Total DAG/Total LPC | 0.000000 | 57.426180 |
| Cer(d18:1/18:0)/PC 16:0/20:4 | 0.000000 | 73.073704 |
| Cer(d18:1/18:0)/Total PC | 0.000000 | 53.769121 |
| Cer(d18:1/22:0)/Total PC | 0.000000 | 34.704834 |
| Cer(d18:1/22:0)/PC 16:0/20:4 | 0.000000 | 47.860118 |
| Cer(d18:1/20:0)/PC 16:0/20:4 | 0.000000 | 64.045788 |
| LacCer(d18:1/20:0)/Total PC | 0.000000 | 55.686130 |
| Cer(d18:1/18:0)/PC 18:0/20:4 | 0.000000 | 61.943925 |
| Cer(d18:1/20:0)/PC 18:0/20:4 | 0.000000 | 53.941480 |
| Cer(d18:1/24:1)/PC 16:0/18:1 | 0.000000 | 35.646899 |
| Cer(d18:1/24:1)/PC 16:0/20:3 | 0.000000 | 44.382440 |
| Cer(d18:1/18:0)/PC 16:0/20:3 | 0.000001 | 61.224227 |
| Cer(d18:1/20:0)/PC 16:0/20:3 | 0.000001 | 52.891307 |
| Cer(d18:1/24:1)/PC 18:0/18:1 | 0.000001 | 42.115354 |
| Cer(d18:1/22:0)/PC 18:0/20:4 | 0.000001 | 36.949978 |
| Cer(d18:1/20:0)/PC 18:0/18:1 | 0.000004 | 47.396000 |
| SM (d18:1/17:0) (d18:1/16:1-OH)/Total PC O | 0.000004 | 39.660537 |
| PC O-32:0 (KDdiA-PC)/Total PC O | 0.000005 | 46.418572 |
| Cer(d18:1/20:0)/PC 16:0/18:1 | 0.000005 | 37.704904 |
| Cer(d18:1/24:1)/LPC 18:1 | 0.000005 | 40.092181 |
| Cer(d18:1/24:1)/PC 18:1/18:1 | 0.000005 | 38.720001 |
| Cer(d18:1/18:0)/PC 16:0/18:1 | 0.000006 | 44.307054 |
| LacCer(d18:1/18:0)/Total PC | 0.000006 | 50.539560 |
| Cer(d18:1/20:0)/PC 18:1/18:1 | 0.000006 | 44.664936 |
| Cer(d18:1/18:0)/PC 18:0/18:1 | 0.000006 | 54.563687 |
| LacCer(d18:1/20:0)/PC 18:0/20:4 | 0.000007 | 66.072520 |
| Cer(d18:1/24:1)/PC 18:0/20:3 | 0.000007 | 44.320399 |
| LacCer(d18:1/20:0)/PC 16:0/20:3 | 0.000008 | 56.972652 |
| Cer(d18:1/22:0)/PC 16:0/20:3 | 0.000008 | 37.291136 |
| PC 16:0/16:0/PC 16:0/20:4 | 0.000009 | 42.512740 |
| PS O-16:0/18:2-alkenyl/Total PC | 0.000009 | 53.059092 |
| PS O-16:1/18:2-alkyl/Total PC | 0.000009 | 53.059092 |
| LacCer(d18:1/20:0)/PC 18:0/20:3 | 0.000009 | 55.403274 |
| Total Cer/Total PC | 0.000011 | 29.949121 |
| Total LacCer/Total PC | 0.000012 | 37.815865 |
| Total DAG/Total PC | 0.000012 | 57.897424 |
| Cer(d18:1/18:0)/PC 18:1/18:1 | 0.000012 | 49.427440 |
| LacCer(d18:1/20:0)/PC 18:1/18:2 | 0.000013 | 48.432788 |
| Total DAG/Total PC O | 0.000014 | 52.258466 |
| Cer(d18:1/24:1)/Total LPC | 0.000014 | 38.684740 |
| Negative correlation | | |
| Cer(d18:0/22:0)/Total CE | 0.000000 | −6.628640 |
| Cer(d18:0/24:0)/Total CE | 0.000000 | −13.307278 |
| DAG 16:0/18:1/Total DAG | 0.000000 | −17.305276 |
| CE 18:3/Cer(d18:1/24:1) | 0.000000 | −37.975733 |
| CE 16:0/Cer(d18:1/24:1) | 0.000001 | −23.257135 |
| Cer(d18:0/24:0)/Cer(d18:1/24:1) | 0.000003 | −36.760563 |
| CE 20:4/Cer(d18:1/24:1) | 0.000004 | −28.636879 |
| CE 20:3/Cer(d18:1/24:1) | 0.000007 | −30.787067 |
| CE 14:0/Cer(d18:1/24:1) | 0.000008 | −32.409429 |
| Cer(d18:0/22:0)/Cer(d18:1/24:1) | 0.000011 | −34.086320 |
| CE 20:4/Cer(d18:1/18:0) | 0.000017 | −31.313949 |
| CE 18:3/LacCer(d18:1/20:0) | 0.000017 | −45.652383 |
| CE 18:3/Cer(d18:1/20:0) | 0.000019 | −34.938575 |
| CE 17:1/Cer(d18:1/24:1) | 0.000020 | −27.626744 |
| CE 18:3/Cer(d18:1/18:0) | 0.000022 | −39.797182 |
| CE 18:3/PS O-16:0/18:2-alkenyl | 0.000023 | −40.724368 |
| CE 18:3/PS O-16:1/18:2-alkyl | 0.000023 | −40.724368 |
| CE 18:3/PC O-34:1 | 0.000025 | −36.379680 |
| CE 18:3/Total DAG | 0.000025 | −40.454303 |
| CE 18:3/PC 16:0/16:0 | 0.000026 | −31.169278 |
| CE 18:2/Cer(d18:1/24:1) | 0.000027 | −23.500781 |
| Cer(d18:0/22:0)/Cer(d18:1/18:0) | 0.000031 | −38.447200 |
| CE 18:3/Total Cer | 0.000034 | −30.424215 |
| Cer(d18:0/22:0)/PS O-16:0/18: 2-alkenyl | 0.000045 | −37.930990 |
| Cer(d18:0/22:0)/PS O-16:1/18:2-alkyl | 0.000045 | −37.930990 |
| LPC 18:2/LacCer(d18:1/20:0) | 0.000045 | −40.925010 |
| PC 18:0/20:4/PS O-16:0/18:2-alkenyl | 0.000046 | −31.467609 |
| PC 18:0/20:4/PS O-16:1/18:2-alkyl | 0.000046 | −31.467609 |
| PC 16:0/20:4/Total DAG | 0.000046 | −36.637600 |
| CE 16:0/Cer(d18:1/18:0) | 0.000047 | −26.423623 |

TABLE 5-continued

Table of significant lipid to lipid ratios in LURIC study sorted by p-value. Lipid names, p-values, % change both for positive and negative correlation are presented. Table 5a shows significant lipids from all study subjects. The significant lipids from subjects not undergoing statin treatment are listed in table 5b.

| Lipid name/lipid name | p-value | Percentage change |
|---|---|---|
| Cer(d18:0/22:0)/Cer(d18:1/20:0) | 0.000051 | −32.923442 |
| PC 16:0/20:3/PS O-16:0/18:2-alkenyl | 0.000051 | −30.612669 |
| PC 16:0/20:3/PS O-16:1/18: 2-alkyl | 0.000051 | −30.612669 |
| Cer(d18:0/24:0)/Cer(d18:1/18:0) | 0.000052 | −41.966868 |
| CE 17:1/Cer(d18:1/18:0) | 0.000062 | −30.441023 |
| CE 20:4/LacCer(d18:1/20:0) | 0.000062 | −34.937892 |
| Cer(d18:0/24:0)/Cer(d18:1/20:0) | 0.000077 | −36.424116 |
| CE 18:3/GlcCer(d18:1/20:0) | 0.000078 | −38.775015 |
| PC 16:0/20:4/PS O-16:0/18: 2-alkenyl | 0.000079 | −31.649115 |
| PC 16:0/20:4/PS O-16:1/18:2-alkyl | 0.000079 | −31.649115 |
| Cer(d18:0/24:0)/PS O-16:0/18:2-alkenyl | 0.000082 | −40.069396 |
| Cer(d18:0/24:0)/PS O-16:1/18:2-alkyl | 0.000082 | −40.069396 |
| Cer(d18:0/24:0)/Total Cer | 0.000091 | −30.775984 |
| Cer(d18:0/22:0)/Total DAG | 0.000096 | −39.183597 |
| CE 18:3/Cer(d18:1/16:0) | 0.000101 | −32.942871 |
| PC 18:1/18:2/PS O-16:0/18:2-alkenyl | 0.000106 | −24.667433 |
| PC 18:1/18:2/PS O-16:1/18:2-alkyl | 0.000106 | −24.667433 |
| CE 18:3/Cer(d18:1/22:0) | 0.000109 | −30.876034 |
| CE 14:0/Cer(d18:1/18:0) | 0.000117 | −35.001327 |
| PC 18:0/20:3/PS O-16:0/18: 2-alkenyl | 0.000119 | −29.825217 |

TABLE 6

Table of significant lipid to clinical ratios in LURIC study sorted by p-value. Lipid names and clinical measurement, p-values and percentage change both for positive and negative correlation are presented. Table 6a shows significant lipids from all study subjects. The significant lipids from subjects not undergoing statin treatment are listed in table 6b

| Lipid name/clinical measurement | p-value | Percentage change |
|---|---|---|
| 6a) Significant lipid to clinical ratios in LURIC study sorted by p-value from all study subjects. | | |
| Positive correlation | | |
| LacCer(d18:1/20:0)/apolipoprotein A-I (mg/dL) | 0.00000 | 43.04967 |
| LacCer(d18:1/20:0)/total cholesterol (EDTA) (mg/dL) | 0.00000 | 41.46919 |
| LacCer(d18:1/22:0)/total cholesterol (EDTA) (mg/dL) | 0.00000 | 32.24669 |
| LacCer(d18:1/20:0)/triglycerides (EDTA) (mg/dL) | 0.00001 | 54.05564 |
| LacCer(d18:1/22:0)/apolipoprotein A-I (mg/dL) | 0.00001 | 32.96039 |
| Cer(d18:1/18:0)/triglycerides (EDTA) (mg/dL) | 0.00001 | 40.06643 |
| Cer(d18:1/18:0)/total cholesterol (EDTA) (mg/dL) | 0.00002 | 31.56099 |
| LacCer(d18:1/20:0)/apolipoprotein B (mg/dL) | 0.00002 | 37.03057 |
| Cer(d18:1/20:0)/triglycerides (EDTA) (mg/dL) | 0.00003 | 34.46408 |
| Cer(d18:1/20:0)/total cholesterol (EDTA) (mg/dL) | 0.00003 | 25.23403 |
| LacCer(d18:1/18:0)/triglycerides (EDTA) (mg/dL) | 0.00004 | 52.60972 |
| LacCer(d18:1/24:1)/triglycerides (EDTA) (mg/dL) | 0.00004 | 60.79934 |
| LacCer(d18:1/22:0)/apolipoprotein B (mg/dL) | 0.00004 | 29.83861 |
| Cer(d18:1/20:0)/apolipoprotein A-I (mg/dL) | 0.00004 | 31.35691 |
| LacCer(d18:1/18:0)/total cholesterol (EDTA) (mg/dL) | 0.00005 | 38.87517 |
| Cer(d18:1/24:1)/triglycerides (EDTA) (mg/dL) | 0.00005 | 32.27486 |
| LacCer(d18:1/20:0)/HDL cholesterol (EDTA) (mg/dL) | 0.00006 | 39.32664 |
| LacCer(d18:1/22:0)/triglycerides (EDTA) (mg/dL) | 0.00006 | 49.54525 |
| LacCer(d18:1/18:0)/apolipoprotein A-I (mg/dL) | 0.00007 | 41.61371 |
| LacCer(d18:1/24:1)/total cholesterol (EDTA) (mg/dL) | 0.00007 | 36.35465 |
| Total LacCer/total cholesterol (EDTA) (mg/dL) | 0.00008 | 23.69633 |
| Cer(d18:1/18:0)/apolipoprotein A-I (mg/dL) | 0.00008 | 37.38237 |
| Cer(d18:1/24:1)/total cholesterol (EDTA) (mg/dL) | 0.00011 | 21.94547 |
| Cer(d18:1/24:1)/apolipoprotein A-I (mg/dL) | 0.00011 | 27.12684 |
| Cer(d18:1/18:0)/apolipoprotein B (mg/dL) | 0.00017 | 27.27914 |
| LacCer(d18:1/20:0)/total-c/HDL-c | 0.00018 | 33.48550 |
| LacCer(d18:1/24:1)/apolipoprotein A-I (mg/dL) | 0.00018 | 36.33201 |
| Total LacCer/triglycerides (EDTA) (mg/dL) | 0.00022 | 38.52220 |
| LacCer(d18:1/24:1)/apolipoprotein B (mg/dL) | 0.00022 | 33.98045 |
| LacCer(d18:1/18:0)/apolipoprotein B (mg/dL) | 0.00022 | 33.69302 |
| LacCer(d18:1/22:0)/HDL cholesterol (EDTA) (mg/dL) | 0.00024 | 29.19905 |
| Total LacCer/apolipoprotein A-I (mg/dL) | 0.00025 | 25.87122 |
| PC 0-32:0 (KDdiA-PC)/triglycerides (EDTA) (mg/dL) | 0.00029 | 48.31010 |
| LacCer(d18:1/20:0)/LDL cholesterol (EDTA) (mg/dL) | 0.00031 | 31.95659 |
| Cer(d18:1/22:0)/triglycerides (EDTA) (mg/dL) | 0.00037 | 28.23304 |
| Total Cer/triglycerides (EDTA) (mg/dL) | 0.00043 | 26.80115 |
| LacCer(d18:1/22:0)/LDL cholesterol (EDTA) (mg/dL) | 0.00050 | 24.24011 |
| Cer(d18:1/20:0)/apolipoprotein B (mg/dL) | 0.00052 | 20.79615 |
| LacCer(d18:1/22:0)/total-c/HDL-c | 0.00061 | 27.84411 |
| Total LacCer/apolipoprotein B (mg/dL) | 0.00065 | 20.63257 |

TABLE 6-continued

Table of significant lipid to clinical ratios in LURIC study sorted by p-value. Lipid names and clinical measurement, p-values and percentage change both for positive and negative correlation are presented. Table 6a shows significant lipids from all study subjects. The significant lipids from subjects not undergoing statin treatment are listed in table 6b

| Lipid name/clinical measurement | p-value | Percentage change |
|---|---|---|
| PC O-34:1/triglycerides (EDTA) (mg/dL) | 0.00066 | 38.80785 |
| PC O-32:0 (KDdiA-PC)/apolipoprotein A-I (mg/dL) | 0.00066 | 36.57664 |
| Cer(d18:1/20:0)/HDL cholesterol (EDTA) (mg/dL) | 0.00067 | 30.67863 |
| LacCer(d18:1/18:0)/total-c/HDL-c | 0.00073 | 30.67436 |
| PS O-18:2/16:0-alkenyl/HDL cholesterol (EDTA) (mg/dL) | 0.00073 | 57.54661 |
| LacCer(d18:1/18:0)/HDL cholesterol (EDTA) (mg/dL) | 0.00079 | 38.04132 |
| Cer(d18:1/16:0)/triglycerides (EDTA) (mg/dL) | 0.00083 | 28.51323 |
| Cer(d18:1/18:0)/HDL cholesterol (EDTA) (mg/dL) | 0.00085 | 36.16483 |
| Cer(d18:1/18:0)/total-c/HDL-c | 0.00087 | 21.75165 |
| LacCer(d18:1/20:0)/apoA 1/apoB | 0.00090 | 32.36387 |
| Negative correlation | | |
| CE 18:3/apolipoprotein B (mg/dL) | 0.00016 | −25.31907 |
| CE 18:3/total cholesterol (EDTA) (mg/dL) | 0.00026 | −23.67665 |
| CE 18:3/LDL cholesterol (EDTA) (mg/dL) | 0.00052 | −27.21759 |
| CE 18:3/apolipoprotein A-I (mg/dL) | 0.00054 | −23.09816 |
| CE 18:3/LDL-c/HDL-c | 0.00060 | −31.33346 |
| CE 18:3/apoA1/apoB | 0.00068 | −27.55825 |
| CE 18:3/total-c/HDL-c | 0.00070 | −27.28733 |
| CE 18:3/HDL cholesterol (EDTA) (mg/dL) | 0.00072 | −24.04060 |
| Cer(d18:0/24:0)/apolipoprotein B (mg/dL) | 0.00181 | −26.25271 |
| CE 14:0/LDL-c/HDL-c | 0.00241 | −27.07756 |
| Cer(d18:0/24:0)/total cholesterol (EDTA) (mg/dL) | 0.00281 | −24.73116 |
| Cer(d18:0/24:0)/total-c/HDL-c | 0.00347 | −27.84469 |
| CE 14:0/total-c/HDL-c | 0.00356 | −23.22809 |
| PC 16:0/20:3/total-c/HDL-c | 0.00364 | −19.07121 |
| CE 14:0/apolipoprotein B (mg/dL) | 0.00375 | −19.76414 |
| Total PC/LDL-c/HDL-c | 0.00402 | −21.24583 |
| Cer(d18:0/24:0)/LDL-c/HDL-c | 0.00502 | −33.76759 |
| Total PC/apolipoprotein B (mg/dL) | 0.00513 | −12.91145 |
| Total PC/total-c/HDL-c | 0.00535 | −16.13350 |
| CE 20:3/LDL-c/HDL-c | 0.00547 | −21.16631 |
| PC 16:0/20:4/apolipoprotein B (mg/dL) | 0.00576 | −15.39247 |
| PC 16:0/20:4/total-c/HDL-c | 0.00682 | −18.06323 |
| Cer(d18:0/22:0)/LDL-c/HDL-c | 0.00748 | −29.05891 |
| Total PC/total cholesterol (EDTA) (mg/dL) | 0.00760 | −10.60231 |
| Cer(d18:0/22:0)/total-c/HDL-c | 0.00765 | −23.72182 |
| PC 16:0/20:3/LDL-c/HDL-c | 0.00784 | −22.56336 |
| PC 18:0/20:3/total-c/HDL-c | 0.00794 | −17.83335 |
| CE 14:0/total cholesterol (EDTA) (mg/dL) | 0.00816 | −17.44260 |
| CE 20:3/total-c/HDL-c | 0.00819 | −17.34055 |
| PC 16:0/20:4/LDL-c/HDL-c | 0.00828 | −21.49898 |
| CE 17:1/LDL-c/HDL-c | 0.00832 | −21.33179 |
| CE 14:0/LDL cholesterol (EDTA) (mg/dL) | 0.00832 | −20.55966 |
| Cer(d18:0/24:0)/LDL cholesterol (EDTA) (mg/dL) | 0.00848 | −30.08563 |
| LPC 18:2/LDL-c/HDL-c | 0.00873 | −21.70580 |
| Total LPC/LDL-c/HDL-c | 0.00881 | −20.39287 |
| PC 18:0/20:3/LDL-c/HDL-c | 0.00947 | −22.19538 |
| Cer(d18:0/24:0)/apolipoprotein A-I (mg/dL) | 0.01052 | −22.39254 |
| Cer(d18:0/22:0)/apolipoprotein B (mg/dL) | 0.01094 | −21.02661 |
| CE 20:3/apolipoprotein B (mg/dL) | 0.01105 | −15.18746 |
| PC 16:0/20:4/total cholesterol (EDTA) (mg/dL) | 0.01131 | −13.37554 |
| Total LPC/total-c/HDL-c | 0.01183 | −16.82334 |
| LPC 18:2/apoA1/apoB | 0.01189 | −19.23316 |
| PC 16:0/20:3/apolipoprotein B (mg/dL) | 0.01273 | −15.11848 |
| CE 16:1/apolipoprotein B (mg/dL) | 0.01456 | 26.99397 |
| Cer(d18:0/24:0)/HDL cholesterol (EDTA) (mg/dL) | 0.01507 | −23.10073 |
| CE 16:1/LDL cholesterol (EDTA) (mg/dL) | 0.01581 | −29.68280 |
| PC 18:0/18:1/LDL-c/HDL-c | 0.01581 | −25.72002 |
| CE 20:5/HDL cholesterol (EDTA) (mg/dL) | 0.01584 | −23.45029 |
| CE 20:5/apolipoprotein B (mg/dL) | 0.01619 | −27.03163 |
| LPC 18:2/LDL cholesterol (EDTA) (mg/dL) | 0.01648 | −17.26480 |
| 6b) Significant lipid to clinical ratios in LURIC study sorted by p-value from subjects not undergoing statin treatment. | | |
| Positive correlation | | |
| Cer(d18:1/20:0)/total cholesterol (EDTA) (mg/dL) | 0.00000 | 38.78716 |
| Cer(d18:1/20:0)/apolipoprotein B (mg/dL) | 0.00000 | 35.29473 |
| Cer(d18:1/18:0)/total cholesterol (EDTA) (mg/dL) | 0.00000 | 44.87416 |

TABLE 6-continued

Table of significant lipid to clinical ratios in LURIC study sorted by p-value.
Lipid names and clinical measurement, p-values and
percentage change both for positive and negative
correlation are presented. Table 6a shows significant lipids from
all study subjects. The significant lipids from subjects not
undergoing statin treatment are listed in table 6b

| Lipid name/clinical measurement | p-value | Percentage change |
|---|---|---|
| Cer(d18:1/24:1)/total cholesterol (EDTA) (mg/dL) | 0.00000 | 31.81230 |
| Cer(d18:1/18:0)/apolipoprotein B (mg/dL) | 0.00000 | 41.46939 |
| Cer(d18:1/20:0)/apolipoprotein A-I (mg/dL) | 0.00000 | 43.22923 |
| Cer(d18:1/24:1)/apolipoprotein A-I (mg/dL) | 0.00000 | 36.15491 |
| LacCer(d18:1/20:0)/apolipoprotein A-I (mg/dL) | 0.00001 | 47.52465 |
| Cer(d18:1/18:0)/apolipoprotein A-I (mg/dL) | 0.00001 | 49.43693 |
| LacCer(d18:1/20:0)/total cholesterol (EDTA) (mg/dL) | 0.00001 | 47.43498 |
| Cer(d18:1/22:0)/total cholesterol (EDTA) (mg/dL) | 0.00001 | 26.21569 |
| LacCer(d18:1/22:0)/total cholesterol (EDTA) (mg/dL) | 0.00001 | 36.57029 |
| Cer(d18:1/24:1)/apolipoprotein B (mg/dL) | 0.00001 | 29.03655 |
| LacCer(d18:1/22:0)/apolipoprotein A-I (mg/dL) | 0.00001 | 35.92744 |
| Cer(d18:1/18:0)/triglycerides (EDTA) (mg/dL) | 0.00002 | 45.88769 |
| Cer(d18:1/20:0)/triglycerides (EDTA) (mg/dL) | 0.00002 | 41.38147 |
| LacCer(d18:1/20:0)/apolipoprotein B (mg/dL) | 0.00002 | 43.58427 |
| Total Cer/total cholesterol (EDTA) (mg/dL) | 0.00002 | 22.69184 |
| Total DAG/triglycerides (EDTA) (mg/dL) | 0.00003 | 42.61436 |
| LacCer(d18:1/20:0)/LDL cholesterol (EDTA) (mg/dL) | 0.00003 | 42.53680 |
| Cer(d18:1/18:0)/total-c/HDL-c | 0.00003 | 32.87649 |
| Cer(d18:1/24:1)/triglycerides (EDTA) (mg/dL) | 0.00004 | 37.38060 |
| Cer(d18:1/20:0)/HDL cholesterol (EDTA) (mg/dL) | 0.00004 | 44.64484 |
| LacCer(d18:1/22:0)/apolipoprotein B (mg/dL) | 0.00004 | 35.19942 |
| Cer(d18:1/22:0)/apolipoprotein B (mg/dL) | 0.00005 | 24.23877 |
| LacCer(d18:1/24:1)/total cholesterol (EDTA) (mg/dL) | 0.00006 | 43.51653 |
| LacCer(d18:1/20:0)/HDL cholesterol (EDTA) (mg/dL) | 0.00006 | 45.00931 |
| Total LacCer/total cholesterol (EDTA) (mg/dL) | 0.00007 | 27.38505 |
| Cer(d18:1/18:0)/HDL cholesterol (EDTA) (mg/dL) | 0.00008 | 50.71310 |
| Cer(d18:1/24:1)/HDL cholesterol (EDTA) (mg/dL) | 0.00008 | 36.69128 |
| LacCer(d18:1/20:0)/triglycerides (EDTA) (mg/dL) | 0.00009 | 53.20068 |
| LacCer(d18:1/24:1)/apolipoprotein B (mg/dL) | 0.00009 | 42.74199 |
| Cer(d18:1/20:0)/total-c/HDL-c | 0.00010 | 26.38965 |
| LacCer(d18:1/22:0)/LDL cholesterol (EDTA) (mg/dL) | 0.00010 | 31.99739 |
| Cer(d18:1/22:0)/apolipoprotein A-I (mg/dL) | 0.00011 | 28.85911 |
| LacCer(d18:1/24:1)/triglycerides (EDTA) (mg/dL) | 0.00013 | 64.74061 |
| Total Cer/apolipoprotein B (mg/dL) | 0.00015 | 21.06506 |
| Total Cer/apolipoprotein A-I (mg/dL) | 0.00016 | 25.36811 |
| Cer(d18:1/16:0)/total cholesterol (EDTA) (mg/dL) | 0.00016 | 27.48182 |
| LacCer(d18:1/24:1)/apolipoprotein A-I (mg/dL) | 0.00017 | 41.35186 |
| Cer(d18:1/20:0)/LDL cholesterol (EDTA) (mg/dL) | 0.00018 | 35.64759 |
| LacCer(d18:1/18:0)/total cholesterol (EDTA) (mg/dL) | 0.00019 | 42.30922 |
| LacCer(d18:1/22:0)/HDL cholesterol (EDTA) (mg/dL) | 0.00020 | 33.63345 |
| LacCer(d18:1/18:0)/apolipoprotein A-I (mg/dL) | 0.00022 | 44.38352 |
| Cer(d18:1/18:0)/LDL cholesterol (EDTA) (mg/dL) | 0.00023 | 42.34532 |
| Total LacCer/apolipoprotein A-I (mg/dL) | 0.00031 | 28.05057 |
| Total LacCer/apolipoprotein B (mg/dL) | 0.00035 | 24.82894 |
| Cer(d18:1/22:0)/triglycerides (EDTA) (mg/dL) | 0.00039 | 32.11726 |
| LacCer(d18:1/20:0)/total-c/HDL-c | 0.00040 | 37.19117 |
| Cer(d18:1/16:0)/apolipoprotein A-I (mg/dL) | 0.00042 | 30.73655 |
| Negative correlation | | |
| CE 18:3/apoA1/apoB | 0.00213 | −27.06449 |
| CE 18:3/apolipoprotein A-I (mg/dL) | 0.00385 | −21.63982 |
| CE 18:3/apolipoprotein B (mg/dL) | 0.00576 | −21.66212 |
| CE 18:3/total cholesterol (EDTA) (mg/dL) | 0.00593 | −20.58905 |
| CE 18:3/HDL cholesterol (EDTA) (mg/dL) | 0.00621 | −21.44255 |
| CE 18:3/total-c/HDL-c | 0.01166 | −23.94433 |
| CE 18:3/LDL-c/HDL-c | 0.01395 | −25.96634 |
| CE 18:3/LDL cholesterol (EDTA) (mg/dL) | 0.01410 | −22.13225 |
| CE 14:0/total-c/HDL-c | 0.02379 | −20.97683 |
| CE 14:0/LDL-c/HDL-c | 0.03038 | −22.86773 |
| Cer(d18:0/24:0)/apolipoprotein B (mg/dL) | 0.03428 | −21.10483 |
| CE 14:0/apolipoprotein B (mg/dL) | 0.03640 | −16.53355 |
| Cer(d18:0/24:0)/total-c/HDL-c | 0.04122 | −23.22174 |
| Cer(d18:0/24:0)/total cholesterol (EDTA) (mg/dL) | 0.04309 | −19.71324 |
| CE 14:0/apoA1/apoB | 0.04354 | −18.62921 |
| CE 16:1/apoA1/apoB | 0.04511 | −23.73367 |

The biomarker ability of measured lipids was assessed also by calculating the sensitivity and specificity values for each lipid and their ratios to other lipids or classical biomarkers such as LDL-C and apolipoproteins. This ROC curve analysis revealed a number of biomarker candidates that have equal of higher than 60% sensitivity and specificity for predicting CVD complications (Tables 7-9).

TABLE 7

Significant lipids in LURIC study sorted by top sensitivity and specificity. Table 7a shows significant lipids from all study subjects. The significant lipids from subjects not undergoing statin treatment are listed in table 7b.

| Lipid name | Sensitivity | Specificity | Percentage change |
|---|---|---|---|
| 7a) Significant lipids in LURIC study sorted by top sensitivity and specificity from all study subjects. | | | |
| Positive correlation | | | |
| LacCer(d18:1/20:0) | 66.03774 | 63.70370 | 29.52421 |
| Total LacCer | 63.15789 | 60.12270 | 13.83938 |
| Cer(d18:1/24:1) | 61.40351 | 60.12270 | 14.88898 |
| Negative correlation | | | |
| Total PC | 71.92982 | 63.29114 | −16.07367 |
| PC 16:0/20:3 | 71.42857 | 60.75949 | −18.78110 |
| Total LPC | 70.17544 | 60.75949 | −17.02070 |
| PC 18:0/20:3 | 66.03774 | 63.05732 | −17.20664 |
| LPC 18:1 | 64.91228 | 60.12658 | −14.45827 |
| SM (d18:1/14:0) (d18:1/13:1-OH) | 63.79310 | 60.50955 | −10.49341 |
| Cer(d18:0/22:0) | 61.40351 | 61.34969 | −22.37263 |
| PC 16:0/18:2 | 61.40351 | 60.12658 | −8.30551 |
| PC 16:0/22:6 | 60.37736 | 61.14650 | −16.65050 |
| 7b) Significant lipids in LURIC study sorted by top sensitivity and specificity from subjects not undergoing statin treatment. | | | |
| Positive correlation | | | |
| LacCer(d18:1/20:0) | 70.45455 | 60.00000 | 29.52421 |
| Cer(d18:1/24:1) | 69.56522 | 60.34483 | 14.88898 |
| Cer(d18:1/20:0) | 65.21739 | 64.65517 | 17.32385 |
| Cer(d18:1/22:0) | 60.86957 | 62.93103 | 10.65433 |
| GlcCer(d18:1/24:1) | 60.86957 | 62.06897 | 12.75066 |
| LacCer(d18:1/22:0) | 60.00000 | 61.76471 | 22.75541 |
| Negative correlation | | | |
| Total PC | 69.56522 | 61.60714 | −16.07367 |
| PC 16:0/20:3 | 64.44444 | 60.71429 | −18.78110 |
| SM (d18:1/14:0) (d18:1/13:1-OH) | 63.82979 | 60.71429 | −10.49341 |
| LPC 18:1 | 63.04348 | 60.71429 | −14.45827 |
| Total LPC | 63.04348 | 60.71429 | −17.02070 |
| PC O-40:3 | 60.97561 | 60.43956 | −1.88354 |
| PC 16:0/20:4 | 60.86957 | 60.71429 | −18.06547 |

TABLE 8

Table of significant lipid to lipid ratios in LURIC study sorted by top sensitivity and specificity. Table 8a shows significant lipids from all study subjects. The significant lipids from subjects not undergoing statin treatment are listed in table 8b.

| Lipid name/Lipid name | Sensitivity | Specificity | Percentage change |
|---|---|---|---|
| 8a) Table of significant lipid to lipid ratios in LURIC study sorted by top sensitivity and specificity from all study subjects. | | | |
| Positive correlation | | | |
| PS O-16:0/18:2-alkenyl/Total PS O | 98.24561 | 63.92405 | 26.07240 |
| PS O-16:1/18:2-alkyl/Total PS O | 98.24561 | 63.92405 | 26.07240 |
| PS O-18:2/16:0-alkenyl/Total PS O | 85.45455 | 70.66667 | 28.78267 |
| LacCer(d18:1/20:0)/PC 16:0/20:3 | 80.39216 | 65.11628 | 57.24752 |
| CE 18:2/CE 18:3 | 79.31034 | 60.37736 | 26.34366 |
| LacCer(d18:1/20:0)/Total LPC | 78.84615 | 61.24031 | 53.68111 |
| LacCer(d18:1/20:0)/Total PC | 78.84615 | 64.34109 | 55.30769 |
| LacCer(d18:1/20:0)/PC 18:0/20:3 | 77.08333 | 60.15625 | 56.31253 |
| Cer(d18:1/24:1)/LPC 18:2 | 75.92593 | 63.69427 | 48.79017 |
| CE 16:0/CE 18:3 | 75.86207 | 60.37736 | 25.64615 |
| LacCer(d18:1/20:0)/Total SM | 75.47170 | 60.60606 | 29.12486 |
| Cer(d18:1/16:0)/Total PC | 75.00000 | 61.14650 | 32.91697 |
| Cer(d18:1/18:0)/PC 16:0/20:4 | 75.00000 | 63.05732 | 65.70609 |
| Cer(d18:1/18:0)/Total LPC | 75.00000 | 61.14650 | 45.10211 |
| Cer(d18:1/24:1)/SM (d18:1/24:0) (d18:1/23:1-OH) | 75.00000 | 62.42038 | 36.77357 |
| Cer(d18:1/24:1)/Total LPC | 75.00000 | 63.05732 | 37.58734 |
| Cer(d18:1/24:1)/Total PC | 75.00000 | 60.50955 | 38.66127 |
| LacCer(d18:1/18:0)/Total LPC | 75.00000 | 60.13072 | 55.13308 |
| LacCer(d18:1/20:0)/SM (d18:1/17:1-OH) | 75.00000 | 62.60163 | 36.30844 |
| LacCer(d18:1/20:0)/SM (d18:1/18:0) | 75.00000 | 62.60163 | 36.30844 |
| Total Cer/Total PC | 75.00000 | 63.92405 | 28.86380 |
| LacCer(d18:1/24:0)/Total LPC | 74.54545 | 61.94030 | 36.27249 |
| LacCer(d18:1/20:0)/PC 18:2/18:2 | 74.46809 | 60.31746 | 47.81762 |
| PC 16:0/16:0/Total PC | 73.68421 | 65.18987 | 26.13285 |
| Cer(d18:1/22:0)/Total PC | 73.21429 | 61.78344 | 31.36049 |
| GlcCer(d18:1/20:0)/Total PC | 73.21429 | 60.50955 | 36.81380 |
| LacCer(d18:1/16:0)/Total LPC | 73.21429 | 60.50955 | 26.35547 |
| LacCer(d18:1/18:0)/Total PC | 73.21429 | 61.43791 | 53.58552 |
| LacCer(d18:1/22:0)/SM (d18:1/14:0) | 73.21429 | 60.00000 | 30.07361 |

TABLE 8-continued

Table of significant lipid to lipid ratios in LURIC study sorted by top sensitivity and specificity. Table 8a shows significant lipids from all study subjects. The significant lipids from subjects not undergoing statin treatment are listed in table 8b.

| Lipid name/Lipid name | Sensitivity | Specificity | Percentage change |
|---|---|---|---|
| (d18:1/13:1-OH) | | | |
| Total LacCer/Total PC | 73.21429 | 60.50955 | 40.03890 |
| LacCer(d18:1/20:0)/PC 16:0/18:1 | 73.07692 | 62.01550 | 46.35288 |
| LacCer(d18:1/20:0)/PC 18:1/18:2 | 73.07692 | 60.46512 | 47.48070 |
| Cer(d18:1/26:0)/PC O-40:0 | 72.72727 | 62.22222 | 9.97951 |
| LacCer(d18:1/22:0)/Total LPC | 72.72727 | 64.92537 | 41.61463 |
| LacCer(d18:1/24:1)/Total LPC | 72.72727 | 60.44776 | 45.29327 |
| PC O-18:0/18:2-alkyl/PC O-36:5 | 72.72727 | 61.18421 | 25.99402 |
| PC O-32:0 (KDdiA-PC)/PC O-38:5 | 72.54902 | 61.36364 | 34.00112 |
| Cer(d18:1/22:0)/LPC 18:2 | 72.22222 | 61.78344 | 41.72749 |
| LacCer(d18:1/22:0)/PC 16:0/20:3 | 72.22222 | 66.41791 | 51.38070 |
| LacCer(d18:1/24:0)/PC 16:0/20:3 | 72.22222 | 61.19403 | 39.48118 |
| Cer(d18:1/24:1)/Total CE | 71.92982 | 61.39241 | 31.32927 |
| PC 16:0/16:0/PC 16:0/20:4 | 71.92982 | 61.39241 | 38.61464 |
| PC 16:0/18:2/Total PC | 71.92982 | 60.75949 | 8.88941 |
| Total LacCer/Total PC O | 71.92982 | 60.24845 | 17.49430 |
| Cer(d18:1/16:0)/LPC 18:1 | 71.42857 | 63.69427 | 30.55279 |
| Cer(d18:1/18:0)/LPC 16:0 | 71.42857 | 61.14650 | 40.41256 |
| Cer(d18:1/18:0)/LPC 18:1 | 71.42857 | 61.78344 | 45.33865 |
| GlcCer(d18:1/20:0)/PC 16:0/20:4 | 71.42857 | 60.50955 | 46.04915 |
| LacCer(d18:1/24:1)/Total PC O | 71.42857 | 60.14493 | 21.09716 |
| CE 19:1/Cer(d18:0/22:0) | 71.15385 | 60.14493 | 39.21301 |
| Negative correlation | | | |
| CE 18:3/LacCer(d18:1/20:0) | 84.90566 | 62.87879 | -44.30634 |
| CE 18:3/Cer(d18:1/24:1) | 80.70175 | 60.12658 | -35.95912 |
| Cer(d18:0/24:0)/Total Cer | 80.70175 | 60.12270 | -31.45318 |
| LPC 18:2/LacCer(d18:1/20:0) | 80.00000 | 64.34109 | -41.66044 |
| CE 18:3/Total CE | 79.31034 | 61.00629 | -20.28821 |
| GlcCer(d18:1/26:0)/LacCer(d18:1/20:0) | 79.16667 | 61.40351 | -23.71130 |
| CE 16:1/Cer(d18:1/20:0) | 78.94737 | 61.39241 | -33.84979 |
| CE 16:1/Cer(d18:1/24:1) | 77.19298 | 61.39241 | -36.17234 |
| CE 16:1/LacCer(d18:1/18:0) | 77.19298 | 60.38961 | -37.93756 |
| CE 18:3/Cer(d18:1/20:0) | 77.19298 | 60.75949 | -33.62034 |
| LPC 18:1/LacCer(d18:1/20:0) | 76.92308 | 63.56589 | -34.40451 |
| CE 18:3/LacCer(d18:1/22:0) | 76.78571 | 61.02941 | -37.15258 |
| CE 16:1/CE 19:1 | 75.47170 | 60.86957 | -66.77151 |
| CE 16:1/Cer(d18:1/18:0) | 75.43860 | 61.39241 | -39.42716 |
| CE 16:1/LacCer(d18:1/16:0) | 75.43860 | 60.12658 | -30.53235 |
| CE 16:1/Total LacCer | 75.43860 | 60.75949 | -34.87060 |
| CE 18:3/PC 16:0/16:0 | 75.43860 | 60.00000 | -30.47160 |
| CE 18:3/PS O-16:0/18:2-alkenyl | 75.43860 | 60.64516 | -38.50943 |
| CE 18:3/PS O-16:1/18:2-alkyl | 75.43860 | 60.64516 | -38.50943 |
| CE 18:3/Total LacCer | 75.43860 | 63.29114 | -34.13080 |
| Cer(d18:0/24:0)/Cer(d18:1/22:0) | 75.43860 | 66.25767 | -32.40867 |
| CE 16:1/LacCer(d18:1/22:0) | 75.00000 | 61.02941 | -37.29505 |
| CE 16:1/LacCer(d18:1/24:0) | 75.00000 | 60.29412 | -36.84318 |
| GlcCer(d18:1/26:0)/LacCer(d18:1/22:0) | 75.00000 | 60.86957 | -20.64622 |
| LPC 16:0/LacCer(d18:1/20:0) | 75.00000 | 61.24031 | -35.61882 |
| Total LPC/Total LacCer | 75.00000 | 61.78344 | -26.08820 |
| LPC 16:0/LacCer(d18:1/24:1) | 74.54545 | 60.44776 | -24.61533 |
| CE 17:1/GlcCer(d18:1/24:1) | 74.07407 | 60.25641 | -24.94421 |
| CE 16:1/GlcCer(d18:1/18:0) | 73.68421 | 60.12658 | -36.48698 |
| CE 16:1/GlcCer(d18:1/20:0) | 73.68421 | 60.75949 | -38.30453 |
| CE 16:1/PC 16:0/16:0 | 73.68421 | 60.64516 | -29.10430 |
| CE 18:1/Total LacCer | 73.68421 | 60.12658 | -20.87773 |
| CE 18:3/Cer(d18:1/16:0) | 73.68421 | 67.08861 | -32.55987 |
| CE 18:3/Cer(d18:1/22:0) | 73.68421 | 61.39241 | -30.65953 |
| CE 20:3/Cer(d18:1/24:1) | 73.68421 | 61.39241 | -28.12167 |
| Cer(d18:0/22:0)/Cer(d18:1/24:1) | 73.68421 | 61.96319 | -32.18870 |
| Cer(d18:0/24:0)/Cer(d18:1/18:0) | 73.68421 | 63.80368 | -40.29603 |
| Cer(d18:0/24:0)/Cer(d18:1/24:1) | 73.68421 | 65.64417 | -36.12881 |
| Cer(d18:0/24:0)/GlcCer(d18:1/20:0) | 73.68421 | 60.73620 | -40.34621 |
| CE 16:1/LacCer(d18:1/20:0) | 73.58491 | 62.12121 | -39.47654 |
| CE 20:3/LacCer(d18:1/20:0) | 73.58491 | 62.12121 | -35.94789 |
| CE 18:3/LacCer(d18:1/24:0) | 73.21429 | 62.50000 | -35.91095 |
| CE 18:3/PS O-16:0/18:1-alkenyl (PS O-16:1/18:1-alkyl) | 73.21429 | 60.64516 | -34.16720 |
| Cer(d18:0/22:0)/LacCer(d18:1/24:0) | 73.21429 | 60.00000 | -31.24173 |
| Cer(d18:0/24:0)/LacCer(d18:1/24:0) | 73.21429 | 62.85714 | -37.02872 |
| LPC 16:0/Total LacCer | 73.21429 | 61.78344 | -24.37341 |
| SM (d18:1/24:0) (d18:1/23:1-OH)/Total Cer | 73.21429 | 61.14650 | -13.97590 |

TABLE 8-continued

Table of significant lipid to lipid ratios in LURIC study sorted by top sensitivity and specificity. Table 8a shows significant lipids from all study subjects. The significant lipids from subjects not undergoing statin treatment are listed in table 8b.

| Lipid name/Lipid name | Sensitivity | Specificity | Percentage change |
|---|---|---|---|
| Cer(d18:0/24:0)/SM (d18:1/17:0) (d18:1/16:1-OH) | 72.91667 | 60.00000 | −44.87505 |
| LPC 16:0/LacCer(d18:1/22:0) | 72.72727 | 67.16418 | −27.47521 |
| CE 17:1/LacCer(d18:1/18:0) | 72.22222 | 60.52632 | −27.90709 |

8b) Table of significant lipid to lipid ratios in LURIC study sorted by top sensitivity and specificity from subjects not undergoing statin treatment.

| Lipid name/Lipid name | Sensitivity | Specificity | Percentage change |
|---|---|---|---|
| Positive correlation | | | |
| PS O-16:0/18:2-alkenyl/Total PS O | 97.82609 | 62.50000 | 26.42621 |
| PS O-16:1/18:2-alkyl/Total PS O | 97.82609 | 62.50000 | 26.42621 |
| PS O-18:2/16:0-alkenyl/Total PS O | 88.63636 | 72.64151 | 29.59068 |
| Cer(d18:1/24:1)/LPC 18:2 | 81.39535 | 62.16216 | 51.68188 |
| CE 18:2/CE 18:3 | 80.85106 | 60.52632 | 24.84398 |
| Cer(d18:1/18:0)/PC 16:0/20:4 | 80.00000 | 62.16216 | 73.07370 |
| Cer(d18:1/24:1)/PC 16:0/18:2 | 80.00000 | 60.36036 | 27.45405 |
| Cer(d18:1/24:1)/Total LPC | 80.00000 | 62.16216 | 38.68474 |
| Cer(d18:1/24:1)/Total PC | 80.00000 | 62.16216 | 43.04080 |
| LacCer(d18:1/20:0)/PC 16:0/20:4 | 79.06977 | 68.42105 | 82.44735 |
| LacCer(d18:1/20:0)/PC 16:0/20:3 | 78.57143 | 64.21053 | 56.97265 |
| Cer(d18:1/16:0)/Total PC | 77.77778 | 60.36036 | 34.07762 |
| Cer(d18:1/18:0)/LPC 18:1 | 77.77778 | 60.36036 | 45.52166 |
| Cer(d18:1/24:1)/SM (d18:1/24:0) (d18:1/23:1-OH) | 77.77778 | 60.17699 | 32.27927 |
| Cer(d18:1/24:1)/PC O-40:3 | 77.50000 | 60.43956 | 20.46959 |
| LacCer(d18:1/20:0)/Total LPC | 76.74419 | 60.00000 | 49.56627 |
| LacCer(d18:1/20:0)/Total PC | 76.74419 | 63.15789 | 55.68613 |
| Cer(d18:1/18:0)/Total CE | 76.08696 | 60.17699 | 49.43112 |
| Cer(d18:1/20:0)/SM (d18:1/14:0) (d18:1/13:1-OH) | 76.08696 | 60.71429 | 28.98221 |
| Cer(d18:1/20:0)/Total PC O | 76.08696 | 60.86957 | 29.01076 |
| Cer(d18:1/24:1)/Total CE | 76.08696 | 60.17699 | 39.34990 |
| PS O-16:0/18:2-alkenyl/Total PC O | 76.08696 | 61.60714 | 20.69456 |
| PS O-16:1/18:2-alkyl/Total PC O | 76.08696 | 61.60714 | 20.69456 |
| Cer(d18:1/16:0)/LPC 18:1 | 75.55556 | 60.36036 | 26.36925 |
| Cer(d18:1/18:0)/Total LPC | 75.55556 | 63.06306 | 44.40414 |
| Cer(d18:1/22:0)/Total PC | 75.55556 | 63.06306 | 34.70483 |
| Total Cer/Total PC | 75.55556 | 61.60714 | 29.94912 |
| LacCer(d18:1/20:0)/Total SM | 75.00000 | 61.61616 | 27.48798 |
| LacCer(d18:1/24:0)/Total LPC | 75.00000 | 67.01031 | 34.46432 |
| PS O-18:2/16:0-alkenyl/Total PC O | 75.00000 | 60.37736 | 21.65448 |
| CE 16:0/CE 18:3 | 74.46809 | 61.40351 | 25.51627 |
| CE 18:0/CE 18:3 | 74.46809 | 65.13761 | 29.77017 |
| Cer(d18:1/22:0)/LPC 18:2 | 74.41860 | 60.36036 | 44.40272 |
| LacCer(d18:1/20:0)/PC 18:1/18:2 | 74.41860 | 64.21053 | 48.43279 |
| LacCer(d18:1/20:0)/SM (d18:1/17:1-OH) | 74.41860 | 60.86957 | 34.96305 |
| LacCer(d18:1/20:0)/SM (d18:1/18:0) | 74.41860 | 60.86957 | 34.96305 |
| LacCer(d18:1/20:0)/PC 18:0/20:3 | 74.35897 | 62.76596 | 55.40327 |
| Cer(d18:1/18:0)/SM (d18:1/14:0) (d18:1/13:1-OH) | 73.91304 | 74.10714 | 34.95249 |
| Cer(d18:1/18:0)/SM (d18:1/17:2-OH) | 73.91304 | 60.00000 | 25.13954 |
| Cer(d18:1/18:0)/SM (d18:1/18:1) | 73.91304 | 60.00000 | 25.13954 |
| Cer(d18:1/24:1)/SM (d18:1/23:0) (d18:1/22:1-OH) | 73.91304 | 60.71429 | 29.95139 |
| PC 16:0/16:0/PC 16:0/20:4 | 73.91304 | 60.71429 | 42.51274 |
| Cer(d18:1/20:0)/Total LPC | 73.33333 | 61.26126 | 36.63159 |
| Cer(d18:1/24:1)/PC 16:0/20:4 | 73.33333 | 62.16216 | 59.87613 |
| Cer(d18:1/24:1)/PC 18:0/18:2 | 73.33333 | 62.16216 | 29.37710 |
| Cer(d18:1/24:1)/PC 18:1/18:2 | 73.33333 | 61.26126 | 36.88389 |
| Cer(d18:1/24:1)/SM (d18:1/17:1-OH) | 73.33333 | 64.42308 | 23.41916 |
| Cer(d18:1/24:1)/SM (d18:1/18:0) | 73.33333 | 64.42308 | 23.41916 |
| LacCer(d18:1/20:0)/PC 18:0/18:1 | 73.17073 | 62.10526 | 50.18761 |
| LacCer(d18:1/20:0)/Total CE | 72.72727 | 62.62626 | 53.71776 |
| Negative correlation | | | |
| DAG 16:0/18:1/Total DAG | 88.88889 | 61.16505 | −17.30528 |
| CE 18:3/LacCer(d18:1/20:0) | 86.36364 | 66.66667 | −45.65238 |
| LPC 18:2/LacCer(d18:1/20:0) | 82.92683 | 62.10526 | −40.92501 |
| CE 18:3/Cer(d18:1/24:1) | 82.60870 | 61.06195 | −37.97573 |
| GlcCer(d18:1/26:0)/LacCer(d18:1/20:0) | 80.48780 | 64.77273 | −26.83109 |
| CE 14:0/Total DAG | 80.00000 | 61.16505 | −39.38279 |
| CE 18:3/Total CE | 78.72340 | 62.28070 | −19.58872 |
| PC 18:0/20:3/PS O-16:0/18:2-alkenyl | 78.57143 | 60.36036 | −29.82522 |
| PC 18:0/20:3/PS O-16:1/18:2-alkyl | 78.57143 | 60.36036 | −29.82522 |
| CE 16:1/Cer(d18:1/24:1) | 78.26087 | 61.06195 | −37.53854 |
| CE 18:3/PS O-16:0/18:2-alkenyl | 78.26087 | 60.90909 | −40.72437 |

TABLE 8-continued

Table of significant lipid to lipid ratios in LURIC study sorted by top
sensitivity and specificity. Table 8a shows significant lipids from all study subjects.
The significant lipids from subjects not undergoing statin treatment are listed in table
8b.

| Lipid name/Lipid name | Sensitivity | Specificity | Percentage change |
|---|---|---|---|
| CE 18:3/PS O-16:1/18:2-alkyl | 78.26087 | 60.90909 | −40.72437 |
| CE 18:3/Total LacCer | 78.26087 | 60.17699 | −32.64187 |
| Cer(d18:0/24:0)/Total Cer | 78.26087 | 62.06897 | −30.77598 |
| GlcCer(d18:1/26:0)/LacCer(d18:1/22:0) | 78.04878 | 61.79775 | −21.27116 |
| CE 18:3/LacCer(d18:1/22:0) | 77.77778 | 63.63636 | −34.76187 |
| CE 20:3/LacCer(d18:1/20:0) | 77.27273 | 60.60606 | −36.58675 |
| PC O-40:3/PS O-18:2/16:0-alkenyl | 76.92308 | 62.79070 | −28.59638 |
| LPC 18:1/LacCer(d18:1/20:0) | 76.74419 | 60.00000 | −33.84809 |
| CE 16:0/Cer(d18:1/24:1) | 76.08696 | 61.06195 | −23.25713 |
| CE 16:1/Cer(d18:1/18:0) | 76.08696 | 63.71681 | −41.11023 |
| CE 16:1/Cer(d18:1/20:0) | 76.08696 | 66.37168 | −34.98271 |
| CE 16:1/GlcCer(d18:1/24:1) | 76.08696 | 60.17699 | −39.81218 |
| CE 16:1/LacCer(d18:1/18:0) | 76.08696 | 60.36036 | −37.28535 |
| CE 18:3/Cer(d18:1/20:0) | 76.08696 | 63.71681 | −34.93858 |
| CE 18:3/Cer(d18:1/22:0) | 76.08696 | 61.94690 | −30.87603 |
| Cer(d18:0/22:0)/Cer(d18:1/24:1) | 76.08696 | 61.20690 | −34.08632 |
| Cer(d18:0/22:0)/Total GlcCer | 76.08696 | 60.34483 | −28.95910 |
| Cer(d18:0/24:0)/Cer(d18:1/20:0) | 76.08696 | 60.34483 | −36.42412 |
| PC 18:0/20:3/PS O-18:2/16:0-alkenyl | 75.60976 | 60.95238 | −29.83126 |
| CE 16:1/LacCer(d18:1/24:0) | 75.55556 | 60.60606 | −36.83943 |
| CE 18:3/LacCer(d18:1/24:0) | 75.55556 | 60.60606 | −37.84417 |
| PC 18:1/18:2/Total Cer | 75.55556 | 60.71429 | −19.58862 |
| SM (d18:1/23:0) (d18: 1/22:1-OH)/Total DAG | 75.55556 | 63.10680 | −37.45206 |
| SM (d18:1/24:0) (d18:1/23:1-OH)/Total Cer | 75.55556 | 61.94690 | −11.07113 |
| Total CE/Total DAG | 75.55556 | 66.01942 | −31.35698 |
| Total LPC/Total LacCer | 75.55556 | 69.36937 | −23.44706 |
| CE 16:1/CE 19:1 | 75.00000 | 60.82474 | −56.18741 |
| CE 20:5/LacCer(d18:1/20:0) | 75.00000 | 61.61616 | −37.54401 |
| LPC 16:0/LacCer(d18:1/24:0) | 75.00000 | 60.82474 | −25.29458 |
| CE 15:0/Cer(d18:1/20:0) | 74.41860 | 60.57692 | −21.94830 |
| CE 16:0/Cer(d18:1/18:0) | 73.91304 | 61.06195 | −26.42362 |
| CE 16:1/Total LacCer | 73.91304 | 63.71681 | −33.50629 |
| CE 18:2/Cer(d18:1/20:0) | 73.91304 | 61.94690 | −19.85408 |
| CE 18:3/Cer(d18:1/24:0) | 73.91304 | 61.40351 | −28.00256 |
| CE 18:3/GlcCer(d18:1/20:0) | 73.91304 | 65.48673 | −38.77502 |
| CE 18:3/PC 16:0/16:0 | 73.91304 | 63.63636 | −31.16928 |
| CE 20:3/Cer(d18:1/24:1) | 73.91304 | 61.06195 | −30.78707 |
| CE 20:4/GlcCer(d18:1/20:0) | 73.91304 | 62.83186 | −30.95570 |
| CE 20:4/GlcCer(d18:1/24:1) | 73.91304 | 61.06195 | −28.82844 |

TABLE 9

Table of significant lipid to clinical ratios in LURIC study sorted by top
sensitivity and specificity. Table 9a shows significant lipids from all study subjects.
The significant lipids from subjects not undergoing statin treatment are listed in table
9b.

| Lipid name/Clinical measurement | Sensitivity | Specificity | Percentage change |
|---|---|---|---|
| 9a) Table of significant lipid to clinical ratios in LURIC study sorted by top sensitivity and specificity from all study subjects. | | | |
| Positive correlation | | | |
| LacCer(d18:1/20:0)/apolipoprotein A-I (mg/dL) | 75.47170 | 61.48148 | 43.04967 |
| Cer(d18:1/24:1)/total cholesterol (EDTA) (mg/dL) | 70.17544 | 60.73620 | 21.94547 |
| Cer(d18:1/24:1)/triglycerides (EDTA) (mg/dL) | 70.17544 | 60.12270 | 32.27486 |
| LacCer(d18:1/20:0)/HDL cholesterol (EDTA) (mg/dL) | 69.81132 | 62.22222 | 39.32664 |
| LacCer(d18:1/20:0)/apoA 1/apoB | 67.92453 | 61.48148 | 32.36387 |
| LacCer(d18:1/22:0)/HDL cholesterol (EDTA) (mg/dL) | 67.85714 | 60.00000 | 29.19905 |
| Cer(d18:1/16:0)/triglycerides (EDTA) (mg/dL) | 66.66667 | 61.34969 | 28.51323 |
| Cer(d18:1/22:0)/apolipoprotein B (mg/dL) | 66.66667 | 60.12270 | 14.20773 |
| Cer(d18:1/24:1)/apolipoprotein B (mg/dL) | 66.66667 | 62.57669 | 18.05222 |
| Total Cer/total cholesterol (EDTA) (mg/dL) | 66.66667 | 65.85366 | 15.12131 |
| LacCer(d18:1/20:0)/LDL-c/HDL-c | 66.03774 | 60.74074 | 23.54484 |
| LacCer(d18:1/20:0)/total cholesterol (EDTA) (mg/dL) | 66.03774 | 62.96296 | 41.46919 |
| LacCer(d18:1/20:0)/total-c/HDL-c | 66.03774 | 60.00000 | 33.48550 |

TABLE 9-continued

Table of significant lipid to clinical ratios in LURIC study sorted by top sensitivity and specificity. Table 9a shows significant lipids from all study subjects. The significant lipids from subjects not undergoing statin treatment are listed in table 9b.

| Lipid name/Clinical measurement | Sensitivity | Specificity | Percentage change |
|---|---|---|---|
| Cer(d18:1/18:0)/triglycerides (EDTA) (mg/dL) | 64.91228 | 60.73620 | 40.06643 |
| Cer(d18:1/22:0)/total cholesterol (EDTA) (mg/dL) | 64.91228 | 61.34969 | 17.20335 |
| Cer(d18:1/24:1)/total-c/HDL-c | 64.91228 | 61.34969 | 13.34657 |
| GlcCer(d18:1/24:0)/total cholesterol (EDTA) (mg/dL) | 64.91228 | 61.96319 | 17.04608 |
| LacCer(d18:1/18:0)/apolipoprotein A-I (mg/dL) | 64.91228 | 60.37736 | 41.61371 |
| LacCer(d18:1/18:0)/total cholesterol (EDTA) (mg/dL) | 64.91228 | 61.00629 | 38.87517 |
| Total LacCer/total cholesterol (EDTA) (mg/dL) | 64.91228 | 65.03067 | 23.69633 |
| LacCer(d18:1/22:0)/apoA1/apoB | 64.28571 | 62.85714 | 24.17423 |
| LacCer(d18:1/22:0)/apolipoprotein A-I (mg/dL) | 64.28571 | 62.85714 | 32.96039 |
| LacCer(d18:1/22:0)/total cholesterol (EDTA) (mg/dL) | 64.28571 | 60.00000 | 32.24669 |
| LacCer(d18:1/24:0)/apoA1/apoB | 64.28571 | 62.14286 | 15.23336 |
| LacCer(d18:1/20:0)/LDL cholesterol (EDTA) (mg/dL) | 64.15094 | 61.48148 | 31.95659 |
| LacCer(d18:1/20:0)/apolipoprotein B (mg/dL) | 64.15094 | 60.00000 | 37.03057 |
| PS O-18:2/16:0-alkenyl/triglycerides (EDTA) (mg/dL) | 63.63636 | 63.33333 | 99.88127 |
| Cer(d18:1/20:0)/apolipoprotein B (mg/dL) | 63.15789 | 60.12270 | 20.79615 |
| Cer(d18:1/20:0)/total cholesterol (EDTA) (mg/dL) | 63.15789 | 61.96319 | 25.23403 |
| Cer(d18:1/22:0)/LDL cholesterol (EDTA) (mg/dL) | 63.15789 | 60.12270 | 11.30545 |
| Cer(d18:1/24:1)/LDL cholesterol (EDTA) (mg/dL) | 63.15789 | 60.12270 | 14.20759 |
| PS O-16:0/18:2-alkenyl/triglycerides (EDTA) (mg/dL) | 63.15789 | 63.29114 | 97.78843 |
| PS O-16:1/18:2-alkyl/triglycerides (EDTA) (mg/dL) | 63.15789 | 63.29114 | 97.78843 |
| Total GlcCer/total cholesterol (EDTA) (mg/dL) | 63.15789 | 60.73620 | 17.56924 |
| Total LacCer/apolipoprotein A-I (mg/dL) | 63.15789 | 61.34969 | 25.87122 |
| Total LacCer/apolipoprotein B (mg/dL) | 63.15789 | 61.96319 | 20.63257 |
| LacCer(d18:1/24:1)/triglycerides (EDTA) (mg/dL) | 62.50000 | 62.14286 | 60.79934 |
| PS O-16:0/18:1-alkenyl (PS O-16:1/18:1-alkyl)/triglycerides (EDTA) (mg/dL) | 62.50000 | 61.39241 | 65.88734 |
| Cer(d18:1/20:0)/triglycerides (EDTA) (mg/dL) | 61.40351 | 60.73620 | 34.46408 |
| Cer(d18:1/22:0)/triglycerides (EDTA) (mg/dL) | 61.40351 | 63.19018 | 28.23304 |
| Cer(d18:1/24:1)/apolipoprotein A-I (mg/dL) | 61.40351 | 65.03067 | 27.12684 |
| LacCer(d18:1/16:0)/triglycerides (EDTA) (mg/dL) | 61.40351 | 64.41718 | 25.01312 |
| LacCer(d18:1/18:0)/HDL cholesterol (EDTA) (mg/dL) | 61.40351 | 60.37736 | 38.04132 |
| LacCer(d18:1/18:0)/LDL cholesterol (EDTA) (mg/dL) | 61.40351 | 64.15094 | 28.50180 |
| LacCer(d18:1/18:0)/apolipoprotein B (mg/dL) | 61.40351 | 61.00629 | 33.69302 |
| LacCer(d18:1/18:0)/triglycerides (EDTA) (mg/dL) | 61.40351 | 62.26415 | 52.60972 |
| Total Cer/apolipoprotein A-I (mg/dL) | 61.40351 | 63.41463 | 19.09944 |
| Total GlcCer/apolipoprotein B (mg/dL) | 61.40351 | 60.12270 | 14.92180 |
| Total LacCer/triglycerides (EDTA) (mg/dL) | 61.40351 | 62.57669 | 38.52220 |
| LacCer(d18:1/22:0)/apolipoprotein B (mg/dL) | 60.71429 | 65.00000 | 29.83861 |
| Negative correlation | | | |
| CE 18:3/total-c/HDL-c | 67.24138 | 62.89308 | −27.28733 |
| LPC 18:2/apolipoprotein B (mg/dL) | 65.45455 | 60.12658 | −16.19596 |
| Total PC/apolipoprotein B (mg/dL) | 64.91228 | 61.39241 | −12.91145 |
| Total PC/total cholesterol (EDTA) (mg/dL) | 64.91228 | 60.75949 | −10.60231 |
| CE 16:1/HDL cholesterol (EDTA) (mg/dL) | 63.79310 | 61.63522 | −22.01197 |
| CE 18:3/HDL cholesterol (EDTA) (mg/dL) | 63.79310 | 62.26415 | −24.04060 |
| CE 18:3/LDL cholesterol (EDTA) (mg/dL) | 63.79310 | 62.26415 | −27.21759 |
| LPC 18:2/LDL-c/HDL-c | 63.63636 | 61.39241 | −21.70580 |
| Total PC/total-c/HDL-c | 63.15789 | 60.12658 | −16.13350 |
| PC 16:0/20:3/HDL cholesterol (EDTA) (mg/dL) | 62.50000 | 62.65823 | −11.45558 |
| PC 16:0/20:3/apolipoprotein B (mg/dL) | 62.50000 | 60.12658 | −15.11848 |
| CE 16:1/apolipoprotein B (mg/dL) | 62.06897 | 62.26415 | −26.99397 |
| CE 16:1/total cholesterol (EDTA) (mg/dL) | 62.06897 | 60.37736 | −24.28770 |
| CE 18:3/LDL-c/HDL-c | 62.06897 | 62.89308 | −31.33346 |
| CE 18:3/apolipoprotein A-I (mg/dL) | 62.06897 | 60.37736 | −23.09816 |
| LPC 18:2/HDL cholesterol (EDTA) (mg/dL) | 61.81818 | 60.75949 | −16.07209 |
| LPC 18:2/apoA1/apoB | 61.81818 | 63.92405 | −19.23316 |
| PC 16:0/20:4/LDL cholesterol (EDTA) (mg/dL) | 61.40351 | 60.12658 | −15.98292 |
| PC 16:0/20:4/apolipoprotein A-I (mg/dL) | 61.40351 | 60.75949 | −12.23661 |
| PC 16:0/20:4/total cholesterol (EDTA) (mg/dL) | 61.40351 | 61.39241 | −13.37554 |
| Total PC/LDL-c/HDL-c | 61.40351 | 62.65823 | −21.24583 |
| PC 16:0/20:3/total-c/HDL-c | 60.71429 | 61.39241 | −19.07121 |
| PC 18:0/20:4/apoA1/apoB | 60.71429 | 62.02532 | −13.36540 |

TABLE 9-continued

Table of significant lipid to clinical ratios in LURIC study sorted by top sensitivity and specificity. Table 9a shows significant lipids from all study subjects. The significant lipids from subjects not undergoing statin treatment are listed in table 9b.

| Lipid name/Clinical measurement | Sensitivity | Specificity | Percentage change |
|---|---|---|---|
| CE 18:3/apoA1/apoB | 60.34483 | 60.37736 | −27.55825 |
| CE 18:3/apolipoprotein B (mg/dL) | 60.34483 | 61.00629 | −25.31907 |
| CE 20:5/HDL cholesterol (EDTA) (mg/dL) | 60.34483 | 60.37736 | −23.45029 |
| CE 20:5/LDL cholesterol (EDTA) (mg/dL) | 60.34483 | 60.37736 | −25.93288 |
| LPC 18:2/LDL cholesterol (EDTA) (mg/dL) | 60.00000 | 62.02532 | −17.26480 |
| LPC 18:2/total cholesterol (EDTA) (mg/dL) | 60.00000 | 62.65823 | −14.92954 |

9b) Table of significant lipid to clinical ratios in LURIC study sorted by top sensitivity and specificity from subjects not undergoing statin treatment.

Positive correlation

| Lipid name/Clinical measurement | Sensitivity | Specificity | Percentage change |
|---|---|---|---|
| Cer(d18:1/24:1)/apolipoprotein B (mg/dL) | 82.60870 | 62.06897 | 18.05222 |
| Cer(d18:1/24:1)/total cholesterol (EDTA) (mg/dL) | 80.43478 | 61.20690 | 21.94547 |
| LacCer(d18:1/20:0)/apolipoprotein A-I (mg/dL) | 77.27273 | 67.00000 | 43.04967 |
| Cer(d18:1/22:0)/LDL cholesterol (EDTA) (mg/dL) | 73.91304 | 60.34483 | 11.30545 |
| Total Cer/LDL cholesterol (EDTA) (mg/dL) | 73.91304 | 62.39316 | 8.25598 |
| Total Cer/total cholesterol (EDTA) (mg/dL) | 73.91304 | 70.08547 | 15.12131 |
| LacCer(d18:1/20:0)/HDL cholesterol (EDTA) (mg/dL) | 72.72727 | 61.00000 | 39.32664 |
| LacCer(d18:1/20:0)/apoA1/apoB | 72.72727 | 60.00000 | 32.36387 |
| Cer(d18:1/22:0)/total cholesterol (EDTA) (mg/dL) | 71.73913 | 61.20690 | 17.20335 |
| Cer(d18:1/24:1)/LDL cholesterol (EDTA) (mg/dL) | 71.73913 | 61.20690 | 14.20759 |
| Cer(d18:1/24:1)/total-c/HDL-c | 71.73913 | 60.34483 | 13.34657 |
| Total Cer/apolipoprotein A-I (mg/dL) | 71.73913 | 61.53846 | 19.09944 |
| Total Cer/apolipoprotein B (mg/dL) | 71.73913 | 61.53846 | 12.34421 |
| LacCer(d18:1/20:0)/LDL cholesterol (EDTA) (mg/dL) | 70.45455 | 61.00000 | 31.95659 |
| LacCer(d18:1/20:0)/LDL-c/HDL-c | 70.45455 | 61.00000 | 23.54484 |
| Cer(d18:1/20:0)/LDL cholesterol (EDTA) (mg/dL) | 69.56522 | 60.34483 | 18.51094 |
| Cer(d18:1/20:0)/apolipoprotein B (mg/dL) | 69.56522 | 68.10345 | 20.79615 |
| Cer(d18:1/20:0)/total cholesterol (EDTA) (mg/dL) | 69.56522 | 71.55172 | 25.23403 |
| Cer(d18:1/20:0)/total-c/HDL-c | 69.56522 | 60.34483 | 14.96816 |
| Cer(d18:1/22:0)/apolipoprotein B (mg/dL) | 69.56522 | 65.51724 | 14.20773 |
| Cer(d18:1/24:0)/total cholesterol (EDTA) (mg/dL) | 69.56522 | 60.68376 | 11.30123 |
| Cer(d18:1/24:1)/LDL-c/HDL-c | 69.56522 | 62.93103 | 5.34922 |
| Cer(d18:1/24:1)/apolipoprotein A-I (mg/dL) | 69.56522 | 60.34483 | 27.12684 |
| Cer(d18:1/24:1)/triglycerides (EDTA) (mg/dL) | 69.56522 | 63.79310 | 32.27486 |
| GlcCer(d18:1/24:1)/apolipoprotein B (mg/dL) | 69.56522 | 61.20690 | 17.03707 |
| Total DAG/apolipoprotein A-I (mg/dL) | 68.88889 | 60.19417 | 15.46034 |
| LacCer(d18:1/20:0)/total cholesterol (EDTA) (mg/dL) | 68.18182 | 61.00000 | 41.46919 |
| PC O-34:1/apolipoprotein B (mg/dL) | 68.18182 | 60.00000 | 22.73127 |
| Cer(d18:1/16:0)/LDL cholesterol (EDTA) (mg/dL) | 67.39130 | 62.06897 | 10.42412 |
| Cer(d18:1/18:0)/total-c/HDL-c | 67.39130 | 61.20690 | 21.75165 |
| Cer(d18:1/18:0)/triglycerides (EDTA) (mg/dL) | 67.39130 | 64.65517 | 40.06643 |
| Cer(d18:1/24:0)/LDL cholesterol (EDTA) (mg/dL) | 67.39130 | 62.39316 | 4.69599 |
| Cer(d18:1/24:0)/apolipoprotein A-I (mg/dL) | 67.39130 | 61.53846 | 14.67208 |
| GlcCer(d18:1/20:0)/total cholesterol (EDTA) (mg/dL) | 67.39130 | 60.34483 | 20.60005 |
| Total GlcCer/apolipoprotein B (mg/dL) | 67.39130 | 60.34483 | 14.92180 |
| Total LacCer/total cholesterol (EDTA) (mg/dL) | 67.39130 | 62.93103 | 23.69633 |
| LacCer(d18:1/22:0)/apoA1/apoB | 66.66667 | 61.76471 | 24.17423 |
| LacCer(d18:1/22:0)/apolipoprotein A-I (mg/dL) | 66.66667 | 60.78431 | 32.96039 |
| LacCer(d18:1/20:0)/apolipoprotein B (mg/dL) | 65.90909 | 61.00000 | 37.03057 |
| LacCer(d18:1/20:0)/total-c/HDL-c | 65.90909 | 62.00000 | 33.48550 |
| Cer(d18:1/16:0)/triglycerides (EDTA) (mg/dL) | 65.21739 | 62.06897 | 28.51323 |
| Cer(d18:1/22:0)/apolipoprotein A-I (mg/dL) | 65.21739 | 66.37931 | 21.04730 |
| Cer(d18:1/24:0)/apolipoprotein B (mg/dL) | 65.21739 | 62.39316 | 9.26738 |
| GlcCer(d18:1/20:0)/apolipoprotein B (mg/dL) | 65.21739 | 60.34483 | 17.00627 |
| GlcCer(d18:1/26:1)/apolipoprotein A-I (mg/dL) | 65.21739 | 61.60714 | 21.90520 |
| LacCer(d18:1/16:0)/triglycerides (EDTA) (mg/dL) | 65.21739 | 60.34483 | 25.01312 |
| LacCer(d18:1/18:0)/apolipoprotein B (mg/dL) | 65.21739 | 61.40351 | 33.69302 |
| LacCer(d18:1/18:0)/total cholesterol (EDTA) (mg/dL) | 65.21739 | 62.28070 | 38.87517 |
| PS O-16:0/18:2-alkenyl/triglycerides (EDTA) (mg/dL) | 65.21739 | 61.60714 | 97.78843 |
| PS O-16:1/18:2-alkyl/triglycerides (EDTA) (mg/dL) | 65.21739 | 61.60714 | 97.78843 |

Negative correlation

| Lipid name/Clinical measurement | Sensitivity | Specificity | Percentage change |
|---|---|---|---|
| CE 18:3/total-c/HDL-c | 68.08511 | 62.28070 | −27.28733 |
| CE 18:3/LDL-c/HDL-c | 63.82979 | 60.52632 | −31.33346 |
| CE 18:3/apoA1/apoB | 61.70213 | 64.03509 | −27.55825 |
| CE 20:5/triglycerides (EDTA) (mg/dL) | 61.70213 | 60.52632 | −15.26342 |
| PC O-38:6/apolipoprotein A-I (mg/dL) | 60.86957 | 62.03704 | −3.87776 |
| Total LPC/apoA1/apoB | 60.86957 | 60.71429 | −14.81039 |
| Total PC/apolipoprotein A-I (mg/dL) | 60.86957 | 62.50000 | −8.50761 |
| PC 18:0/20:4/apoA1/apoB | 60.00000 | 64.28571 | −13.36540 |

The preferred lipid molecules of the invention were selected as follows: a) it was likely to be biologically meaningful, b) it preferably belongs to a family of lipids that are behaving similarly, c) it is expressed in meaningful & measurable concentrations, d) it has very significant p-value or good AUC-value (>0.65) and for most also the %-change is substantial (>20%), and c) it appeared significant in different tests. About 15 lipids or lipid ratios, each with either a positive or negative CVD correlation, were selected based on the highest p-values and best sensitivity and specificity subjectively ensuring the balanced representation of all lipid classes. Sensitivity and specificity thresholds were annotated in cases where the threshold of 60 and 70 were reached, respectively. The preferred embodiment lipids, lipid-lipid ratios and lipid-clinical ratios are presented in tables 10-13.

TABLE 10

The preferred embodiment lipids selected from significant lipids detected from LURIC sample set.

| Lipid name | p-value | Percentage change | Sensitivity | Specificity |
| --- | --- | --- | --- | --- |
| Positive correlation | | | | |
| Cer(d18:1/20:0) | 0.00004 | 28.00357 | | |
| LacCer(d18:1/20:0) | 0.00010 | 32.91154 | 70.45455 | 60.00000 |
| Cer(d18:1/24:1) | 0.00039 | 23.37606 | 69.56522 | 60.34483 |
| LacCer(d18:1/24:1) | 0.00199 | 29.83279 | | |
| PS O-18:2/16:0-alkenyl | 0.00432 | 33.81177 | | |
| PS O-16:1/18:2-alkyl | 0.00590 | 32.17190 | | |
| Total Cer | 0.00932 | 15.44601 | | |
| Total LacCer | 0.01105 | 16.00541 | | |
| GlcCer(d18:1/24:1) | | 12.75066 | 60.86957 | 62.06897 |
| LacCer(d18:1/22:0) | 0.00046 | 22.75541 | | |
| Cer(d18:1/18:0) | 0.00009 | 34.32550 | | |
| Negative correlation | | | | |
| Total PC | 0.00921 | −12.44220 | | |
| PC 16:0/20:4 | 0.02256 | −14.96966 | | |
| Cer(d18:0/24:0) | 0.03376 | −21.87004 | | |
| Total LPC | 0.03443 | −12.91576 | | |
| CE 14:0 | 0.01090 | −21.01258 | | |
| CE 20:3 | 0.02157 | −16.03606 | | |
| CE 17:1 | 0.02204 | −15.93952 | | |
| PC 16:0/20:3 | | −18.78110 | 64.44444 | 60.71429 |
| LPC 18:1 | | −14.45827 | 63.04348 | 60.71429 |
| PC 18:0/20:3 | 0.00726 | −17.20664 | | |
| PC 18:0/18:1 | 0.00765 | −18.18002 | | |
| Cer(d18:0/22:0) | 0.01158 | −22.37263 | | |

TABLE 11

Preferred embodiments from significant lipid to lipid ratios detected from LURIC sample set.

| Lipid name/Lipid name | p-value | Percentage change | Sensitivity | Specificity |
| --- | --- | --- | --- | --- |
| Positive correlation | | | | |
| GlcCer(d18:1/26:1)/Total CE | 0.000000 | 35.356592 | | |
| Cer(d18:1/24:1)/Total PC | 0.000000 | 43.040800 | | |
| Cer(d18:1/24:1)/PC 16:0/20:4 | 0.000000 | 59.876132 | | |
| Cer(d18:1/20:0)/PC 16:0/20:4 | 0.000000 | 64.045788 | | |
| LacCer(d18:1/20:0)/PC 16:0/20:3 | 0.000008 | 56.972652 | 80.39216 | 65.11628 |
| Total Cer/Total PC | 0.000011 | 29.949121 | | |
| Total LacCer/Total PC | 0.000012 | 37.815865 | | |
| LacCer(d18:1/20:0)/PC 18:1/18:2 | 0.000013 | 48.432788 | | |
| PS O-16:0/18:2-alkenyl/Total PS O | | 26.42621 | 97.82609 | 62.50000 |
| Cer(d18:1/18:0)/PC 16:0/20:4 | | 73.07370 | 80.00000 | 62.16216 |
| LacCer(d18:1/20:0)/Total LPC | | 53.68111 | 78.84615 | 61.24031 |
| LacCer(d18:1/20:0)/PC 16:0/20:4 | | 82.44735 | 79.06977 | 68.42105 |
| Negative correlation | | | | |
| Cer(d18:0/24:0)/Cer(d18:1/24:1) | 0.000003 | −36.760563 | | |
| Cer(d18:0/22:0)/Cer(d18:1/24:1) | 0.000011 | −34.086320 | | |
| DAG 16:0/18:1/Total DAG | | −17.30528 | 88.88889 | 61.16505 |
| Cer(d18:0/24:0)/Cer(d18:1/22:0) | | −32.40867 | 75.43860 | 66.25767 |
| Cer(d18:0/24:0)/Total CE | 0.0000000 | −18.9531828 | | |
| Cer(d18:0/24:0)/Cer(d18:1/24:1) | 0.000003 | −36.760563 | | |
| Cer(d18:0/24:0)/Total Cer | 0.0000049 | −31.4531758 | | |
| Cer(d18:0/24:0)/Cer(d18:1/18:0) | 0.0000052 | −40.2960344 | | |
| Cer(d18:0/24:0)/PS O-16:0/18:2-alkenyl | 0.0000059 | −40.8329837 | | |
| Cer(d18:0/24:0)/LacCer(d18:1/24:0) | 0.0000067 | −37.0287234 | | |
| Cer(d18:0/22:0)/Cer(d18:1/18:0) | 0.0000071 | −36.5340374 | | |
| Cer(d18:0/24:0)/Cer(d18: 1/22:0) | 0.0000105 | −32.4086711 | | |
| Cer(d18:0/22:0)/Cer(d18: 1/20:0) | 0.0000165 | −31.5266149 | | |
| Cer(d18:0/22:0)/PS O-16:0/18:2-alkenyl | 0.000045 | −37.930990 | | |
| Cer(d18:0/22:0)/PS O-16:1/18:2-alkyl | 0.000045 | −37.930990 | | |
| GlcCer(d18:1/26:0)/LacCer(d18:1/20:0) | | −26.83109 | 80.48780 | 64.77273 |
| Total LPC/Total LacCer | 0.0000469 | −26.08820 | | |
| GlcCer(d18:1/26:0)/LacCer(d18:1/22:0) | | −21.27116 | 78.04878 | 61.79775 |

TABLE 12

Preferred embodiments from significant lipid to clinical ratios from LURIC sample set.

| Lipid name/Clinical measurement | p-value | Percentage change | Sensitivity | Specificity |
|---|---|---|---|---|
| Positive correlation | | | | |
| Cer(d18:1/20:0)/apolipoprotein A-I (mg/dL) | 0.00000 | 43.22923 | | |
| Cer(d18:1/24:1)/apolipoprotein A-I (mg/dL) | 0.00000 | 36.15491 | 69.56522 | 60.34483 |
| LacCer(d18:1/20:0)/apolipoprotein A-I (mg/dL) | 0.00001 | 47.52465 | 77.27273 | 67.00000 |
| Total Cer/apolipoprotein A-I (mg/dL) | 0.00016 | 25.36811 | | |
| Total LacCer/apolipoprotein A-I (mg/dL) | 0.00031 | 28.05057 | 71.73913 | 61.53846 |
| Cer(d18:1/18:0)/apolipoprotein A-I (mg/dL) | 0.00001 | 49.43693 | | |
| LacCer(d18:1/22:0)/apolipoprotein A-I (mg/dL) | 0.00001 | 35.92744 | | |
| LacCer(d18:1/20:0)/HDL cholesterol (EDTA) (mg/dL) | | 39.32664 | 72.72727 | 61.00000 |
| Cer(d18:1/24:1)/apolipoprotein B (mg/dL) | | 18.05222 | 82.60870 | 62.06897 |
| Negative correlation | | | | |
| Cer(d18:0/24:0)/apolipoprotein B (mg/dL) | 0.03428 | −21.10483 | | |
| Cer(d18:0/24:0)/total cholesterol (EDTA) (mg/dL) | 0.04309 | −19.71324 | | |
| Cer(d18:0/24:0)/apolipoprotein B (mg/dL) | 0.00181 | −26.25271 | | |
| PC 16:0/20:4/apolipoprotein B (mg/dL) | 0.00576 | −15.39247 | | |
| Cer(d18:0/24:0)/apolipoprotein A-I (mg/dL) | 0.01052 | −22.39254 | | |

TABLE 13

Top candidates from each category, if available, are listed. The best candidates were selected based on following criteria: t-test p-value ≤ 0.05 and sensitivity ≥ 60% and specificity ≥ 60%.

| Measurement name | p-value | Percentage change |
|---|---|---|
| Positive correlation | | |
| Cer(d18:1/20:0) | 0.00004 | 28.00357 |
| LacCer(d18:1/20:0) | 0.00010 | 32.91154 |
| Cer(d18:1/24:1) | 0.00039 | 23.37606 |
| LacCer(d18:1/24:1) | 0.00199 | 29.83279 |
| LacCer(d18:1/22:0) | 0.00046 | 22.75541 |
| Cer(d18:1/18:0) | 0.00009 | 34.32550 |
| Cer(d18:1/24:1)/PC 16:0/20:4 | 0.000000 | 59.876132 |
| LacCer(d18:1/20:0)/PC 16:0/20:3 | 0.000008 | 56.972652 |
| PS O-16:0/18:2-alkenyl/Total PS O | | 26.42621 |
| Cer(d18:1/18:0)/PC 16:0/20:4 | 0.000000 | 73.073704 |
| Cer(d18:1/20:0)/apolipoprotein A-I (mg/dL) | 0.00000 | 43.22923 |
| Cer(d18:1/24:1)/apolipoprotein A-I (mg/dL) | 0.00000 | 36.15491 |
| LacCer(d18:1/20:0)/apolipoprotein A-I (mg/dL) | 0.00001 | 47.52465 |
| Total LacCer/apolipoprotein A-I (mg/dL) | 0.00031 | 28.05057 |
| LacCer(d18:1/20:0)/HDL cholesterol (EDTA) (mg/dL) | | 39.32664 |
| Cer(d18:1/18:0)/apolipoprotein A-I (mg/dL) | 0.00001 | 49.43693 |
| Negative correlation | | |
| PC 16:0/20:4 | 0.02256 | −14.96966 |
| Cer(d18:0/24:0) | 0.03376 | −21.87004 |
| GlcCer(d18:1/26:0)/LacCer(d18:1/20:0) | | −26.83109 |
| DAG 16:0/18:1/Total DAG | | −17.30528 |
| Cer(d18:0/24:0)/Total Cer | | −31.45318 |
| Total LPC/Total LacCer | | −26.08820 |
| GlcCer(d18:1/26:0)/LacCer(d18:1/22:0) | | −21.27116 |
| Cer(d18:0/24:0)/Cer(d18:1/24:1) | 0.0000004 | −36.1288066 |
| Cer(d18:0/24:0)/Cer(d18:1/18:0) | 0.0000052 | −40.2960344 |
| Cer(d18:0/24:0)/PS O-16:0/18:2-alkenyl | 0.0000059 | −40.8329837 |
| Cer(d18:0/24:0)/Cer(d18:1/22:0) | 0.0000105 | −32.4086711 |
| Cer(d18:0/22:0)/PS O-16:0/18:2-alkenyl | 0.000045 | −37.930990 |
| Cer(d18:0/22:0)/PS O-16:1/18:2-alkyl | 0.000045 | −37.930990 |
| Cer(d18:0/24:0)/LacCer(d18:1/24:0) | 0.0000067 | −37.0287234 |

Lipidomic analysis proved to be efficient in identifying novel plasma biomarkers for CVD complications.

Molecular lipid to molecular lipid ratio could be an important indicator of cellular lipid metabolism including e.g., enzyme activities in the lipid metabolism pathways. Thus, these ratios may provide more information as the absolute plasma concentrations of the molecular lipids alone. As the absolute molecular lipid plasma concentration differences in general between healthy individuals and atherosclerotic patients seem to be between 30-70%, it might be reasonable to calculate and use different ratios instead of absolute concentrations only. As lipoprotein particles (e.g. LDL, HDL, and VLDL) are serving as carriers for most of the lipids in the blood stream it is appropriate to relate molecular lipid concentrations to lipoprotein data. Thus, the molecular lipid to HDL-cholesterol, LDL-cholesterol, apolipoprotein A-I and apolipoprotein B ratios were calculated. In fact, a number of ratios between the concentrations of different molecular lipids outperformed absolute plasma concentrations as disease biomarkers in CVD patients.

As the detected lipids are carried in the lipoprotein particles (LDL, VLDL and HDL) it is obvious that the corresponding lipoprotein fraction concentrations will even improve the prediction potential of molecular lipids from the results of the present study in total serum/plasma samples.

The lipid lowering drug efficiency measurements have so far been based on LDL-C and HDL-C assays. As the inventors have herein observed more potential biomarkers that predict the development of high-risk CVD complications better than these classical analyses, future drug efficiency profiling should be based on new sensitive and specific biomarkers that are more directly related to the risk of severe CVD-related complications rather than to LDL-C.

Those skilled in the art will recognize, or be able to ascertain using no more than routine experimentation, numerous equivalents to the specific embodiments described herein both in the Examples in the body of the entire patent description. Such equivalents are considered to be within the scope of this invention and are covered by the following claims.

The invention claimed is:

1. A method for determining one or more lipid concentration(s), lipid-lipid concentration ratio(s) and/or lipid-clinical concentration ratio(s) in a sample by mass spectrometry (MS), comprising:
  (a) extracting lipids from the sample; and
  (b) separating the lipids by liquid chromatography (LC) prior to the MS determination; and
  (c) determining the one or more lipid concentration(s), lipid-lipid concentration ratio(s) and/or lipid-clinical concentration ratio(s) in the sample by MS,
  wherein the one or more lipid(s) is (are) selected from:
  Ceramide (Cer)(d18:1/16:0), Cer(d18:1/18:0), Cer(d18:1/22:0), Cer(d18:1/24:1), Cer(d18:1/26:1), Lactosylceramide (LacCer)(d18:1/18:0), LacCer (d18:1/20:0), LacCer(d18:1/22:0), LacCer(d18:1/24:0), LacCer(d18:1/24:1), Galactosyl- and glucosylceramide (GlcCer) (d18:1/18:0), GlcCer(d18:1/20:0), GlcCer(d18:1/24:1), GlcCer(d18:1/26:1), ether-linked Phosphatidylserine (PS O)-18:2/16:0-alkenyl, PS O-16:0/18:2-alkenyl, PS O-16:1/18:2-alkyl, PS O-18:0/18:2-alkenyl (PS O-18:1/18:2-alkyl), ether-linked phosphatidylcholine (PC-O)-32:0 (KDdiA-PC), phosphatidylcholine (PC) 18:0/20:4, PC 16:0/20:4, PC 18:0/20:3, PC 16:0/20:3, PC 16:0/22:6, PC 16:0/18:2, PC 18:0/18:1, PC 18:1/18:2, LPC 18:1, PC O-40:3, Sphingomyelin (SM) (d18:1/14:0) (d18:1/13:1-OH), SM (d18:1/23:0) (d18:1/22:1-OH), SM (d18:1/24:0) (d18:1/23:1-OH), Cer(d18:0/22:0), Cer(d18:0/24:0) and PC 16:0/16:0;
  wherein the one or more lipid-lipid concentration ratio(s) is (are) selected from:
  Cer(d18:1/18:0)/PC 16:0/18:1, Cer(d18:1/20:0)/PC 16:0/18:1, Cer(d18:1/24:1)/PC 16:0/18:1, Cer(d18:1/24:1)/PC 16:0/18:2, Cer(d18:1/18:0)/PC 18:0/18:1, Cer(d18:1/20:0)/PC 18:0/18:1, Cer(d18:1/24:1)/PC 18:0/18:1, Cer(d18:1/24:1)/PC 18:0/18:2, Cer(d18:1/18:0)/PC 18:1/18:1, Cer(d18:1/20:0)/PC 18:1/18:1, Cer(d18:1/24:1)/PC 18:1/18:1, Cer(d18:1/24:1)/PC 18:1/18:2, Cer(d18:1/18:0)/PC 16:0/20:3, Cer(d18:1/20:0)/PC 16:0/20:3, Cer(d18:1/22:0)/PC 16:0/20:3, Cer(d18:1/24:1)/PC 16:0/20:3, Cer(d18:1/24:1)/PC 18:0/20:3, Cer(d18:1/18:0)/PC 16:0/20:4, Cer(d18:1/20:0)/PC 16:0/20:4, Cer(d18:1/22:0)/PC 16:0/20:4, Cer(d18:1/24:1)/PC 16:0/20:4, Cer(d18:1/18:0)/PC 18:0/20:4, Cer(d18:1/20:0)/PC 18:0/20:4, Cer(d18:1/22:0)/PC 18:0/20:4, Cer(d18:1/24:1)/PC 18:0/20:4, Cer(d18:1/24:1)/PC O-40:3, Cer(d18:1/26:0)/PC O-40:0, PC 16:0/16:0/PC 16:0/20:4, PC O-18:0/18:2-alkyl/PC O-36:5, PC O-32:0 (KDdiA-PC)/PC O-38:5, Cer(d18:1/18:0)/Lysophosphatidylcholine (LPC) 16:0, Cer(d18:1/16:0)/LPC 18:1, Cer(d18:1/18:0)/LPC 18:1, Cer(d18:1/24:1)/LPC 18:1, Cer(d18:1/22:0)/LPC 18:2, Cer(d18:1/24:1)/LPC 18:2, LacCer(d18:1/18:0)/PC 16:0/18:1, LacCer(d18:1/20:0)/PC 16:0/18:1, LacCer(d18:1/18:0)/PC 18:0/18:1, LacCer(d18:1/20:0)/PC 18:0/18:1, LacCer(d18:1/18:0)/PC 18:1/18:1, LacCer(d18:1/20:0)/PC 18:1/18:1, LacCer(d18:1/18:0)/PC 18:1/18:2, LacCer(d18:1/20:0)/PC 18:1/18:2, LacCer(d18:1/20:0)/PC 18:2/18:2, LacCer(d18:1/18:0)/PC 16:0/20:3, LacCer(d18:1/20:0)/PC 16:0/20:3, LacCer(d18:1/22:0)/PC 16:0/20:3, LacCer(d18:1/24:0)/PC 16:0/20:3, LacCer(d18:1/18:0)/PC 18:0/20:3, LacCer(d18:1/20:0)/PC 18:0/20:3, LacCer(d18:1/22:0)/PC 18:0/20:3, LacCer(d18:1/20:0)/PC 16:0/20:4, LacCer(d18:1/22:0)/PC 16:0/20:4, LacCer(d18:1/20:0)/PC 18:0/20:4, GlcCer(d18:1/20:0)/PC 16:0/20:4, Cer(d18:1/18:0)/SM (d18:1/17:2-OH), Cer(d18:1/18:0)/SM (d18:1/18:1), Cer(d18:1/18:0)/SM (d18:1/14:0) (d18:1/13:1-OH), Cer(d18:1/20:0)/SM (d18:1/14:0) (d18:1/13:1-OH), Cer(d18:1/24:1)/SM (d18:1/17:1-OH), Cer(d18:1/24:1)/SM (d18:1/18:0), Cer(d18:1/24:1)/SM (d18:1/23:0) (d18:1/22:1-OH), Cer(d18:1/24:1)/SM (d18:1/24:0) (d18:1/23:1-OH), LacCer(d18:1/20:0)/SM (d18:1/17:1-OH), LacCer(d18:1/20:0)/SM (d18:1/18:0) and LacCer(d18:1/22:0)/SM (d18:1/14:0) (d18:1/13:1-OH) Cer(d18:1/24:1)/Total PC, Cer(d18:1/18:0)/Total LPC, Cer(d18:1/20:0)/Total LPC, Cer(d18:1/24:1)/Total LPC, Cer(d18:1/18:0)/Total Cholesterol Ester (CE), Cer(d18:1/24:1)/Total CE, Total Cer/Total PC, Total LacCer/Total PC, LacCer(d18:1/22:0)/Total PC, LacCer(d18:1/22:0)/Total LPC, LacCer(d18:1/24:1)/Total PC, LacCer(d18:1/24:1)/Total LPC, LacCer(d18:1/24:1)/Total PC O, SM (d18:1/17:0) (d18:1/16:1-OH)/Total PC O, Cer(d18:0/22:0)/Cer(d18:1/18:0), Cer(d18:0/22:0)/Cer(d18:1/20:0), Cer(d18:0/22:0)/Cer(d18:1/22:0), Cer(d18:0/22:0)/Cer(d18:1/24:1), Cer(d18:0/24:0)/Cer(d18:1/16:0), Cer(d18:0/24:0)/Cer(d18:1/18:0), Cer(d18:0/24:0)/Cer(d18:1/20:0), Cer(d18:0/24:0)/Cer(d18:1/22:0), Cer(d18:0/24:0)/Cer(d18:1/24:1), PC 18:1/18:2/PS O-16:0/18:2-alkenyl, PC 18:1/18:2/PS O-16:1/18:2-alkyl, PC 16:0/20:3/PS O-16:0/18:2-alkenyl, PC 16:0/20:3/PS O-16:1/18:2-alkyl, PC 18:0/20:3/PS O-16:0/18:2-alkenyl, PC 18:0/20:3/PS O-16:1/18:2-alkyl, PC 18:0/20:3/PS O-18:2/16:0-alkenyl, PC 16:0/20:4/PS O-16:0/18:2-alkenyl, PC 16:0/20:4/PS O-16:1/18:2-alkyl, PC 18:0/20:4/PS O-16:0/18:2-alkenyl, PC 18:0/20:4/PS O-16:1/18:2-alkyl, PC O-40:3/PS O-18:2/16:0-alkenyl, LPC 18:2/PS O-16:0/18:2-alkenyl, LPC 18:2/PS O-16:1/18:2-alkyl, LPC 16:0/LacCer(d18:1/20:0), LPC 16:0/LacCer(d18:1/22:0), LPC 16:0/LacCer(d18:1/24:0), LPC 16:0/LacCer(d18:1/24:1), LPC 18:1/LacCer(d18:1/20:0), LPC 18:2/LacCer(d18:1/20:0), (d18:1/24:0), Cer(d18:0/24:0)/LacCer(d18:1/24:0), Cer(d18:

0/24:0)/SM (d18:1/17:0) (d18:1/16:1-OH), Cer(d18:0/ 22:0)/PS O-16:0/18:2-alkenyl, Cer(d18:0/22:0)/PS O-16:1/18:2-alkyl, Cer(d18:0/24:0)/PS O-16:0/18:2-alkenyl, Cer(d18:0/24:0)/Total Cer, Cer(d18:0/22:0)/Total CE, Cer(d18:0/24:0)/Total CE, Cer(d18:0/24:1)/Total CE, PC 16:0/20:4/Total diacylglycerol (DAG) and LPC 16:0/Total LacCer; and/or wherein the one or more lipid-clinical concentration ratio(s) is (are) selected from:

Cer(d18:1/16:0)/apolipoprotein A-I, Cer(d18:1/16:0)/Low Density Lipoprotein (LDL) cholesterol, Cer(d18:1/16:0)/triglycerides, Cer(d18:1/16:0)/total cholesterol, Cer(d18:1/18:0)/apolipoprotein A-I, Cer(d18:1/18:0)/apolipoprotein B, Cer(d18:1/18:0)/HDL cholesterol, Cer(d18:1/18:0)/total-c/HDL-c, Cer(d18:1/18:0)/total cholesterol, Cer(d18:1/18:0)/triglycerides, Cer(d18:1/18:0)/LDL cholesterol, Cer(d18:1/20:0)/apolipoprotein A-I, Cer(d18:1/20:0)/apolipoprotein B, Cer(d18:1/20:0)/High Density Lipoprotein (HDL) cholesterol, Cer(d18:1/20:0)/total cholesterol, Cer(d18:1/20:0)/triglycerides, Cer(d18:1/20:0)/total-cholesterol (total-c)/High Density Lipoprotein-c (HDL-c), Cer(d18:1/20:0)/LDL cholesterol, Cer(d18:1/22:0)/apolipoprotein A-I, Cer(d18:1/22:0)/apolipoprotein B, Cer(d18:1/22:0)/LDL cholesterol, Cer(d18:1/22:0)/triglycerides, Cer(d18:1/22:0)/total cholesterol, Cer(d18:1/24:0)/apolipoprotein A-I, Cer(d18:1/24:0)/apolipoprotein B, Cer(d18:1/24:0)/LDL cholesterol, Cer(d18:1/24:0)/total cholesterol, Cer(d18:1/24:1)/apolipoprotein A-I, Cer(d18:1/24:1)/apolipoprotein B, Cer(d18:1/24:1)/HDL cholesterol, Cer(d18:1/24:1)/Low Density Lipoprotein-c (LDL-c)/HDL-c, Cer(d18:1/24:1)/total-c/HDL-c, Cer(d18:1/24:1)/LDL cholesterol, Cer(d18:1/24:1)/total cholesterol, Cer(d18:1/24:1)/triglycerides, Total Cer/apolipoprotein A-I, Total Cer/apolipoprotein B, Total Cer/LDL cholesterol, Total Cer/total cholesterol, Total Cer/triglycerides, PC O-32:0 (KDdiA-PC)/apolipoprotein A-I, PC O-32:0 (KDdiA-PC)/triglycerides, PC O-34:1/apolipoprotein B, PC O-34:1/triglycerides, LacCer(d18:1/18:0)/apolipoprotein A-I, LacCer(d18:1/18:0)/apolipoprotein B, LacCer(d18:1/18:0)/total cholesterol, LacCer(d18:1/18:0)/HDL cholesterol, LacCer(d18:1/18:0)/LDL cholesterol, LacCer(d18:1/18:0)/total-c/HDL-c, LacCer(d18:1/18:0)/triglycerides, LacCer(d18:1/20:0)/apolipoprotein A-I, LacCer(d18:1/20:0)/apolipoprotein B, LacCer(d18:1/20:0)/total cholesterol, LacCer(d18:1/20:0)/HDL cholesterol, LacCer(d18:1/20:0)/LDL cholesterol, LacCer(d18:1/20:0)/total-c/HDL-c, LacCer(d18:1/20:0)/LDL-c/HDL-c, LacCer(d18:1/20:0)/apoA1/apoB, LacCer(d18:1/20:0)/triglycerides, LacCer(d18:1/22:0)/apolipoprotein A-I, LacCer(d18:1/22:0)/apolipoprotein B, LacCer(d18:1/22:0)/total cholesterol, LacCer(d18:1/22:0)/HDL cholesterol, LacCer(d18:1/22:0)/LDL cholesterol, LacCer(d18:1/22:0)/total-c/HDL-c, LacCer(d18:1/22:0)/apoA1/apoB, LacCer(d18:1/22:0)/triglycerides, LacCer(d18:1/24:0)/apoA1/apoB, LacCer(d18:1/24:1)/apolipoprotein A-I, LacCer(d18:1/24:1)/apolipoprotein B, LacCer(d18:1/24:1)/total cholesterol, LacCer(d18:1/24:1)/triglycerides, Cer(d18:0/22:0)/apolipoprotein B, Cer(d18:0/22:0)/LDL-c/HDL-c, Cer(d18:0/22:0)/total-c/HDL-c, Cer(d18:0/24:0)/apolipoprotein A-I, Cer(d18:0/24:0)/apolipoprotein B, Cer(d18:0/24:0)/total cholesterol, Cer(d18:0/24:0)/HDL cholesterol, Cer(d18:0/24:0)/LDL-c/HDL-c, Cer(d18:0/24:0)/total-c/HDL-c, Cer(d18:0/24:0)/LDL cholesterol, PC 18:0/18:1/LDL-c/HDL-c, PC 16:0/20:3/apolipoprotein B, PC 16:0/20:3/HDL cholesterol, PC 16:0/20:3/total-c/HDL-c, PC 16:0/20:3/LDL-c/HDL-c, PC 18:0/20:3/total-c/HDL-c, PC 18:0/20:3/LDL-c/HDL-c, PC 16:0/20:4/apolipoprotein A-I, PC 16:0/20:4/apolipoprotein B, PC 16:0/20:4/total cholesterol, PC 16:0/20:4/LDL cholesterol, PC 16:0/20:4/total-c/HDL-c, PC 16:0/20:4/LDL-c/HDL-c, PC 18:0/20:4/apoA1/apoB, PC O-38:6/apolipoprotein A-I, LPC 18:2/apolipoprotein B, LPC 18:2/total cholesterol, LPC 18:2/HDL cholesterol, LPC 18:2/LDL cholesterol, LPC 18:2/LDL-c/HDL-c and LPC 18:2/apoA1/apoB, wherein the sample is from a subject suspected to be at risk for one or more CVD complications, wherein the one or more CVD complications comprise myocardial infarction (MI) and/or death.

2. The method of claim 1, wherein (a) the one or more lipid(s) is (are) selected from:

Cer(d18:1/16:0), Cer(d18:1/18:0), Cer(d18:1/20:0), Cer(d18:1/22:0), Cer(d18:1/24:1), Cer(d18:1/26:1), PC 18:0/20:4, PC 16:0/20:4, PC 18:0/20:3, PC 16:0/20:3, PC 16:0/22:6, PC 16:0/18:2, PC 18:0/18:1, PC 18:1/18:2, LPC 18:1, PC O-40:3 and PC 16:0/16:0;

(b) the one or more lipid-lipid concentration ratio(s) is (are) selected from:

Cer(d18:1/18:0)/PC 16:0/18:1, Cer(d18:1/24:1)/PC 16:0/18:1, Cer(d18:1/24:1)/PC 16:0/18:2, Cer(d18:1/18:0)/PC 18:0/18:1, Cer(d18:1/24:1)/PC 18:0/18:1, Cer(d18:1/24:1)/PC 18:0/18:2, Cer(d18:1/18:0)/PC 18:1/18:1, Cer(d18:1/24:1)/PC 18:1/18:1, Cer(d18:1/24:1)/PC 18:1/18:2, Cer(d18:1/18:0)/PC 16:0/20:3, Cer(d18:1/24:1)/PC 16:0/20:3, Cer(d18:1/24:1)/PC 18:0/20:3, Cer(d18:1/18:0)/PC 16:0/20:4, Cer(d18:1/24:1)/PC 16:0/20:4, Cer(d18:1/18:0)/PC 18:0/20:4, Cer(d18:1/24:1)/PC 18:0/20:4, Cer(d18:1/24:1)/PC O-40:3, PC 16:0/16:0/PC 16:0/20:4, Cer(d18:0/22:0)/Cer(d18:1/18:0), Cer(d18:0/22:0)/Cer(d18:1/20:0), Cer(d18:0/22:0)/Cer(d18:1/22:0), Cer(d18:0/22:0)/Cer(d18:1/24:1), Cer(d18:0/24:0)/Cer(d18:1/16:0), Cer(d18:0/24:0)/Cer(d18:1/18:0), Cer(d18:0/24:0)/Cer(d18:1/20:0), Cer(d18:0/24:0)/Cer(d18:1/22:0), Cer(d18:0/24:0)/Cer(d18:1/24:1), PC 18:1/18:2/PS O-16:0/18:2-alkenyl, PC 18:1/18:2/PS O-16:1/18:2-alkyl, PC 16:0/20:3/PS O-16:0/18:2-alkenyl, PC 16:0/20:3/PS O-16:1/18:2-alkyl, PC 18:0/20:3/PS O-16:0/18:2-alkenyl, PC 18:0/20:3/PS O-16:1/18:2-alkyl, PC 18:0/20:3/PS O-18:2/16:0-alkenyl, PC 16:0/20:4/PS O-16:0/18:2-alkenyl, PC 16:0/20:4/PS O-16:1/18:2-alkyl, PC 18:0/20:4/PS O-16:0/18:2-alkenyl, PC 18:0/20:4/PS O-16:1/18:2-alkyl and PC O-40:3/PS O-18:2/16:0-alkenyl; and/or (c) the one or more lipid-clinical concentration ratio(s) is (are) selected from:

Cer(d18:1/16:0)/apolipoprotein A-I, Cer(d18:1/16:0)/LDL cholesterol, Cer(d18:1/16:0)/triglycerides, Cer(d18:1/16:0)/total cholesterol, Cer(d18:1/18:0)/apolipoprotein A-I, Cer(d18:1/18:0)/apolipoprotein B, Cer(d18:1/18:0)/HDL cholesterol, Cer(d18:1/18:0)/total-c/HDL-c, Cer(d18:1/18:0)/total cholesterol, Cer(d18:1/18:0)/triglycerides, Cer(d18:1/18:0)/LDL cholesterol, Cer(d18:1/24:1)/apolipoprotein A-I, Cer(d18:1/24:1)/apolipoprotein B, Cer(d18:1/24:1)/HDL cholesterol, Cer(d18:1/24:1)/LDL-c/HDL-c, Cer(d18:1/24:1)/total-c/HDL-c, Cer(d18:1/24:1)/LDL cholesterol, Cer(d18:1/24:1)/total cholesterol, Cer(d18:1/24:1)/triglycerides, PC 18:0/18:1/LDL-c/HDL-c, PC 16:0/20:3/apolipoprotein B, PC 16:0/20:3/HDL cholesterol, PC 16:0/20:3/total-c/HDL-c, PC 16:0/20:3/LDL-c/HDL-c, PC 18:0/20:3/total-c/HDL-c, PC 18:0/20:3/LDL-c/HDL-c, PC 16:0/20:4/apolipoprotein A-I, PC 16:0/20:4/apolipoprotein B, PC 16:0/20:4/total cholesterol, PC 16:0/20:4/LDL cholesterol, PC 16:0/20:4/total-c/HDL-c, PC 16:0/20:4/LDL-c/HDL-c, PC 18:0/20:4/apoA1/apoB and PC O-38:6/apolipoprotein A-I.

3. The method of claim 1, wherein the one or more lipids comprises at least 2, at least 3, at least 4, at least 5, at least 6, at least 7, or at least 8 lipids, wherein the one or more lipid-lipid concentration ratios comprises at least 2, at least 3, at least 4, at least 5, at least 6, at least 7, or at least 8 lipid-lipid concentration ratios, and/or wherein the one or more lipid-clinical concentration ratios comprises at least 2, at least 3, at least 4, at least 5, at least 6, at least 7, or at least 8 lipid-clinical concentration ratios, or combinations thereof.

4. The method of claim 1, wherein the sample is a blood sample, a serum sample or a plasma sample.

5. The method of claim 1, wherein one or more internal standard(s) is (are) added to the sample, and optionally wherein automated lipid extraction is used.

6. The method of claim 1, wherein the MS determination comprises
   (a) ionizing the lipids to generate one or more lipid ions;
   (b) detecting the one or more lipid ions;
   (c) determining the amount of the one or more lipid ions; and/or
   (d) determining the one or more lipid concentration(s), lipid-lipid concentration ratio(s) and/or lipid-clinical concentration ratio(s) in a sample based on the amount of the one or more lipid ions.

7. The method of claim 1, wherein the LC separation comprises using a gradient with solvent A comprising ammonium acetate in water with formic acid and solvent B comprising ammonium acetate in acetonitrile:isopropanol with formic acid.

8. The method of claim 1, wherein the MS is tandem mass spectrometry (MS/MS), and/or the LC is high performance liquid chromatography (HPLC), ultra performance liquid chromatography (UPLC) or ultra high performance liquid chromatography (UHPLC), and optionally wherein UHPLC-MS/MS is used.

9. The method of claim 1, wherein the MS determination is performed in positive and/or negative ion mode, and optionally multiple reaction monitoring, multiple precursor ion scanning and/or neutral loss scanning is used.

10. A method for treating a subject indicated as being at risk of developing one or more CVD complication(s), the method comprising:
   determining whether the subject is at a risk of developing one or more cardiovascular disease (CVD) complication(s)
   wherein said determining comprises:
      (a) extracting lipids from a sample of the subject;
      (b) separating the lipids by liquid chromatography (LC) prior to a mass spectrometry (MS) determination; and
      (c) determining one or more lipid concentration(s), one or more lipid-lipid concentration ratio(s) and/or one or more lipid-clinical concentration ratio(s) in the sample by MS,
   wherein (an) increased or decreased concentration(s) in said sample of the one or more lipid(s), when compared to a control sample, is (are) indicative of said subject having an increased risk of developing one or more CVD complications,
   wherein the one or more lipid(s) whose increase(s) in concentration is (are) compared to the control is (are) selected from:
   Cer(d18:1/16:0), Cer(d18:1/18:0), Cer(d18:1/20:0), Cer(d18:1/22:0), Cer(d18:1/24:1), Cer(d18:1/26:1), LacCer(d18:1/18:0), LacCer(d18:1/20:0), LacCer(d18:1/22:0), LacCer(d18:1/24:0), LacCer(d18:1/24:1), GlcCer (d18:1/18:0), GlcCer(d18:1/20:0), GlcCer(d18:1/24:1), GlcCer(d18:1/26:1), PS O-18:2/16:0-alkenyl, PS O-16:0/18:2-alkenyl, PS O-16:1/18:2-alkyl, PS O-18:0/18:2-alkenyl (PS O-18:1/18:2-alkyl), PC-O-32:0 (KDdiA-PC), PC 16:0/16:0;
   wherein the one or more lipid(s) whose decrease(s) in concentration is (are) compared to the control is (are) selected from:
   PC 18:0/20:4, PC 16:0/20:4, PC 18:0/20:3, PC 16:0/20:3, PC 16:0/22:6, PC 16:0/18:2, PC 18:0/18:1, PC 18:1/18:2, LPC 18:1, PC O-40:3, SM (d18:1/14:0) (d18:1/13:1-OH), SM (d18:1/23:0) (d18:1/22:1-OH), SM (d18:1/24:0) (d18:1/23:1-OH), Cer(d18:0/22:0) and Cer(d18:0/24:0);
   wherein (an) increased or decreased lipid-lipid concentration ratio(s) in said sample, when compared to a control sample, is (are) indicative of said subject having an increased risk of developing one or more CVD complications,
   wherein the one or more lipid-lipid concentration ratio(s) whose increase(s) is (are) compared to the control is (are) selected from:
   Cer(d18:1/18:0)/PC 16:0/18:1, Cer(d18:1/20:0)/PC 16:0/18:1, Cer(d18:1/24:1)/PC 16:0/18:1, Cer(d18:1/24:1)/PC 16:0/18:2, Cer(d18:1/18:0)/PC 18:0/18:1, Cer(d18:1/20:0)/PC 18:0/18:1, Cer(d18:1/24:1)/PC 18:0/18:1, Cer(d18:1/24:1)/PC 18:0/18:2, Cer(d18:1/18:0)/PC 18:1/18:1, Cer(d18:1/20:0)/PC 18:1/18:1, Cer(d18:1/24:1)/PC 18:1/18:1, Cer(d18:1/24:1)/PC 18:1/18:2, Cer(d18:1/18:0)/PC 16:0/20:3, Cer(d18:1/20:0)/PC 16:0/20:3, Cer(d18:1/22:0)/PC 16:0/20:3, Cer(d18:1/24:1)/PC 16:0/20:3, Cer(d18:1/24:1)/PC 18:0/20:3, Cer(d18:1/18:0)/PC 16:0/20:4, Cer(d18:1/20:0)/PC 16:0/20:4, Cer(d18:1/22:0)/PC 16:0/20:4, Cer(d18:1/24:1)/PC 16:0/20:4, Cer(d18:1/18:0)/PC 18:0/20:4, Cer(d18:1/20:0)/PC 18:0/20:4, Cer(d18:1/22:0)/PC 18:0/20:4, Cer(d18:1/24:1)/PC 18:0/20:4, Cer(d18:1/24:1)/PC O-40:3, Cer(d18:1/26:0)/PC O-40:0, PC 16:0/16:0/PC 16:0/20:4, PC O-18:0/18:2-alkyl/PC O-36:5, PC O-32:0 (KDdiA-PC)/PC O-38:5, Cer(d18:1/18:0)/LPC 16:0, Cer(d18:1/16:0)/LPC 18:1, Cer(d18:1/18:0)/LPC 18:1, Cer(d18:1/24:1)/LPC 18:1, Cer(d18:1/22:0)/LPC 18:2, Cer(d18:1/24:1)/LPC 18:2, LacCer(d18:1/18:0)/PC 16:0/18:1, LacCer(d18:1/20:0)/PC 16:0/18:1, LacCer(d18:1/18:0)/PC 18:0/18:1, LacCer(d18:1/20:0)/PC 18:0/18:1, LacCer(d18:1/18:0)/PC 18:1/18:1, LacCer(d18:1/20:0)/PC 18:1/18:1, LacCer(d18:1/18:0)/PC 18:1/18:2, LacCer(d18:1/20:0)/PC 18:1/18:2, LacCer(d18:1/20:0)/PC 18:2/18:2, LacCer(d18:1/18:0)/PC 16:0/20:3, LacCer(d18:1/20:0)/PC 16:0/20:3, LacCer(d18:1/22:0)/PC 16:0/20:3, LacCer(d18:1/24:0)/PC 16:0/20:3, LacCer(d18:1/18:0)/PC 18:0/20:3, LacCer(d18:1/20:0)/PC 18:0/20:3, LacCer(d18:1/22:0)/PC 18:0/20:3, LacCer(d18:1/20:0)/PC 16:0/20:4, LacCer(d18:1/22:0)/PC 16:0/20:4, LacCer(d18:1/20:0)/PC 18:0/20:4, GlcCer(d18:1/20:0)/PC 16:0/20:4, Cer(d18:1/18:0)/SM (d18:1/17:2-OH), Cer(d18:1/18:0)/SM (d18:1/18:1), Cer(d18:1/18:0)/SM (d18:1/14:0) (d18:1/13:1-OH), Cer(d18:1/20:0)/SM (d18:1/14:0) (d18:1/13:1-OH), Cer(d18:1/24:1)/SM (d18:1/17:1-OH), Cer (d18:1/24:1)/SM (d18:1/18:0), Cer(d18:1/24:1)/SM (d18:1/23:0) (d18:1/22:1-OH), Cer(d18:1/24:1)/SM (d18:1/24:0) (d18:1/23:1-OH), LacCer(d18:1/20:0)/SM (d18:1/17:1-OH), LacCer(d18:1/20:0)/SM (d18:1/18:0) and LacCer(d18:1/22:0)/SM (d18:1/14:0) (d18:1/13:1-OH) Cer(d18:1/24:1)/Total PC, Cer(d18:1/18:0)/Total LPC, Cer(d18:1/20:0)/Total LPC, Cer(d18:1/24:1)/Total LPC, Cer(d18:1/18:0)/CE, Cer(d18:1/24:1)/Total CE, Total Cer/Total PC, Total LacCer/Total PC, LacCer(d18:1/22:0)/Total PC, LacCer(d18:1/22:0)/Total LPC, LacCer(d18:1/24:1)/Total PC, LacCer(d18:1/24:1)/Total LPC, LacCer(d18:1/24:1)/Total PC O, SM (d18:1/17:0) (d18:1/16:1-OH)/Total PC O;

wherein the one or more lipid-lipid concentration ratio(s) whose decrease(s) is (are) compared to the control is (are) selected from:

Cer(d18:0/22:0)/Cer(d18:1/18:0), Cer(d18:0/22:0)/Cer(d18:1/20:0), Cer(d18:0/22:0)/Cer(d18:1/22:0), Cer(d18:0/22:0)/Cer(d18:1/24:1), Cer(d18:0/24:0)/Cer(d18:1/16:0), Cer(d18:0/24:0)/Cer(d18:1/18:0), Cer(d18:0/24:0)/Cer(d18:1/20:0), Cer(d18:0/24:0)/Cer(d18:1/22:0), Cer(d18:0/24:0)/Cer(d18:1/24:1), PC 18:1/18:2/PS O-16:0/18:2-alkenyl, PC 18:1/18:2/PS O-16:1/18:2-alkyl, PC 16:0/20:3/PS O-16:0/18:2-alkenyl, PC 16:0/20:3/PS O-16:1/18:2-alkyl, PC 18:0/20:3/PS O-16:0/18:2-alkenyl, PC 18:0/20:3/PS O-16:1/18:2-alkyl, PC 18:0/20:3/PS O-18:2/16:0-alkenyl, PC 16:0/20:4/PS O-16:0/18:2-alkenyl, PC 16:0/20:4/PS O-16:1/18:2-alkyl, PC 18:0/20:4/PS O-16:0/18:2-alkenyl, PC 18:0/20:4/PS O-16:1/18:2-alkyl, PC O-40:3/PS O-18:2/16:0-alkenyl, LPC 18:2/PS O-16:0/18:2-alkenyl, LPC 18:2/PS O-16:1/18:2-alkyl, LPC 16:0/LacCer(d18:1/20:0), LPC 16:0/LacCer(d18:1/22:0), LPC 16:0/LacCer(d18:1/24:0), LPC 16:0/LacCer(d18:1/24:1), LPC 18:1/LacCer(d18:1/20:0), LPC 18:2/LacCer(d18:1/20:0), (d18:1/24:0), Cer(d18:0/24:0)/LacCer(d18:1/24:0), Cer(d18:0/24:0)/SM (d18:1/17:0) (d18:1/16:1-OH), Cer(d18:0/22:0)/PS O-16:0/18:2-alkenyl, Cer(d18:0/22:0)/PS O-16:1/18:2-alkyl, Cer(d18:0/24:0)/PS O-16:0/18:2-alkenyl, Cer(d18:0/24:0)/Total Cer, Cer(d18:0/22:0)/Total CE, Cer(d18:0/24:0)/Total CE, Cer(d18:0/24:1)/Total CE, PC 16:0/20:4/Total DAG and LPC 16:0/Total LacCer;

wherein (an) increased or decreased lipid-clinical concentration ratio(s) in said sample, when compared to a control sample, is (are) indicative of said subject having an increased risk of developing one or more CVD complications, wherein the one or more lipid-clinical concentration ratio(s) whose increase(s) is (are) compared to the control is (are) selected from:

Cer(d18:1/16:0)/apolipoprotein A-I, Cer(d18:1/16:0)/Low Density Lipoprotein (LDL) cholesterol, Cer(d18:1/16:0)/triglycerides, Cer(d18:1/16:0)/total cholesterol, Cer(d18:1/18:0)/apolipoprotein A-I, Cer(d18:1/18:0)/apolipoprotein B, Cer(d18:1/18:0)/HDL cholesterol, Cer(d18:1/18:0)/total-c/HDL-c, Cer(d18:1/18:0)/total cholesterol, Cer(d18:1/18:0)/triglycerides, Cer(d18:1/18:0)/LDL cholesterol, Cer(d18:1/20:0)/apolipoprotein A-I, Cer(d18:1/20:0)/apolipoprotein B, Cer(d18:1/20:0)/High Density Lipoprotein (HDL) cholesterol, Cer(d18:1/20:0)/total cholesterol, Cer(d18:1/20:0)/triglycerides, Cer(d18:1/20:0)/total-cholesterol (total-c)/High Density Lipoprotein-c (HDL-c), Cer(d18:1/20:0)/LDL cholesterol, Cer(d18:1/22:0)/apolipoprotein A-I, Cer(d18:1/22:0)/apolipoprotein B, Cer(d18:1/22:0)/LDL cholesterol, Cer(d18:1/22:0)/triglycerides, Cer(d18:1/22:0)/total cholesterol, Cer(d18:1/24:0)/apolipoprotein A-I, Cer(d18:1/24:0)/apolipoprotein B, Cer(d18:1/24:0)/LDL cholesterol, Cer(d18:1/24:0)/total cholesterol, Cer(d18:1/24:1)/apolipoprotein A-I, Cer(d18:1/24:1)/apolipoprotein B, Cer(d18:1/24:1)/HDL cholesterol, Cer(d18:1/24:1)/Low Density Lipoprotein-c (LDL-c)/HDL-c, Cer(d18:1/24:1)/total-c/HDL-c, Cer(d18:1/24:1)/LDL cholesterol, Cer(d18:1/24:1)/total cholesterol, Cer(d18:1/24:1)/triglycerides, Total Cer/apolipoprotein A-I, Total Cer/apolipoprotein B, Total Cer/LDL cholesterol, Total Cer/total cholesterol, Total Cer/triglycerides, PC O-32:0 (KDdiA-PC)/apolipoprotein A-I, PC O-32:0 (KDdiA-PC)/triglycerides, PC O-34:1/apolipoprotein B, PC O-34:1/triglycerides, LacCer(d18:1/18:0)/apolipoprotein A-I, LacCer(d18:1/18:0)/apolipoprotein B, LacCer(d18:1/18:0)/total cholesterol, LacCer(d18:1/18:0)/HDL cholesterol, LacCer(d18:1/18:0)/LDL cholesterol, LacCer(d18:1/18:0)/total-c/HDL-c, LacCer(d18:1/18:0)/triglycerides, LacCer(d18:1/20:0)/apolipoprotein A-I, LacCer(d18:1/20:0)/apolipoprotein B, LacCer(d18:1/20:0)/total cholesterol, LacCer(d18:1/20:0)/HDL cholesterol, LacCer(d18:1/20:0)/LDL cholesterol, LacCer(d18:1/20:0)/total-c/HDL-c, LacCer(d18:1/20:0)/LDL-c/HDL-c, LacCer(d18:1/20:0)/apoA1/apoB, LacCer(d18:1/20:0)/triglycerides, LacCer(d18:1/22:0)/apolipoprotein A-I, LacCer(d18:1/22:0)/apolipoprotein B, LacCer(d18:1/22:0)/total cholesterol, LacCer(d18:1/22:0)/HDL cholesterol, LacCer(d18:1/22:0)/LDL cholesterol, LacCer(d18:1/22:0)/total-c/HDL-c, LacCer(d18:1/22:0)/apoA1/apoB, LacCer(d18:1/22:0)/triglycerides, LacCer(d18:1/24:0)/apoA1/apoB, LacCer(d18:1/24:1)/apolipoprotein A-I, LacCer(d18:1/24:1)/apolipoprotein B, LacCer(d18:1/24:1)/total cholesterol, LacCer(d18:1/24:1)/triglycerides;

and/or wherein the one or more lipid-clinical concentration ratio(s) whose decrease(s) is (are) compared to the control is (are) selected from:

Cer(d18:0/22:0)/apolipoprotein B, Cer(d18:0/22:0)/LDL-c/HDL-c, Cer(d18:0/22:0)/total-c/HDL-c, Cer(d18:0/24:0)/apolipoprotein A-I, Cer(d18:0/24:0)/apolipoprotein B, Cer(d18:0/24:0)/total cholesterol, Cer(d18:0/24:0)/HDL cholesterol, Cer(d18:0/24:0)/LDL-c/HDL-c, Cer(d18:0/24:0)/total-c/HDL-c, Cer(d18:0/24:0)/LDL cholesterol, PC 18:0/18:1/LDL-c/HDL-c, PC 16:0/20:3/apolipoprotein B, PC 16:0/20:3/HDL cholesterol, PC 16:0/20:3/total-c/HDL-c, PC 16:0/20:3/LDL-c/HDL-c, PC 18:0/20:3/total-c/HDL-c, PC 18:0/20:3/LDL-c/HDL-c, PC 16:0/20:4/apolipoprotein A-I, PC 16:0/20:4/apolipoprotein B, PC 16:0/20:4/total cholesterol, PC 16:0/20:4/LDL cholesterol, PC 16:0/20:4/total-c/HDL-c, PC 16:0/20:4/LDL-c/HDL-c, PC 18:0/20:4/apoA1/apoB, PC O-38:6/apolipoprotein A-I, LPC 18:2/apolipoprotein B, LPC 18:2/total cholesterol, LPC 18:2/HDL cholesterol, LPC 18:2/LDL cholesterol, LPC 18:2/LDL-c/HDL-c and LPC 18:2/apoA1/apoB:

wherein said one or more CVD complication(s) comprise myocardial infarction (MI) and/or death, and treating the subject indicated as being at risk of developing one or more CVD complication(s) based on the determining step, wherein the treating comprises administering a lipid modifying treatment.

11. The method of claim 10, wherein
(a) the CVD complication(s) is(are) atherosclerosis-induced; and/or
(b) the subject has atherosclerosis; or
(c) the subject does not have atherosclerosis.

12. The method of claim 10, wherein the subject
(a) is being or has been treated with one or more statins and/or any other HMG-CoA reductase inhibitor; or
(b) has not yet undergone statin therapy or therapy with any other HMG-CoA reductase inhibitor, and optionally wherein the statin is selected from the group consisting of atorvastatin, cerivastatin, fluvastatin, fluvastatin XL, lovastatin, pitavastatin, pravastatin, rosuvastatin and simvastatin.

13. The method of claim 10, wherein the subject has suffered from the one or more CVD complication(s).

14. The method of claim 10, wherein the lipid modifying treatment comprises a therapeutically effective dose of a drug capable of modulating the one or more lipid concentration(s), lipid-lipid concentration ratio(s) and/or lipid-clinical concentration ratio(s), and further optionally wherein the lipid modifying treatment comprises a statin or any other HMG-CoA reductase inhibitor, niacin (nicotinic acid); a cholesterol absorption inhibitor; a cholesteryl ester transfer protein (CETP) inhibitor; a bile acids sequestrant; a fibrate; or a phytosterol.

* * * * *